(12) United States Patent
Wolf, II

(10) Patent No.: US 11,890,466 B2
(45) Date of Patent: Feb. 6, 2024

(54) IPG AND HEADER COMBINATION

(71) Applicant: Wavegate Corporation, Lake Charles, LA (US)

(72) Inventor: Erich W. Wolf, II, Lake Charles, LA (US)

(73) Assignee: Wavegate Corporation, Lake Charles, LA (US)

( * ) Notice: Subject to any disclaimer, the term of this patent is extended or adjusted under 35 U.S.C. 154(b) by 546 days.

(21) Appl. No.: 16/946,716

(22) Filed: Jul. 1, 2020

(65) Prior Publication Data

US 2021/0001130 A1 Jan. 7, 2021

Related U.S. Application Data

(63) Continuation of application No. 16/946,715, filed on Jul. 1, 2020, which is a continuation of application No. 16/946,714, filed on Jul. 1, 2020.
(Continued)

(51) Int. Cl.
| | |
|---|---|
| *A61N 1/36* | (2006.01) |
| *A61N 1/375* | (2006.01) |
| *G02B 6/02* | (2006.01) |
| *G02B 6/42* | (2006.01) |
| *G02B 6/36* | (2006.01) |

(Continued)

(52) U.S. Cl.
CPC ......... *A61N 1/0553* (2013.01); *A61N 1/0558* (2013.01); *A61N 1/36071* (2013.01); *A61N 1/36139* (2013.01); *A61N 1/3752* (2013.01); *A61N 1/3787* (2013.01); *A61N 1/37518* (2017.08); *G02B 6/02033* (2013.01); *G02B 6/3624* (2013.01); *G02B 6/4212* (2013.01); *G02B 6/4234* (2013.01); *G02B 6/4246* (2013.01); *H02J 7/02* (2013.01); *H02J 50/10* (2016.02); *A61N 1/378* (2013.01); *A61N 1/37223* (2013.01); *H01R 4/30* (2013.01); *H01R 13/08* (2013.01)

(58) Field of Classification Search
CPC ............... A61N 1/0553; A61N 1/0558; A61N 1/36139; A61N 1/37518; A61N 1/3752; A61N 1/3787; A61N 1/378; A61N 1/0551; G02B 6/02033; G02B 6/3624; G02B 6/4212; G02B 6/4234; G02B 6/4246; G02B 6/4293; H02J 7/02; H02J 7/00034; H02J 50/10; H02J 50/80; H01R 4/30; H01R 13/08
See application file for complete search history.

(56) References Cited

U.S. PATENT DOCUMENTS

| | | |
|---|---|---|
| 4,541,440 A | 9/1985 | Parsonnet |
| 4,715,700 A | 12/1987 | Daniel |

(Continued)

*Primary Examiner* — Gary Jackson
*Assistant Examiner* — Alexander M Eisenberg
(74) *Attorney, Agent, or Firm* — Schultz & Associates, P.C.

(57) ABSTRACT

A percutaneous lead is provided which includes a generally tubular, multi-duct, flexible lead body. The lead body supports a distal set of electrodes and a proximal set of contacts which are connected by conductors in the ducts. The lead body further houses an optical fiber with a side firing section. The side firing section is held adjacent an optical transmission window, integrally formed with the flexible lead body. A cylindrical ferrule is provided to position the fiber in the header of an IPG.

24 Claims, 39 Drawing Sheets

Related U.S. Application Data

(60) Provisional application No. 62/869,372, filed on Jul. 1, 2019, provisional application No. 62/869,377, filed on Jul. 1, 2019, provisional application No. 62/869,391, filed on Jul. 1, 2019.

(51) Int. Cl.

| | | |
|---|---|---|
| *H01R 4/30* | (2006.01) | |
| *A61N 1/372* | (2006.01) | |
| *A61N 1/05* | (2006.01) | |
| *H02J 50/10* | (2016.01) | |
| *A61N 1/378* | (2006.01) | |
| *H02J 7/02* | (2016.01) | |
| *H01R 13/08* | (2006.01) | |

(56) References Cited

U.S. PATENT DOCUMENTS

| | | |
|---|---|---|
| 6,011,993 A | 1/2000 | Tziviskos |
| 6,181,865 B1 | 1/2001 | Saviano |
| 6,190,333 B1 | 2/2001 | Valencia |
| 6,324,428 B1 | 11/2001 | Weinberg et al. |
| 7,447,533 B1 * | 11/2008 | Fang ............... A61N 1/375 607/36 |
| 7,742,817 B2 | 6/2010 | Malinowski et al. |
| 7,835,803 B1 | 11/2010 | Malinowski et al. |
| 8,646,172 B2 | 2/2014 | Kuzma et al. |
| 9,550,063 B2 * | 1/2017 | Wolf, II ............ A61N 1/37235 |
| 10,035,019 B2 | 7/2018 | Wolf, II |
| 2004/0175080 A1 | 9/2004 | Yamauchi et al. |
| 2005/0069272 A1 | 3/2005 | Fabian et al. |
| 2007/0100398 A1 | 5/2007 | Sloan |
| 2008/0077190 A1 * | 3/2008 | Kane ................. A61N 1/3752 607/37 |
| 2008/0097554 A1 | 4/2008 | Payne et al. |
| 2008/0183257 A1 | 7/2008 | Imran et al. |
| 2008/0195187 A1 | 8/2008 | Li et al. |
| 2009/0125090 A1 | 5/2009 | Nilsson et al. |
| 2009/0192580 A1 | 7/2009 | Desai |
| 2009/0270953 A1 | 10/2009 | Ecker et al. |
| 2010/0035453 A1 * | 2/2010 | Tronnes ............ A61N 1/3752 439/271 |
| 2010/0256693 A1 | 10/2010 | McDonald et al. |
| 2011/0046700 A1 | 2/2011 | McDonald et al. |
| 2011/0101914 A1 * | 5/2011 | Niessen ............ H01M 10/425 320/107 |
| 2011/0190608 A1 | 8/2011 | Kuhn et al. |
| 2011/0191275 A1 * | 8/2011 | Lujan .................... G06N 20/00 703/2 |
| 2013/0030352 A1 | 1/2013 | Seymour et al. |
| 2013/0317572 A1 | 11/2013 | Zhu et al. |
| 2014/0148753 A1 * | 5/2014 | Leven ................ A61N 1/0551 604/21 |
| 2014/0296952 A1 | 10/2014 | Dabney et al. |
| 2014/0330341 A1 | 11/2014 | Wolf, II |
| 2014/0340741 A1 | 11/2014 | Adachi |
| 2015/0093082 A1 | 4/2015 | Lu et al. |
| 2016/0250471 A1 | 9/2016 | Khalil et al. |
| 2016/0341899 A1 | 11/2016 | Yokoyama |
| 2018/0110971 A1 | 4/2018 | Carmona |
| 2018/0147077 A1 | 5/2018 | Scharschmidt et al. |
| 2018/0154152 A1 | 6/2018 | Chabrol et al. |
| 2018/0326219 A1 | 11/2018 | Wolf, II |
| 2018/0344130 A1 | 12/2018 | Gmeiner et al. |
| 2019/0060656 A1 * | 2/2019 | Scott .................. A61N 1/0531 |
| 2021/0281003 A1 | 9/2021 | Zucca et al. |

* cited by examiner

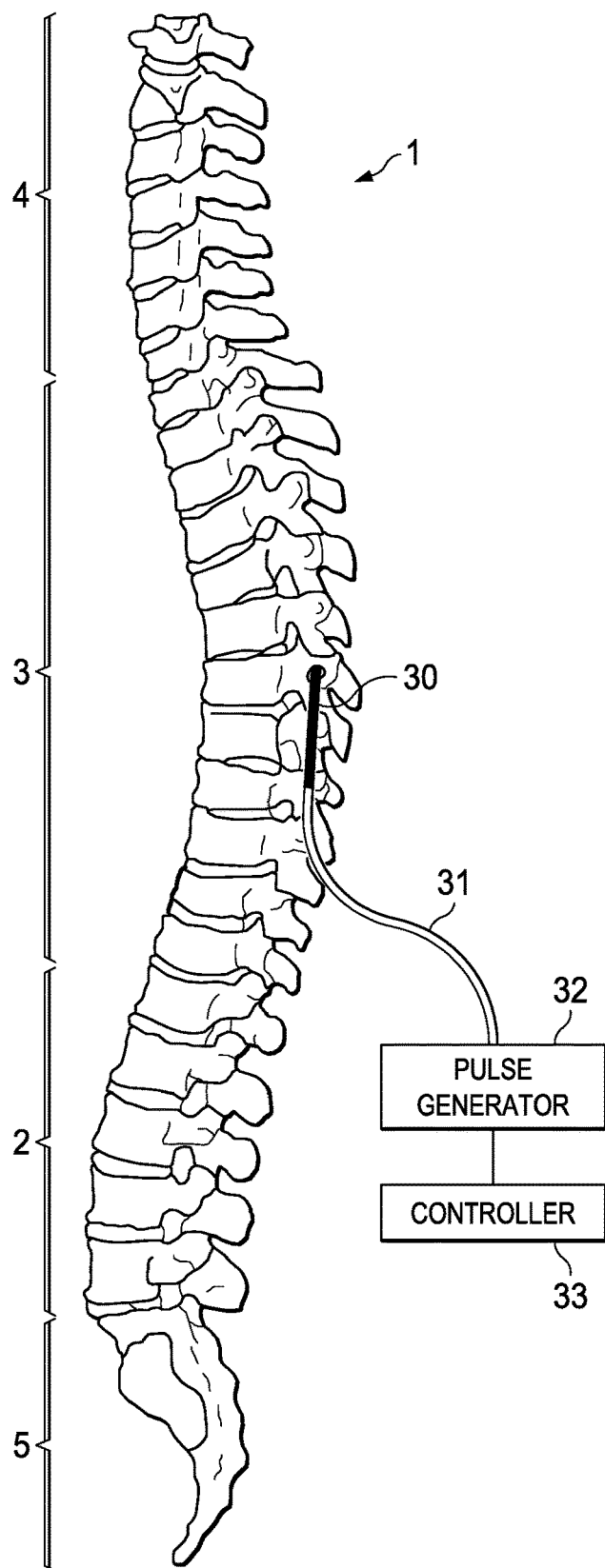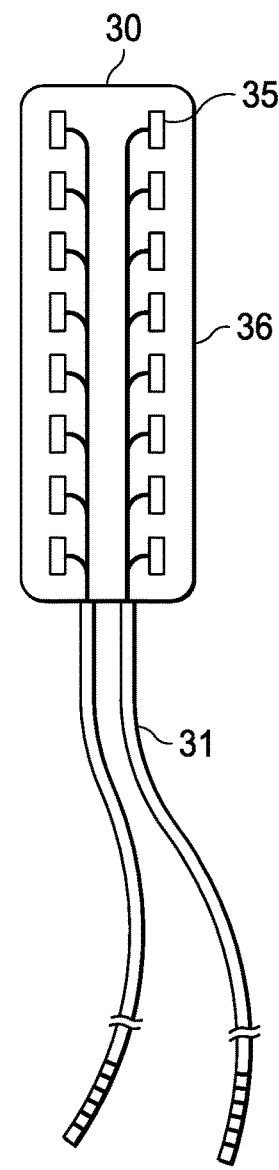
FIG. 1
(PRIOR ART)
FIG. 4
(PRIOR ART)

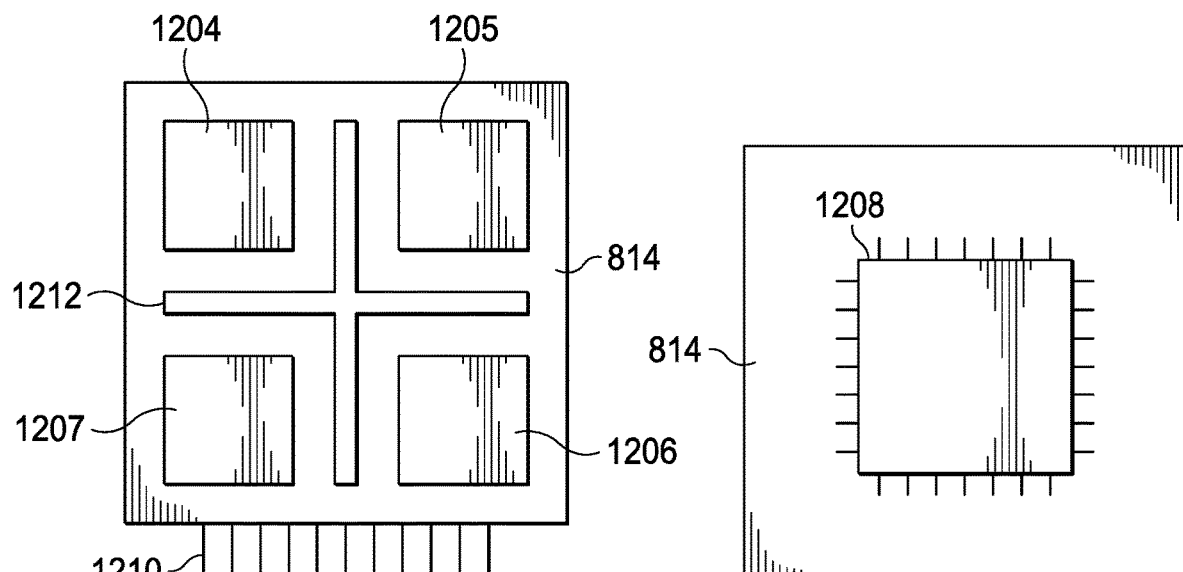
FIG. 12A
FIG. 12B
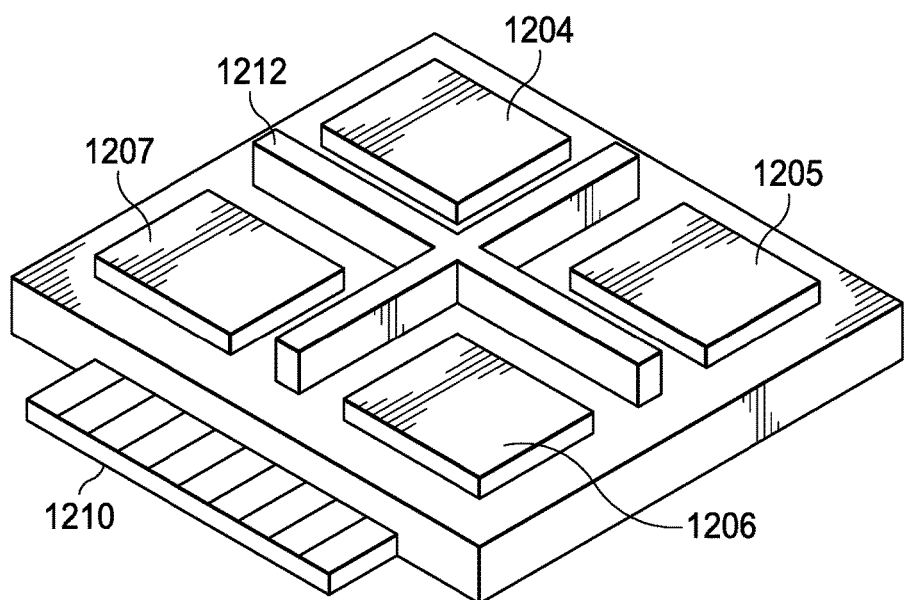
FIG. 12C

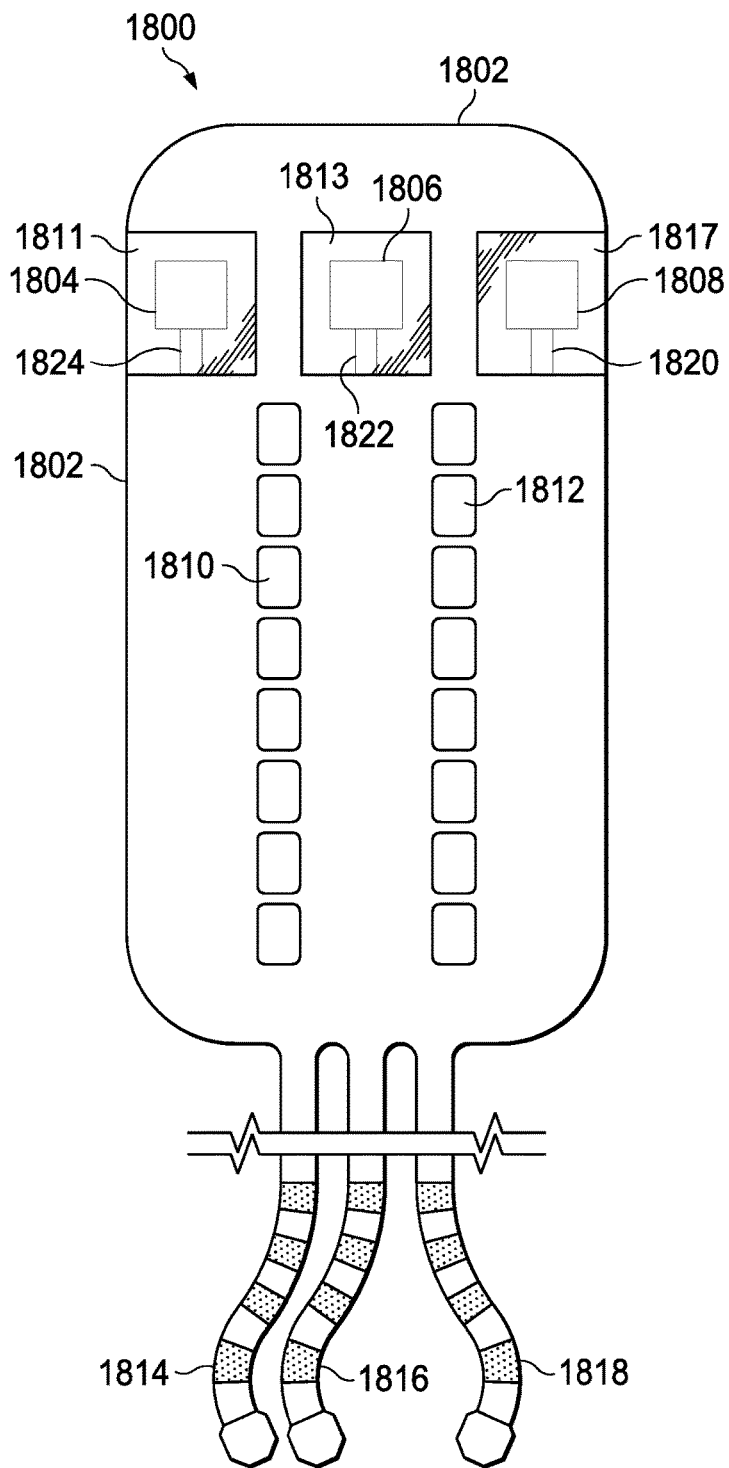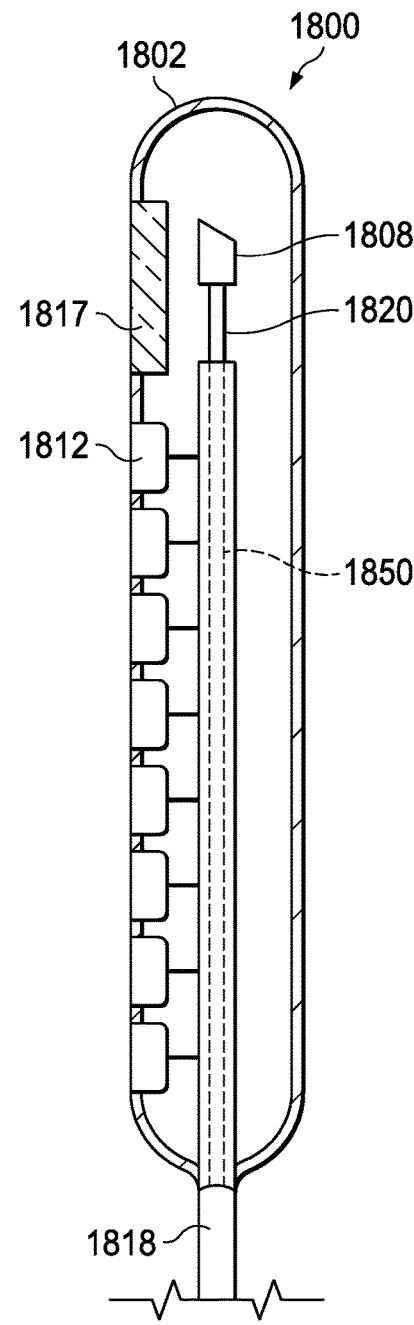
FIG. 17A
FIG. 17B

IPG AND HEADER COMBINATION

CROSS-REFERENCE TO RELATED APPLICATIONS

This application is a continuation of U.S. application Ser. No. 16/946,715 filed on Jul. 1, 2020, which is a continuation of U.S. application Ser. No. 16/946,714 filed on Jul. 1, 2020. This application claims priority benefits from U.S. Provisional Application No. 62/869,372 filed on Jul. 1, 2019; U.S. Provisional Application No. 62/869,377 filed on Jul. 1, 2019 and U.S. Provisional Application No. 62/869,391 filed on Jul. 1, 2019. The patent applications identified above are incorporated herein by reference in its entirety to provide continuity of disclosure.

FIELD OF THE INVENTION

The present invention relates to an improved implantable pulse generator (IPG) and header combination for using optical reflectometry in spinal cord stimulation (SCS).

BACKGROUND OF THE INVENTION

Chronic pain may arise from a variety of conditions, most notably from nerve injury as in the case of neuropathic pain, or from chronic stimulation of mechanical nociceptors such as with spinal pain. Functional ability may be severely impacted by pain, which often is refractory to pharmacological and surgical treatment. In such cases, spinal cord stimulation ("SCS") can be an effective treatment for pain by modulating physiological transmission of pain signals from the periphery to the brain. This may be achieved by applying electrical impulses to the spinal cord via an electrode array implanted adjacent the spinal canal.

Spinal cord stimulator (SCS) system electrode leads may be classified as either "percutaneous leads" or "surgical leads". Percutaneous lead arrays contain multiple cylindrical electrode contacts which are arranged colinear along a thin cylindrical cable which is introduced into the body via a needle. In contradistinction, surgical leads are generally comprised of an array of electrode contacts which protrude on one side from a thin lead body composed of a flexible substrate which is directly placed in the dorsal epidural space via a surgical laminotomy.

In FIG. 1, spinal column 1 is shown to have a number of vertebrae, categorized into four sections or types: lumbar vertebrae 2, thoracic vertebrae 3, cervical vertebrae 4 and sacral vertebrae 5. Cervical vertebrae 4 include the 1st cervical vertebra (C1) through the 7th cervical vertebra (C7). Just below the 7th cervical vertebra is the first of twelve thoracic vertebrae 3 including the 1st thoracic vertebra (T1) through the 12th thoracic vertebra (T12). Just below the 12th thoracic vertebrae 3, are five lumbar vertebrae 2 including the 1st lumbar vertebra (L1) through the 5th lumbar vertebra (L5), the 5th lumbar vertebra being attached to sacral vertebrae 5 (S1 to S5), sacral vertebrae 5 being naturally fused together in the adult.

In FIG. 2, representative vertebra 10, a thoracic vertebra, is shown to have a number of notable features which are in general shared with lumbar vertebrae 2 and cervical vertebrae 4. The thick oval segment of bone forming the anterior aspect of vertebra 10 is vertebral body 12. Vertebral body 12 is attached to bony vertebral arch 13 through which spinal nerves 11 run. Vertebral arch 13, forming the posterior of vertebra 10, is comprised of two pedicles 14, which are short stout processes that extend from the sides of vertebral body 12 and bilateral laminae 15. The broad flat plates that project from pedicles 14 join in a triangle to form a hollow archway, spinal canal 16. Spinous process 17 protrudes from the junction of bilateral laminae 15. Transverse processes 18 project from the junction of pedicles 14 and bilateral laminae 15. The structures of the vertebral arch protect spinal cord 20 and spinal nerves 11 that run through the spinal canal.

Surrounding spinal cord 20 is dura 21 that contains cerebrospinal fluid (CSF) 22. Epidural space 24 is the space within the spinal canal lying outside the dura.

Referring to FIGS. 1, 2 and 3, the placement of an electrode array for spinal cord stimulation according to the prior art is shown. Electrode array 30 is positioned in epidural space 24 between dura 21 and the walls of spinal canal 16 towards the dorsal aspect of the spinal canal nearest bilateral laminae 15 and spinous process 17.

FIG. 4 shows a prior art surgical electrode array 30 including electrode contacts 35 sealed into elastomeric housing 36. Electrode array 30 has electrode leads 31 which are connected to electrical pulse generator 32 and controller 33. Each electrode contact has a separate electrical conductor in electrode leads 31 so that the current to each contact may be independently controlled.

Spinal cord stimulators often include an implantable pulse generator (IPG) 32 which monitors and delivers the electrical stimulation to the spinal cord through the electrode array 31. The IPG is typically contained in a titanium canister which is implanted subcutaneously near the upper buttocks or flank and draws power from a battery. The electrode array is connected to the IPG using subcutaneous leads.

The subcutaneous leads interface with electrode contacts located in the header of an IPG. Typically, the leads are secured in the IPG with an anchor screw.

The IPG delivers pulses of electrical current to the electrode array, which travel through the electrodes to targeted neurons within the ascending tracts of the spinal cord. The resulting electric field disrupts the perception of pain. Controlling the amplitude of the stimulating electrical field is paramount to success of spinal cord stimulation. Applying inadequate current will fail to depolarize the targeted neurons, rendering the treatment ineffective. Conversely, application of excess current will depolarize the targeted neurons, but also stimulate additional cell populations which renders the perception of a noxious stimulation.

Establishing a consistent, therapeutic, and non-noxious level of stimulation is predicated upon establishing an ideal current density within the spinal cord's targeted neurons. Fundamentally, this should be a simple matter of establishing an optimal electrode current given the local bulk conductivity of the surrounding tissues. But in practice, the optimal electrode current changes as a function of patient position and activity due to motion of the spinal cord as the spinal cord floats in cerebrospinal fluid within the spinal canal. Significant changes in distance between the epidural electrode array and the targeted spinal cord neurons have been shown to occur. Consequently, optimal stimulation requires dynamic adjustment of the electrode stimulating current as a function of distance between the electrode array and the spinal cord.

Dynamic modulation of spinal cord stimulator electrode current as a function of distance between the electrode array and the spinal cord thus has several benefits. Excess stimulation current can be avoided, thus reducing the prospects of noxious stimulation and potentially reducing device power consumption. Inadequate stimulation current can also be avoided, thus eliminating periods of compromised therapeutic efficacy.

Dynamic modulation of electrode current can be controlled through the use of optical reflectometry to determine the thickness of the dorsal cerebrospinal fluid (dCSF) column between the spinal cord and the electrode array. An optical signal is transmitted into the surrounding tissue and collected by a sensor to calculate the approximate distance between the electrode and the spinal cord. The stimulus magnitude is modified accordingly to provide the optimal current for pain relief. An example of this technology is shown in U.S. Pat. No. 10,035,019 to Wolf II, incorporated herein by reference.

One challenge to subcutaneous IPG implants is the long-term survival of the IPG in the harsh in vivo environment. Functional and mechanical degradation may occur with the ingress of body fluids. Proteins common in the blood and interstitial fluid are known to bind to metallic ions, leading to corrosion. Some materials can trigger an immune response and potentially a change in the local pH balance of the implantation site. Specialized polymers and epoxies can avoid some of these problems, but often exhibit unacceptably high levels of cytotoxicity. Consequently, it is imperative to maintain the IPG internal components in a hermetically sealed environment and that the external IPG components be biocompatible.

Similarly, another challenge to subcutaneous IPG implants is the tendency for the surrounding tissue to degrade around the IPG due to increased pressure the IPG edges place on the tissue. Erosion of the device through the skin can occur, typically at the corners of the device where there is a focal concentration of pressure, and requires revision surgery to replace the device.

Another challenge to implementation of optical reflectometry for adaptive spinal cord stimulation is that leads coupled imprecisely to the IPG header are susceptible to movement which interferes with the stability of the optical signal. Unstable optical signals result in undesirable signal-to-noise ratio which results in errors in delivered current and imprecise stimulation.

Yet another challenge to subcutaneous IPG implants is the extended recharge times. IPGs including a rechargeable battery must be periodically recharged. Electromagnetic induction has evolved as the most widely used technology for recharging IPG batteries. However, during recharging, eddy currents are produced in the IPG casing causing temperature increase. To maintain an acceptable temperature, charging duty cycles are typically shorter than ideal, thereby increasing the time required for recharging.

The prior art has attempted to address these challenges in a number of ways.

For example, U.S. Pat. No. 6,011,993 to Tziviskos, et al. describes a method of making a strong ceramic case that can house electronics with a good hermetic seal for implantation into the body. However, Tziviskos does not describe how to effectively connect or secure electrical leads or optical fibers.

As another example, U.S. Pat. No. 6,324,428 to Weinberg, et al. describes a medical implant that contains the internal electronics in a preferred configuration that minimizes the volume of the implant, making it easier to implant. However, Weinberg does not describe any design feature that reduces device erosion, nor does it disclose how to couple electrical leads or optical fibers to the implant.

Similarly, U.S. Pat. No. 7,742,817 to Malinowski, et al. describes an IPG with connectors for electrical leads and an epoxy coating for biocompatibility. However, Malinowski does not disclose the use of optics in the design to achieve proper pulse strength.

Deficiencies exist in the prior art related to the accuracy of lead coupling when using optical reflectometry for spinal cord stimulation. Thus, there is a need in the art for an improved IPG case, connectors, leads and electrodes which provide a stable optical signal while optimizing the longevity of the IPG.

BRIEF DESCRIPTION OF THE DRAWINGS

In the detailed description of the preferred embodiments presented below, reference is made to the accompanying drawings.

FIG. 1 is a side view of the human spine showing the approximate position of an electrode array for spinal cord stimulation.

FIG. 4 shows a prior art surgical electrode array and lead connector for spinal cord stimulation.

FIG. 12A is a front view of a preferred daughterboard for an improved IPG device.

FIG. 12B is a rear view of a preferred daughterboard for an improved IPG device.

FIG. 12C is an isometric view of a preferred daughterboard for an improved IPG device.

FIG. 17A is a plan view of a surgical lead.

FIG. 17B is a cross-sectional view of a surgical lead.

DETAILED DESCRIPTION OF THE INVENTION

In the description that follows, like parts are marked throughout the specification and figures with the same numerals, respectively. The figures are not necessarily drawn to scale and may be shown in exaggerated or generalized form in the interest of clarity and conciseness.

Figure 2:
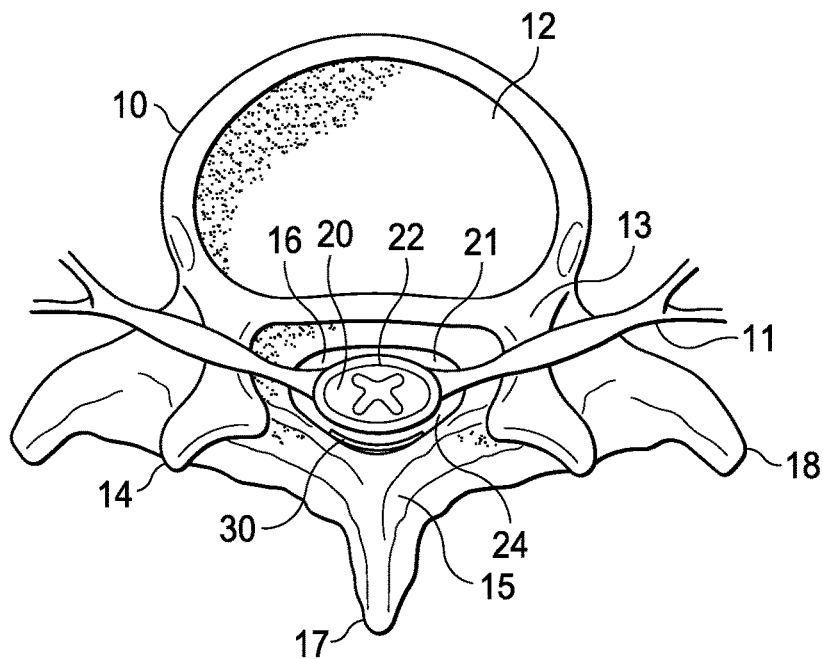
FIG. 2 shows an axial view of a thoracic vertebra indicating the position of the spinal cord and an electrode array for spinal cord stimulation.
Figure 3:
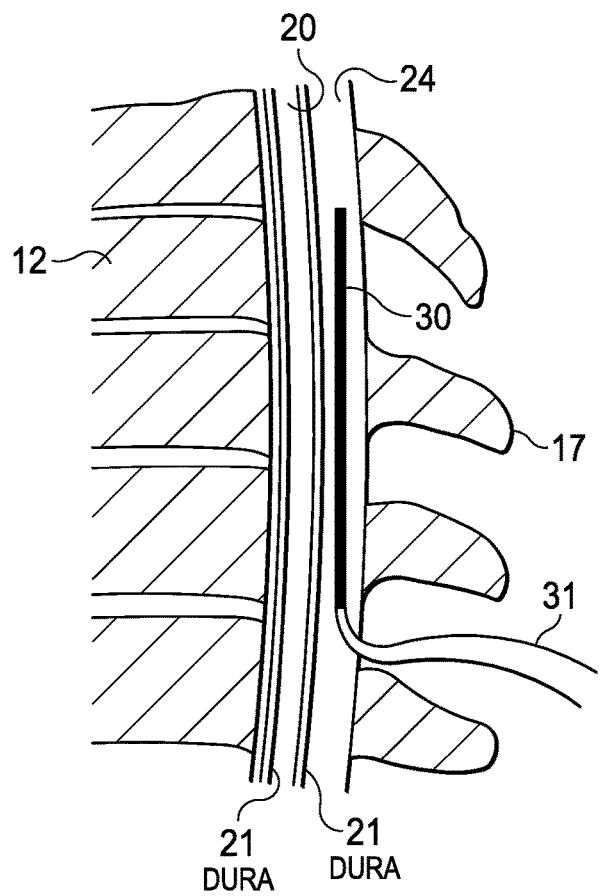
FIG. 3 shows a sagittal cross-sectional view of the human spine showing the approximate position of an electrode array for spinal cord stimulation.
Figure 5:
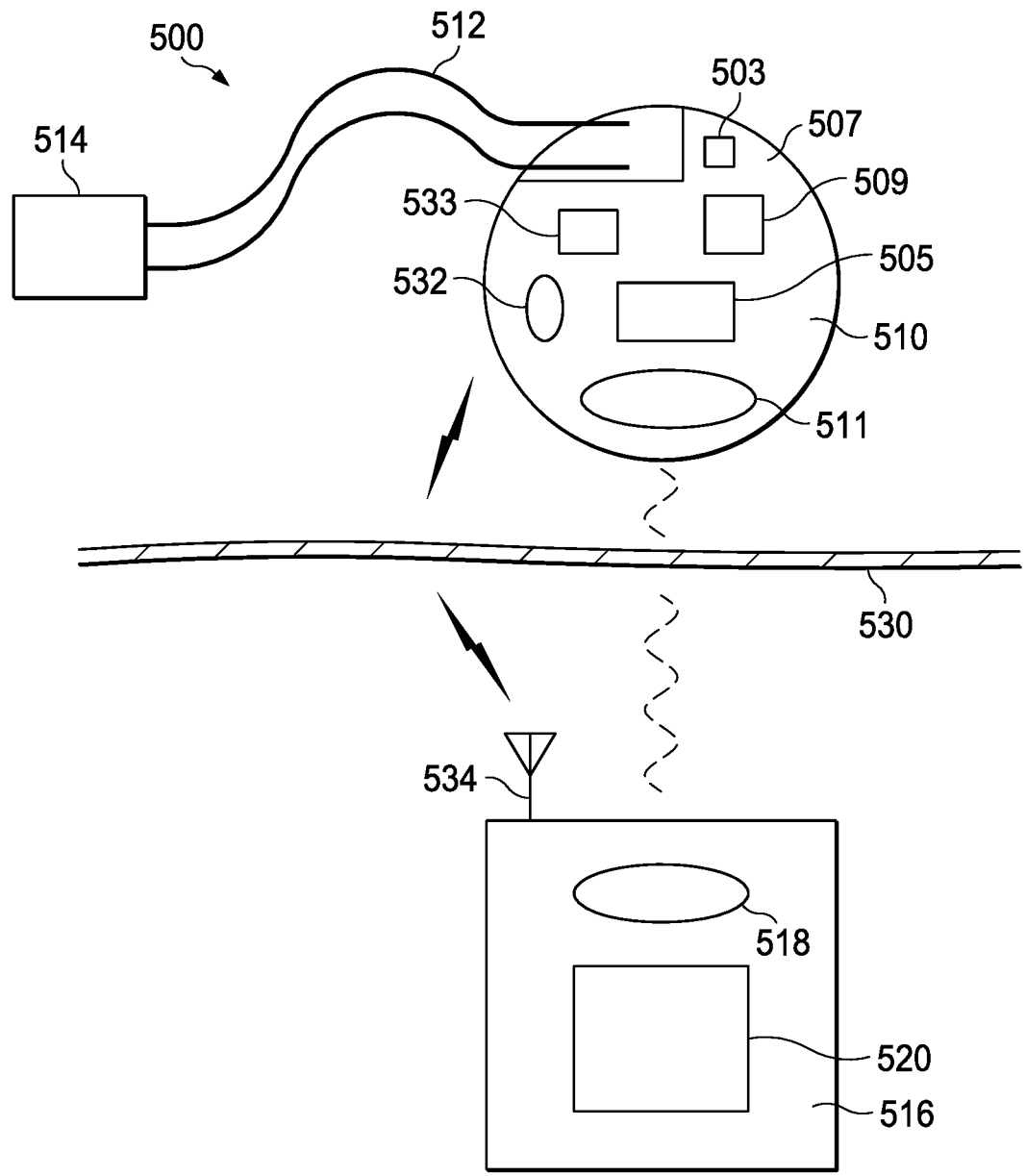
FIG. 5 shows a schematic of an IPG charging and communication system of a preferred embodiment.

Referring then to FIG. 5, IPG charging and communication system 500 comprises an IPG device 510 implanted subcutaneously beneath skin surface 530.

IPG device 510 comprises an external non-metallic case 507 which facilitates transmission of charging and communication signals, with external system manager 516, as will be further described.

IPG device 510 further comprises main processor 505, operatively connected to signal processor 509. Main processor 505 is further operatively connected to secondary coil 511 and RF antenna 532, as will be further described.

Signal processor 509 is operatively connected to optoelectrical devices 503, as will be further described.

Optoelectrical devices 503 are positioned to send and receive light into and out of, respectively, leads 512 of surgical lead 514, as will be further described.

Main processor 505 is further operatively connected to battery 533, secondary coil 511 and RF antenna 532. In use, main processor 505 mitigates charging battery 533 from current induced in secondary coil 511, by primary coil 518, as will be further described. Main processor 505 further receives signals from RF antenna 532, for use in communicating data regarding operation of the IPG device, as will be further described.

The system further comprises external system manager 516. External system manager 516 includes external processor 520, operatively connected to primary coil 518 and RF antenna 534.

In use, external processor 520 includes a set of instructions which control a charging signal sent to primary coil 518. In use, primary coil 518 is placed physically near secondary coil 511 and activated. The activation of the primary coil induces a current in the secondary coil which is routed to the battery by the main processor for charging the battery. The activation of the primary coil and the inductive charging of the battery can be continuous since there are no eddy currents created in the non-metallic case. A continuous charging duty cycle for an IPG is a significant improvement over the prior art which reduces IPG charging time.

RF antenna 534 is used to send and receive signals to RF antenna 532 to receive information and control operation of IPG device 510, as will be further described.

Figure 6A:
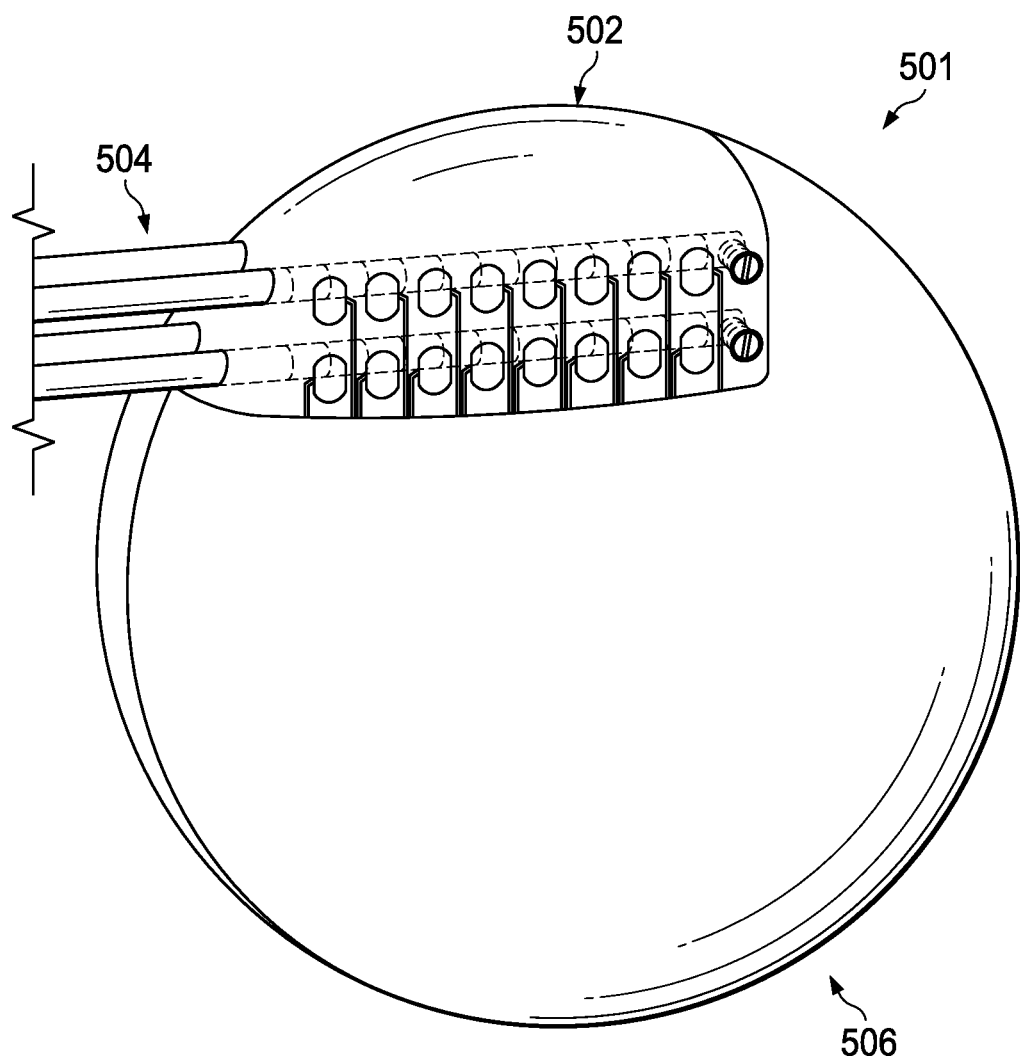
FIG. 6A is an isometric view of a preferred IPG device.

Referring then to FIG. 6A, IPG device 501 comprises IPG body 506 and header 502. Leads 504 are removably secured in the header, as will be further described.

Referring then to FIGS. 6B, 6C, 6D and 6E, the preferred shape for IPG device 501 will be described. In general, the preferred shape of the IPG case is defined by two (2) unique super ellipse equations, one for each of the side and top perspectives. The case is symmetrical about each principal axis. The external shape of the IPG case is important because a near Gaussian distribution of curvatures over the surface greatly reduces the risk of erosion of the case through the skin after implantation of the IPG device, thereby increasing the survivability of the surgical implant. The preferred super ellipse equations which define the shape of the case are preferably Lamé curve equations.

The device three-dimensional shape is a volume of revolution having principle axes x, y and z. The volume of revolution is symmetrical about each principle axis. Referring to FIG. 6C, from the front, in the x y plane, the volume of revolution is preferably a circle, defined by the equation:

$$\left|\frac{a}{2}\right|^2 + \left|\frac{b}{2}\right|^2 = r^2 \qquad \text{Eq. 1}$$

where:
a=width along the x axis;
b=height along the y axis;
r=radius.

Typical values for a and b are about 50 mm. A typical value for r is about 25 mm.

Figure 6B:
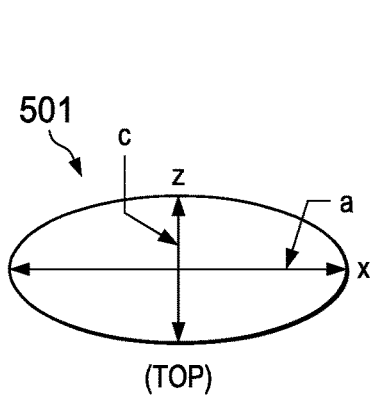
FIG. 6B is a cross-sectional top view of a preferred IPG shape demonstrating a super ellipse curve.
Figure 6C:
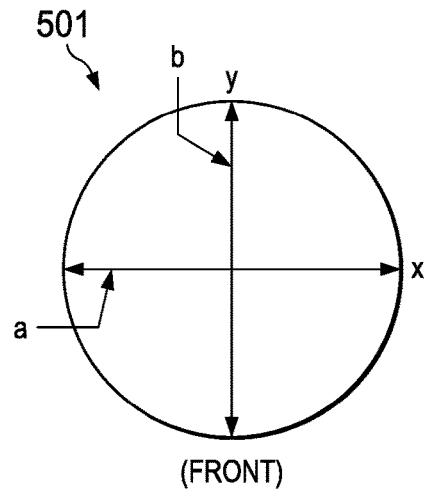
FIG. 6C is a cross-sectional front view of a preferred IPG shape demonstrating a super ellipse curve.
Figure 6D:
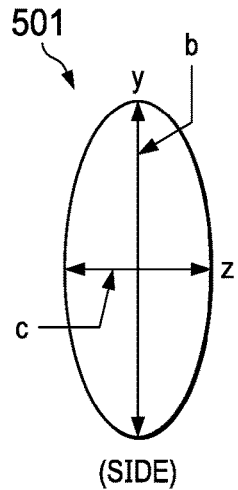
FIG. 6D is cross-sectional side view of a preferred IPG shape demonstrating a super ellipse curve.
Figure 6E:
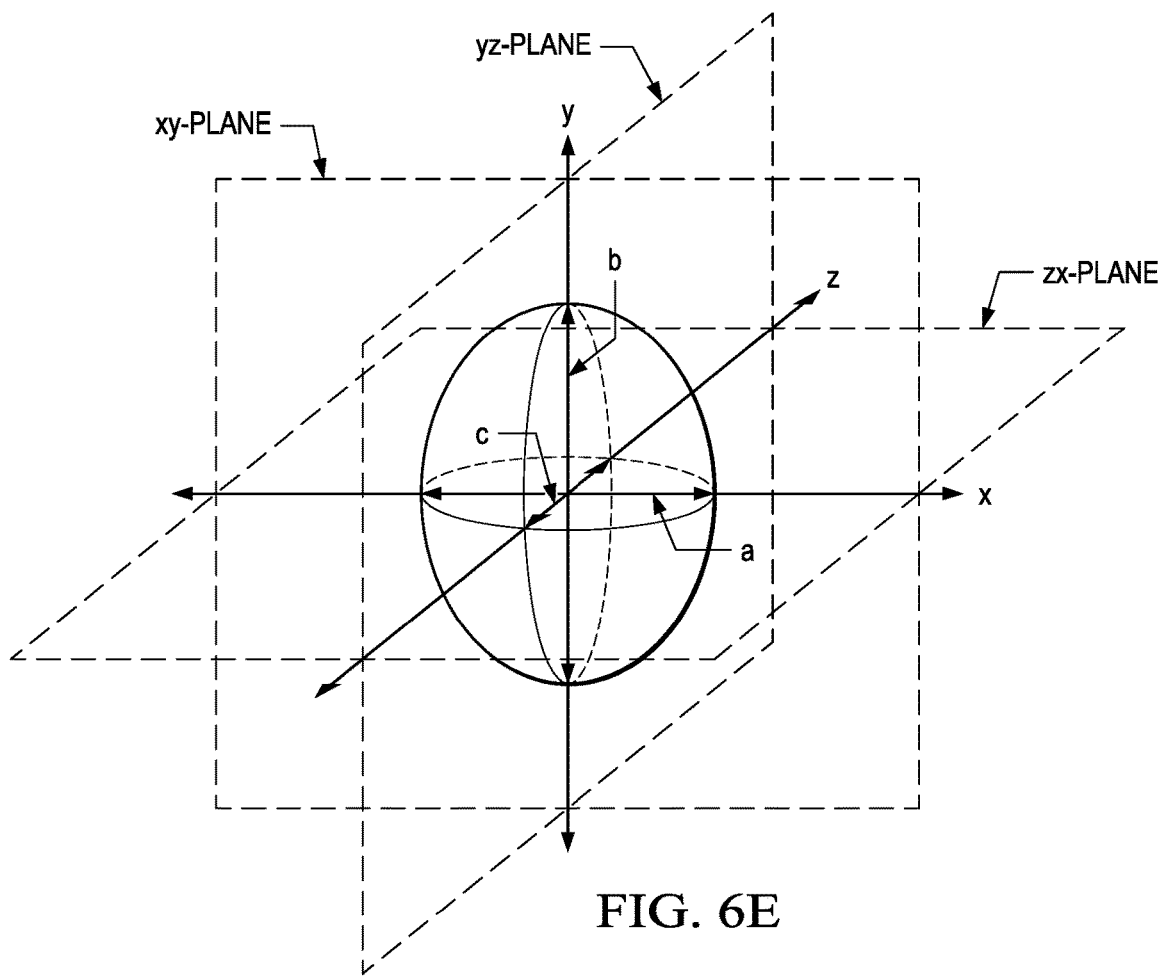
FIG. 6E is an isometric view of a preferred IPG shape demonstrating a super ellipse curve.

Referring to FIG. 6D, from the side, in the y z plane the volume of revolution is preferably a super-ellipse defined by the equation:

$$\left|\frac{z}{c}\right|^n + \left|\frac{y}{b}\right|^n = 1 \qquad \text{Eq. 2}$$

where:
b=height along the y axis;
c=depth along the z axis;
n is between about 1.5 and about 5, and is preferably about 2.

A typical value for b is about 50 mm. A typical value for c is about 12 mm.

In one preferred embodiment, the super ellipse in the y z plane is rotated about the z axis to obtain the volume of revolution.

Referring to FIG. 6B, from a top, in the x z plane, the volume of revolution is preferably a super-ellipse defined by the equation.

$$\left|\frac{x}{a}\right|^n + \left|\frac{z}{c}\right|^n = 1 \qquad \text{Eq. 3}$$

where:
a=width along the x axis;
c=depth along the z axis;

A typical value for a, is about 50 mm. A typical value for c, is about 12 mm.

Figure 6F:
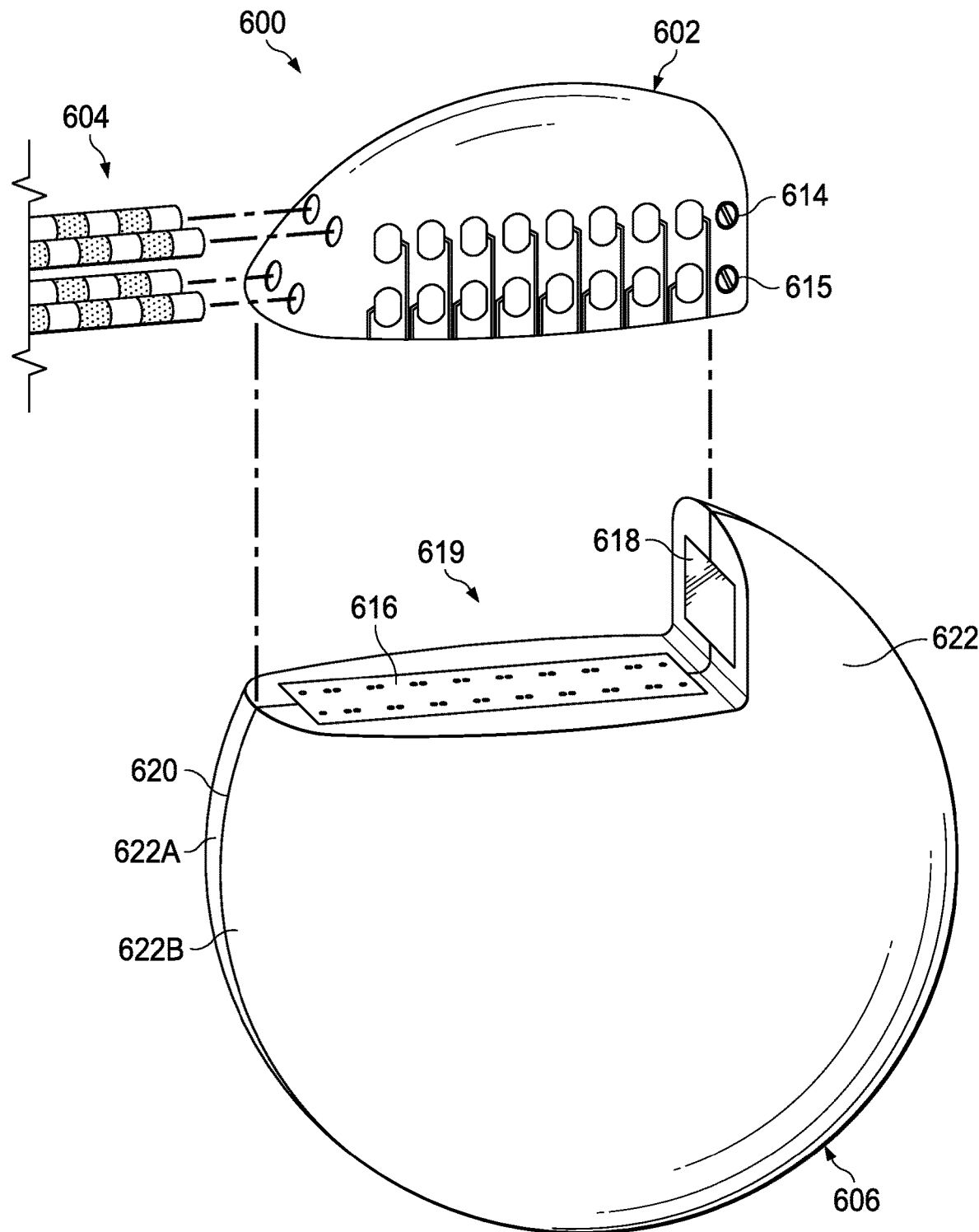
FIG. 6F is an exploded isometric view of a preferred IPG device.

Referring then to FIG. 6F, an exploded view of improved IPG device 600 will be described.

IPG device 600 is comprised of header 602 and IPG body 606. IPG body 606 is further comprised of IPG casing 622, optical window 618 and electrical feedthrough plate 616. IPG casing 622 is formed by two opposing shell halves, 622a and 622b, hermetically sealed at junction 620. In a preferred embodiment, IPG casing 802 is a ceramic material, such as alumina, sapphire or zirconia. In another embodiment, the IPG casing may be formed of a molded amorphous glass, such as Pyrex °. In alternative embodiments, the IPG casing may be comprised of titanium or an alloy. In a preferred embodiment, ceramic brazing with induced welding is applied at the junction of the casing halves. Other processes may be used to join the halves.

The header is fixed in header bay 619 by a suitable medical grade permanent adhesive, as will be further described.

Optical window 618 is preferably a crystal insert in a wall of the header bay that is hermetically sealed in the IPG casing, as will be further described. Alternatively, in embodiments where the IPG casing is formed of an optically transparent material, optical window 618 may take the form of a pair of polished surfaces integrally formed in the header bay wall, of the IPG casing, adjacent the header body.

Leads 604 are removably coupled with header 602 and secured in place using anchor screws 614 or 615, as will be further described.

Figure 7A:
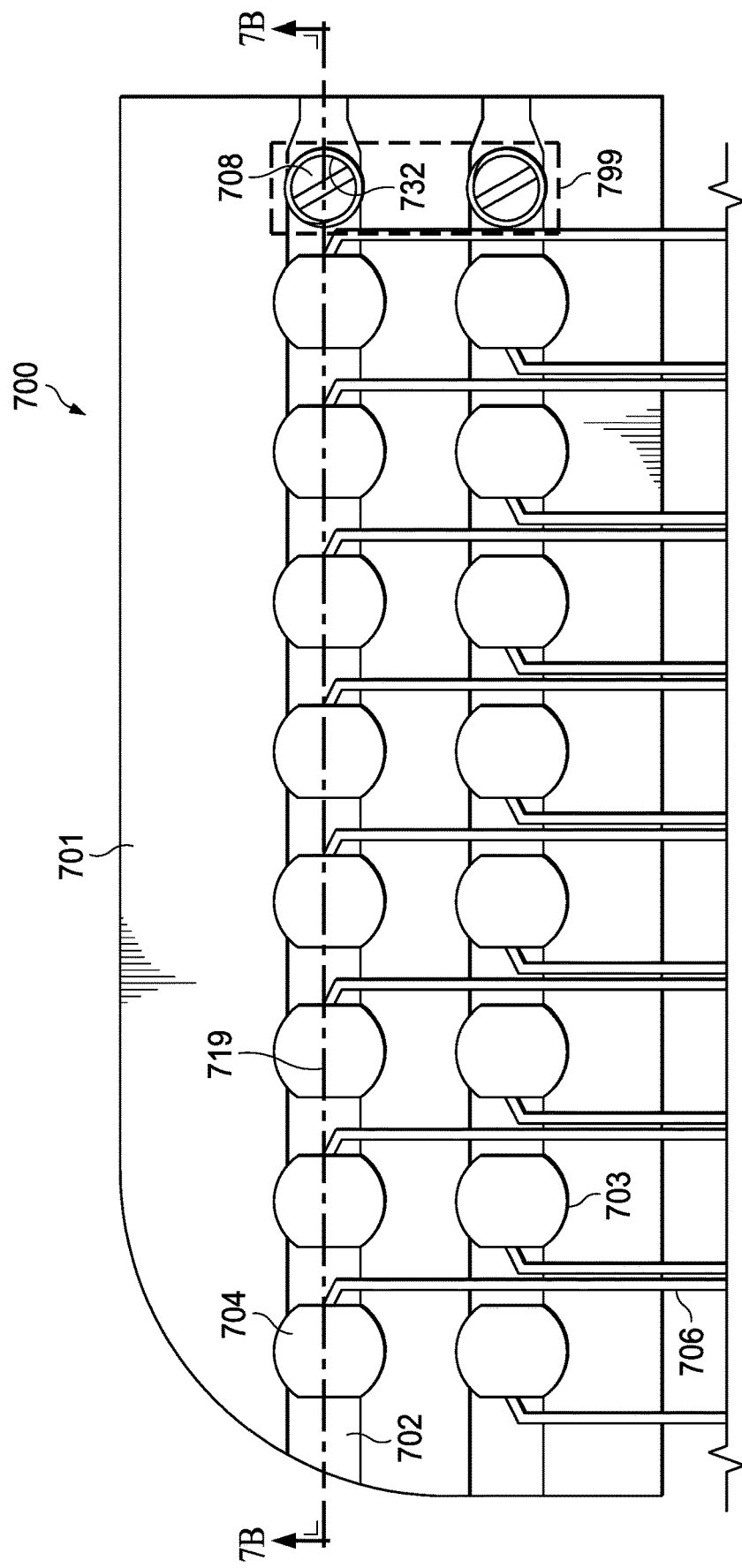
FIG. 7A is a side view of a header for a preferred IPG device.

Referring then to FIG. 7A, header 700 is comprised of header body 701. The header body is preferably formed of a cast rigid non-metallic material of sufficient strength to support radial forces from the anchor screws, such as methyl PMMA or polyester reinforced with fiberglass or graphite fibers. The header body includes a plurality of generally latitudinal and parallel lead channels, such as lead channel 702. In a preferred embodiment, the header body includes four lead channels. Alternatively, it may have two lead channels. Each lead channel, such as lead channel 702 is generally cylindrical and includes a lead channel axis, such as axis 719, which forms an optical axis for the lead, as which will be further described.

Each lead channel includes eight annular connector bays such as connector bay 703, formed inline on the interior of each channel. Connector bays 703 are equally spaced along the channel axis of each lead channel. Each connector bay houses a canted coil connector spring, such as canted coil spring 704. Each canted coil connector spring is a helical metallic coil which forms a toroid and which is spring loaded to exert an internally directed radial bias against a metallic lead connector, as will be further described. Preferably, the canted coil springs are platinum alloy to assure failsafe electrical and mechanical contact with the lead contacts. In a preferred embodiment, the canted coil springs are Bal Conn® for Neuromodulation available from B al-Seal Engineering of Foothill Ranch, California. Each of the canted coil springs is connected to one connector pin, such as connector pin 706, located at the base of the header.

Header body 701 includes a set of horizontal threaded holes, perpendicular to the lead channels, such as threaded hole 732, adjacent the IPG casing, extending from the exterior of the header body to the lead channel. An anchor screw, such as anchor screw 708, is located in each threaded hole.

In a preferred embodiment, the threaded holes are tapped or cast directly into the header body or alternatively cast into the IPG casing. This configuration is important because it eliminates the need for a separate anchoring block in the header and conserves space by incorporating these components into the IPG casing. Furthermore, placement of the anchoring screw nearest the proximal end of the lead channel provides a secure mechanical connection of the lead closest to the optical components, promoting a stable optical signal.

Optionally, the header body may further comprise an integrally formed anchor block 799. In this embodiment, the threaded holes and anchor screws are resident in the anchor block adjacent the optical window. The anchor block is preferably a medically inert metal such as titanium molded into the header body.

Figure 7B:
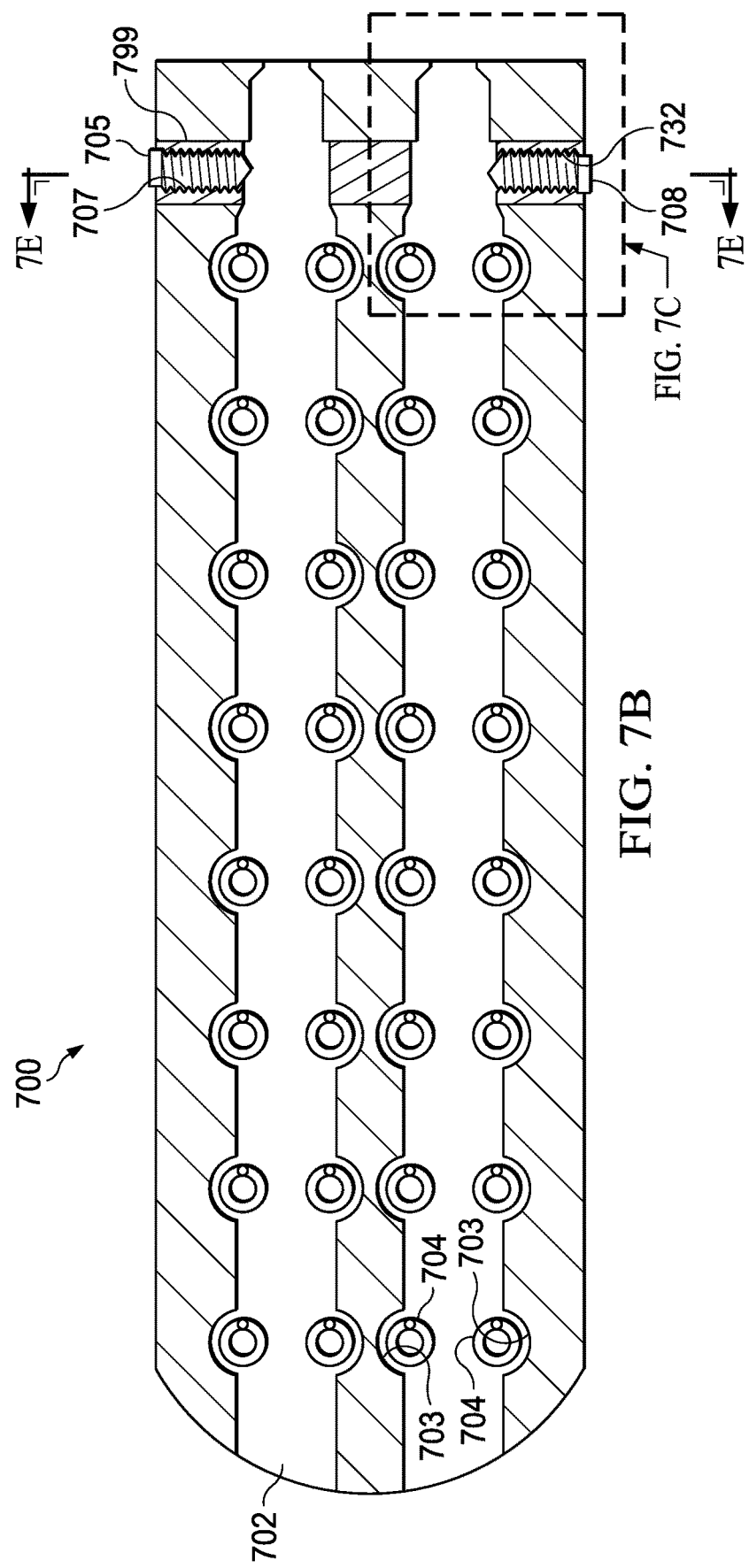
FIG. 7B is a cross-sectional top view of a header for a preferred IPG device.

Referring then to FIG. 7B, threaded hole 732 houses anchor screw 708. Diametrically opposed to threaded hole 732 is threaded hole 707. Threaded hole 707 houses anchor screw 705.

Figure 7C:
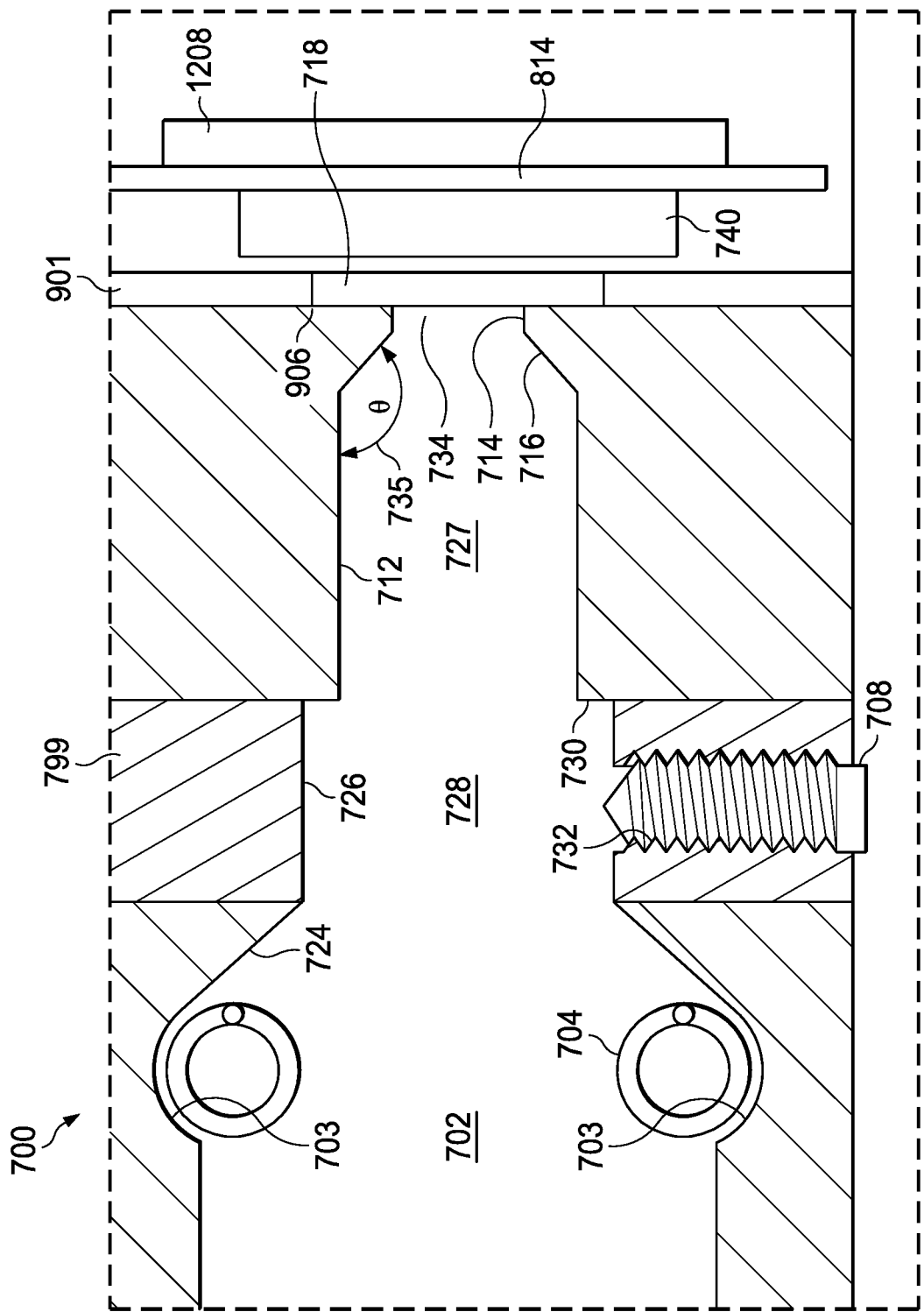
FIG. 7C is a detail view a preferred header for an improved IPG device.

Referring then to FIG. 7C, frustoconical centering surface 724 is adjacent to and coaxial with lead channel 702. Frustoconical centering surface 724 centers the lead on the optical axis of the lead channel as it is inserted into the lead channel. The frustoconical centering surface is adjacent anchor ring chamber 728. The anchor ring chamber is bounded by cylindrical alignment surface 726 and is coaxial with the frustoconical centering surface. The anchor ring chamber is also bounded by stop surface 730. Stop surface 730 is an annular ring at the proximal end of the anchor ring chamber. The stop surface is coaxial with the anchor ring chamber. In use, stop surface 730 abuts the proximal end of the lead body and prevents it from being inserted past the desired point in lead channel 702 during assembly. Each of these surfaces is important for accurate positioning of the lead and the optical fiber and promotes efficient and accurate optical signal transfer.

Anchor screw 708 engages the lead anchor ring in the anchor ring chamber when the IPG is assembled. In the case where the threaded holes are formed in the header body, the anchor screw is installed with a torque limited driver to prevent excess force from being placed on the header. In the case where the header body includes an anchor block, the anchor block allows sufficient axial force to be applied by the anchor screw to the anchor ring to hold it securely in place, without fracturing the header body.

The lead channel is further comprised of ferrule chamber 727 bounded by alignment cylinder 712. The ferrule chamber is coaxial with the lead channel.

Ferrule centering surface 716 is adjacent to and coaxial with alignment cylinder 712 and is designed to hold the ferrule and the optical fiber in optical alignment with the optical axis of the lead channel. Alignment cylinder 712 forms chamfer angle θ, with ferrule centering surface 716. In a preferred embodiment, chamfer angle θ can range from about 135° to about 150°, ±5°. Ferrule centering surface 716 centers and aligns the proximal end of the lead and optical ferrule with buffer gap 734, optical window 718 and composite optoelectronic device 740.

Cylindrical buffer surface 714 is adjacent to and coaxial with ferrule centering surface 716. Cylindrical buffer surface 714 forms buffer gap 734 between the proximal end of the optical ferrule and optical window 718. The buffer gap prevents application of pressure to the optical window from fluid or tissue build up on the ferrule tip or from irregularities of the optical fiber polished surface at the ferrule tip.

Figure 7D:
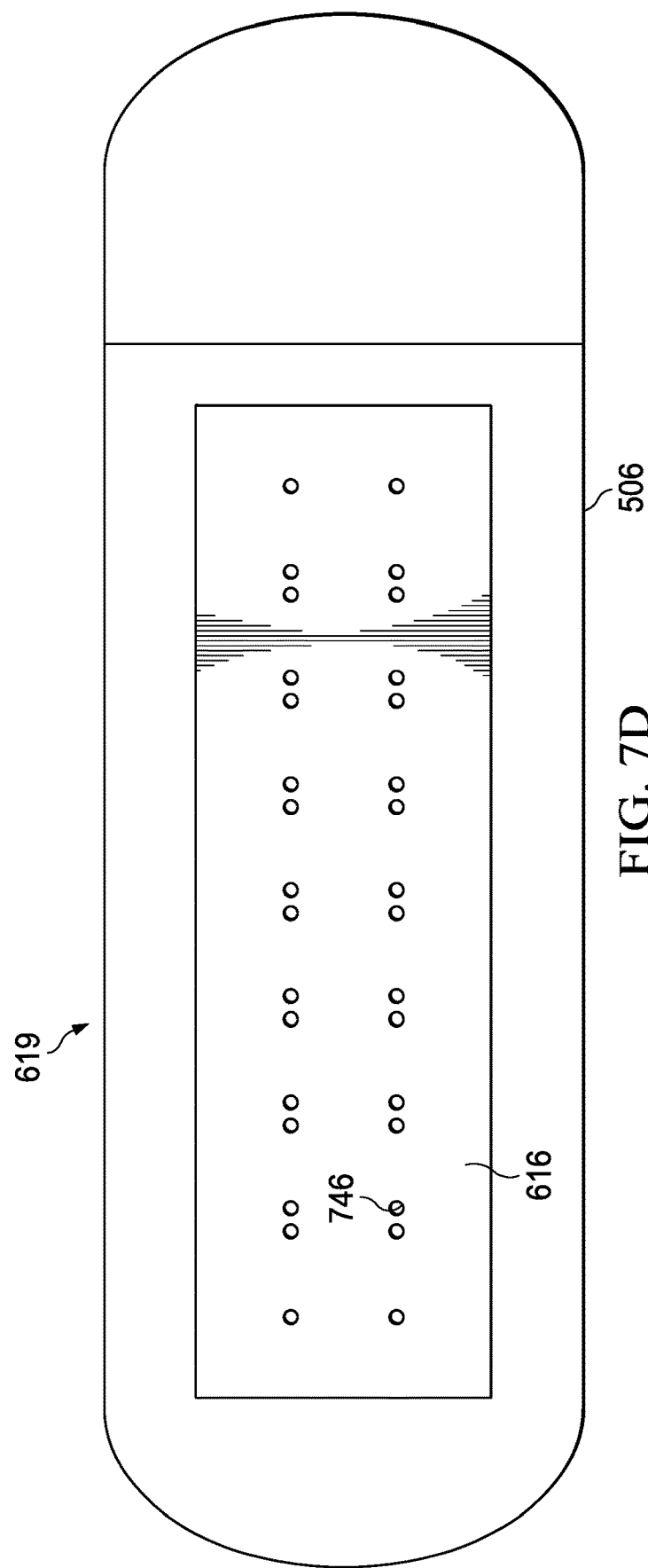
FIG. 7D is a top view of a preferred header bay for an improved IPG device.

Referring then to FIG. 7D, electrical feedthrough plate 616 comprises a flat insulator, preferably a ceramic material, and is fixed at the bottom of header bay 619 by a suitable adhesive, or by ceramic welding. Electrical feedthrough plate 616 is comprised of a plurality of receivers, such as receiver 746. The receivers are connected to the main circuit board, as will be further described. Connector pins 706 at the base of the header body interface with the receivers.

Figure 7E:
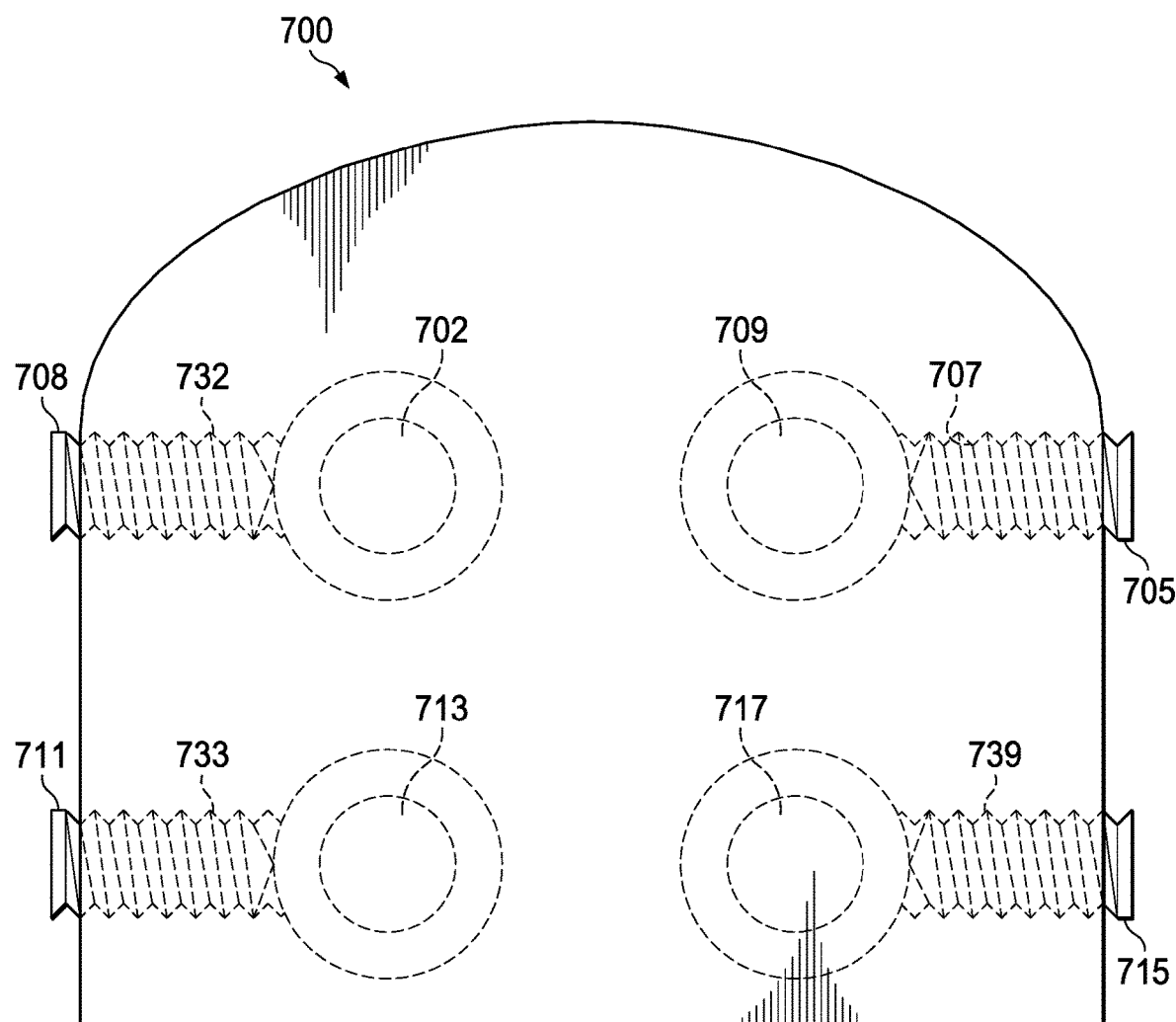
FIG. 7E is a rear view of a header for an improved IPG device.

Referring then to FIG. 7E, in a preferred embodiment, the header is comprised of four lead channels 702, 709, 713, and 717. Each lead channel includes a perpendicularly oriented threaded hole 732, 707, 733 and 739 and anchor screws 708, 705, 711 and 715, respectively.

In the prior art, there is typically an anchor ring, which is engaged by a set-screw to fix the lead contacts within the header. The anchor ring is typically placed distal to the contacts, requiring a separate anchoring block to engage the lead and set-screw. One advantage of this embodiment is that the anchor ring may be positioned proximal to the lead contacts, nearest the end of the lead. This positioning eliminates the need for a separate anchoring block and reduces the size of the IPG casing if threaded holes 732, 707, 733, and 739 are integrated into the header body as may be achieved through injection molding of a ceramic or glass. Further, placement of the anchoring ring nearest the proximal tip of the lead provides mechanical fixation of the lead closest to the optical components, promoting a stable optical signal.

Figure 8:
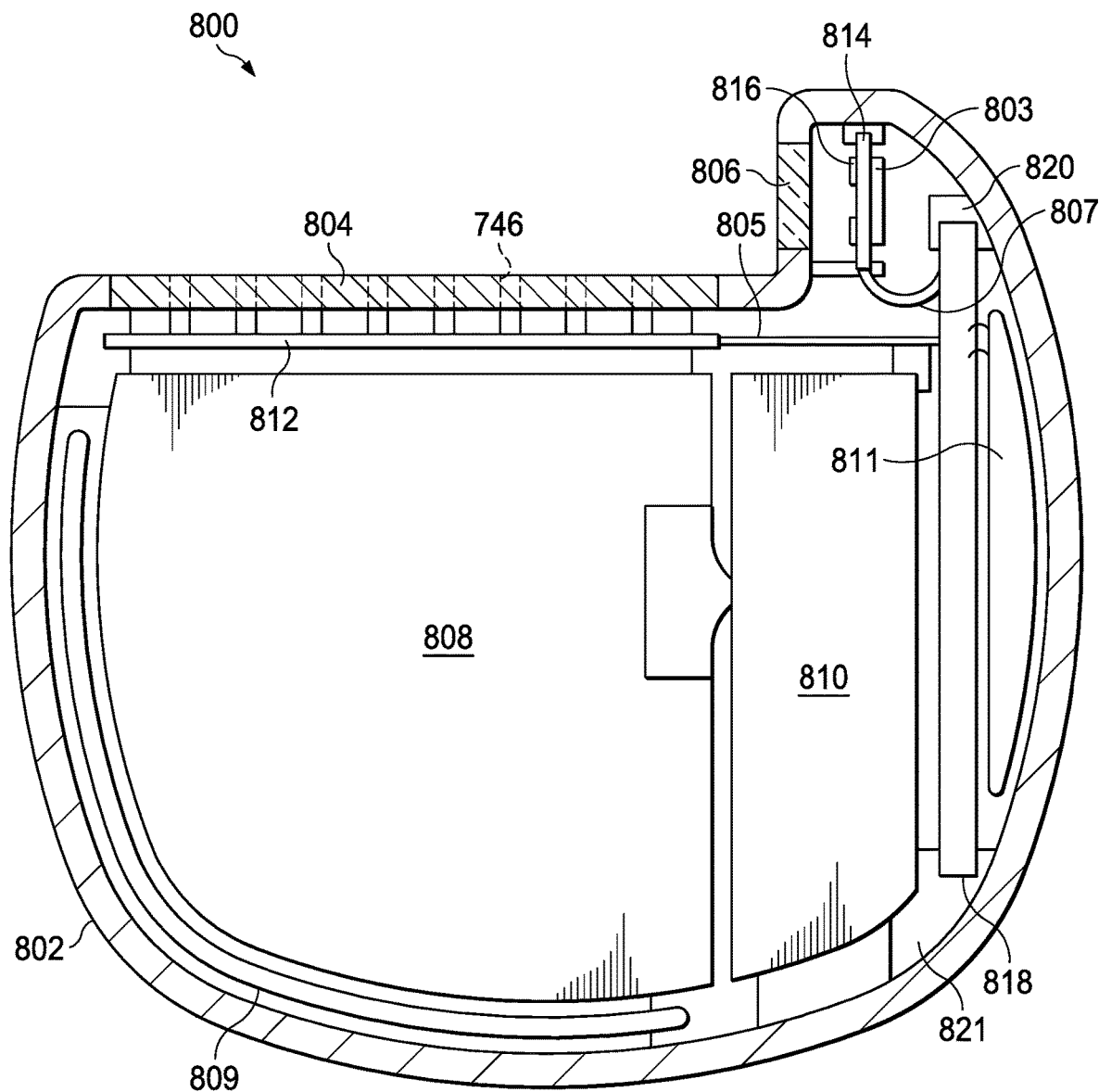
FIG. 8 is a cross-sectional view of a preferred IPG body.

Referring then to FIG. 8, IPG body 800 is further comprised of IPG casing 802, optical window 806, electrical feedthrough plate 804, composite optoelectronic device 816, connector card 812, main circuit board 818, battery 808, and capacitor 810.

The electrical components are secured in the casing with appropriate insulated plastic standoffs, such as standoffs 820 and 821.

Electrical feedthrough plate 804 is hermetically sealed to IPG casing 802, adjacent the header bay. The electrical feedthrough plate is mechanically fixed to connector card 812 and is connected to main circuit board 818 by flexible ribbon cable 805.

Optical window 806 is hermetically sealed to the IPG casing in a position perpendicular to both the electrical feedthrough plate and the lead channels. In a preferred embodiment, optical window 806 is comprised of synthetic sapphire. Synthetic sapphire provides optimal optical properties for transmitting visible red or infrared light between composite optoelectronic device 816 and optical transmission fibers, as will be further described.

Composite optoelectronic device 816 is positioned adjacent the optical window and held in position parallel to the optical window by the daughterboard. The optoelectronic device 816 is also perpendicular to the optical axis of the lead channels. Daughterboard 814 is further comprised of processor 803, as will be further described. Daughterboard 814 is held in position by the standoffs and is connected to main circuit board 818 by ribbon cable 807. The ribbon cable supplies power to the daughterboard and communicates control signals as required.

Main circuit board 818 is positioned in the IPG casing by the standoffs and is operatively connected to the battery, the capacitor, the contacts of the leads and the daughterboard.

Main circuit board 818 receives data input from the daughterboard and generates stimulation pulses which vary in frequency, pulse-width, and amplitude based on signals from the daughterboard. The stimulation pulses are sent to the lead contacts for transmission to the electrodes. The daughterboard generates control signals for the main circuit board by sending light pulses from the light emitters and receiving and interpreting signals from light detectors, as will be further described. The main circuit board is also operatively connected to secondary induction coil 809 and RF antenna 811.

The main circuit board includes processors and radio signal generators which allow it to communicate signals to exterior receiving devices through RF antenna 811. In a preferred embodiment, the main processor and the RF antenna are used to communicate a warning signal from the daughterboard if an emitter current reaches a maximum value, as will be further described.

Capacitor 810 is connected to battery 808 and stores energy from the battery to produce the stimulation pulses. In a preferred embodiment, battery 808 is a lithium-ion rechargeable battery. Battery 808 is inductively charged through secondary induction coil 809 positioned around the battery on one internal surface of the IPG casing. The main circuit board controls the recharging duty cycle.

Figure 9A:
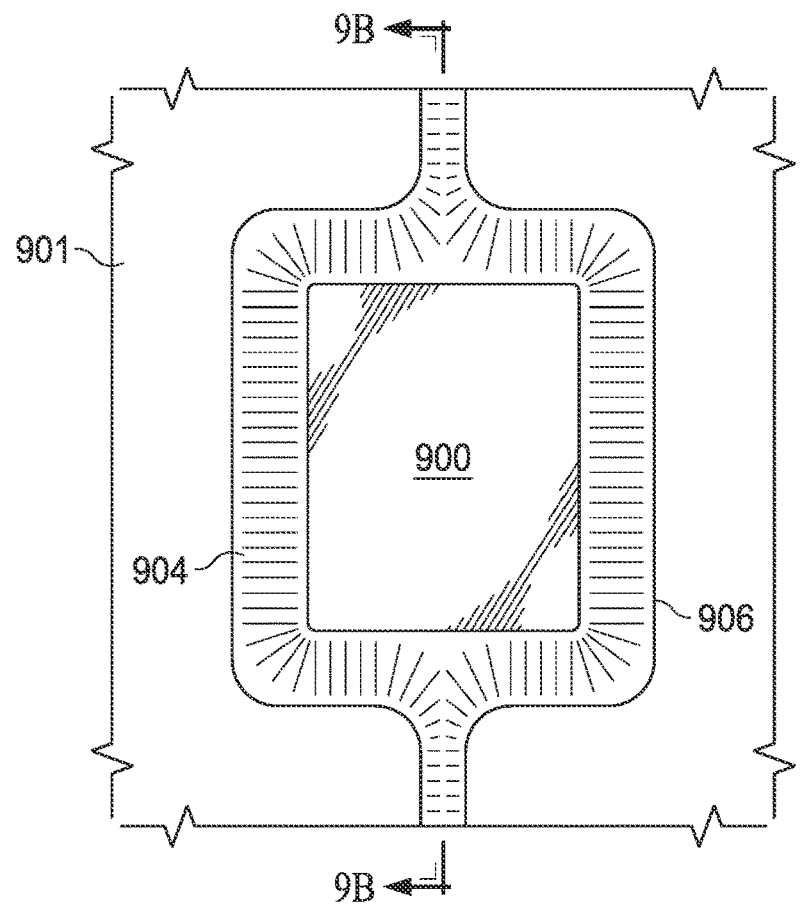
FIG. 9A is a plan view of an optical window for an improved IPG device.
Figure 9B:
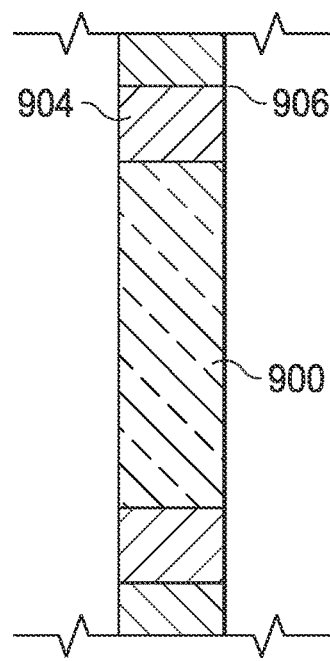
FIG. 9B is a cross-sectional side view of an optical window for an improved IPG device.

Referring then to FIGS. 9A and 9B, in a preferred embodiment, optical window 900 is a polished rectangle single crystal alumina (sapphire) or polycrystalline alumina ceramic. It is joined to IPG case 901 in the header bay by ceramic brazing. Niobium is used as a metal to ceramic filler material. In a preferred embodiment the alumina is 94% brazed to Fe-29Ni-10Co internally at approximately 1000° C. Optical window 900 is brazed to IPG case 901 along window braze junction 906 using hermetic braze fillet 904.

In FIG. 9B, optical window 900 and IPG case 901 are shown as coplanar, but these may alternatively be stacked or overlaid.

Figure 10A:
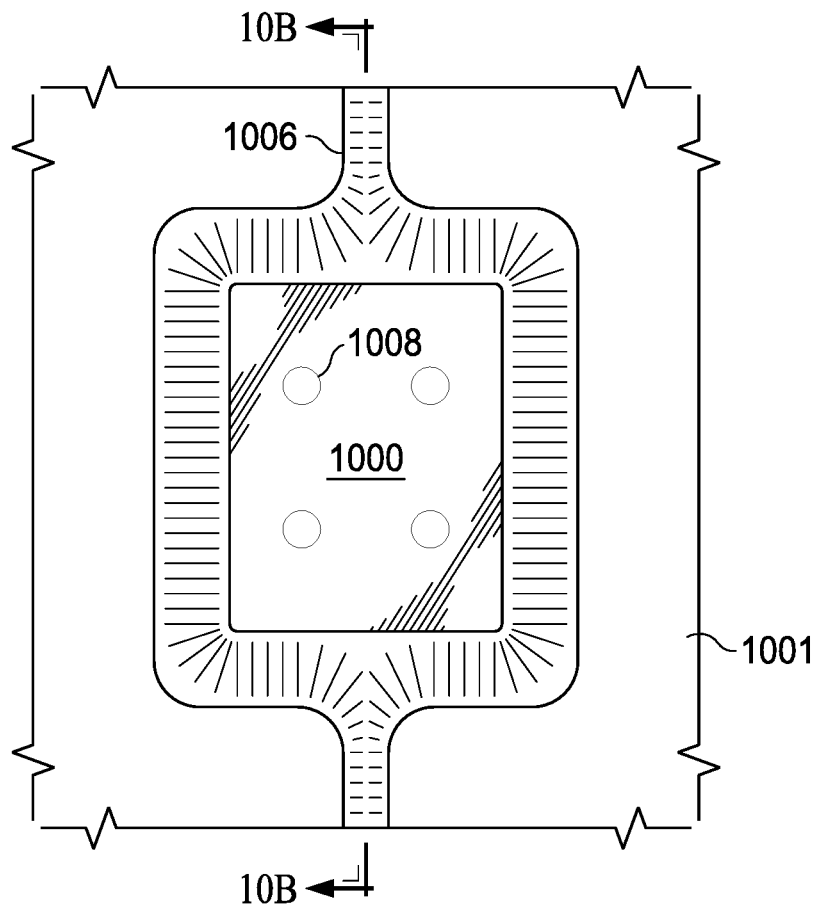
FIG. 10A is a plan view of an optical window for an improved IPG device.
Figure 10B:
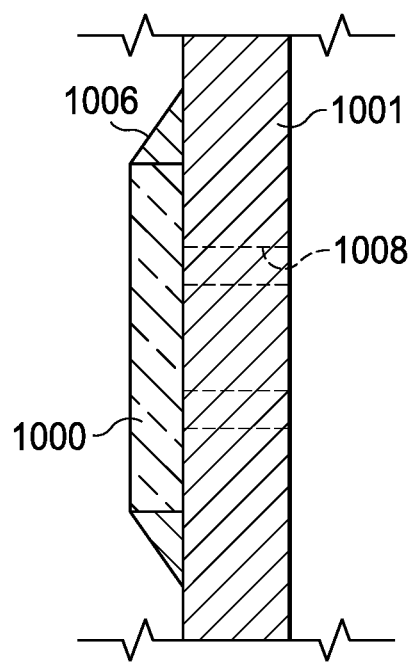
FIG. 10B is a cross-sectional side view of an optical window for an improved IPG device.
Figure 11A:
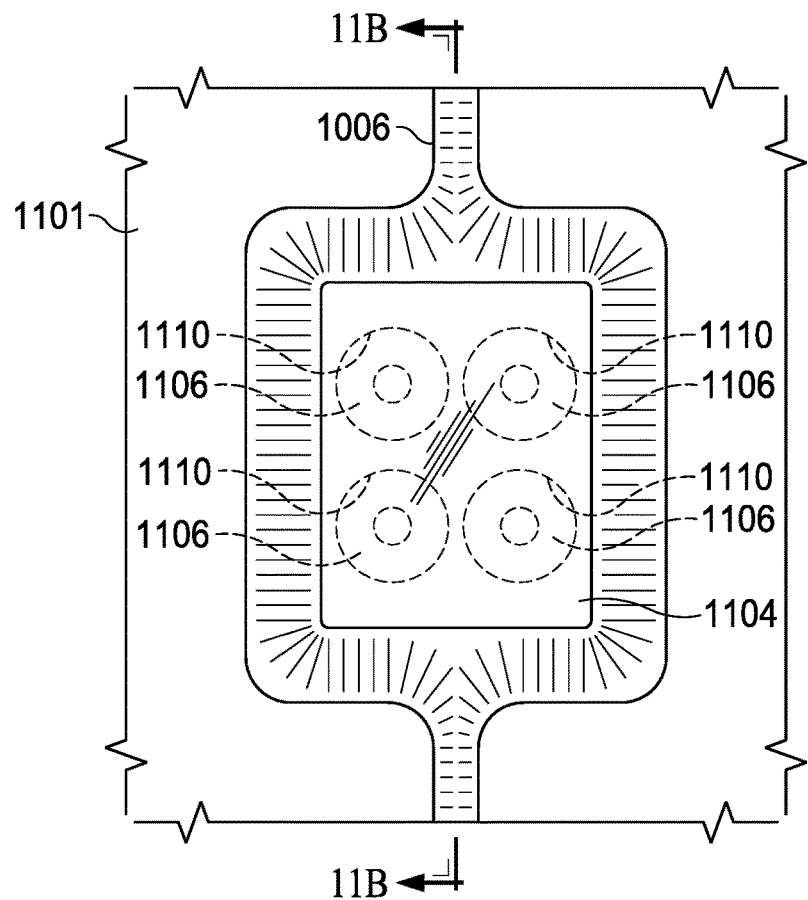
FIG. 11A is a plan view of an optical window for an improved IPG device.
Figure 11B:
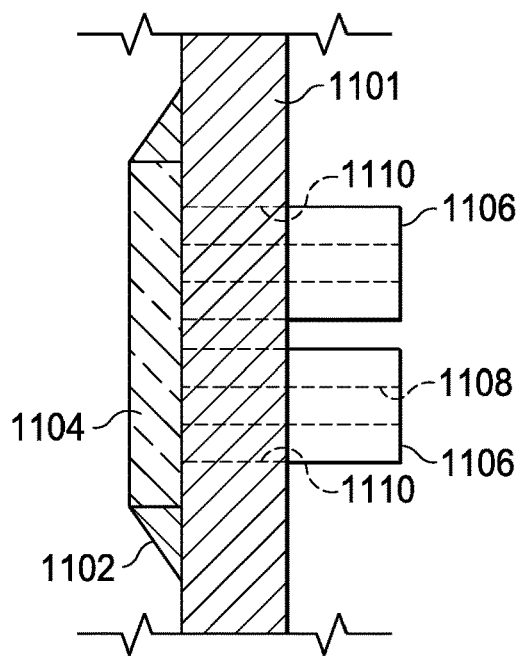
FIG. 11B is a cross-sectional side view of an optical window for an improved IPG device.
Figure 11C:
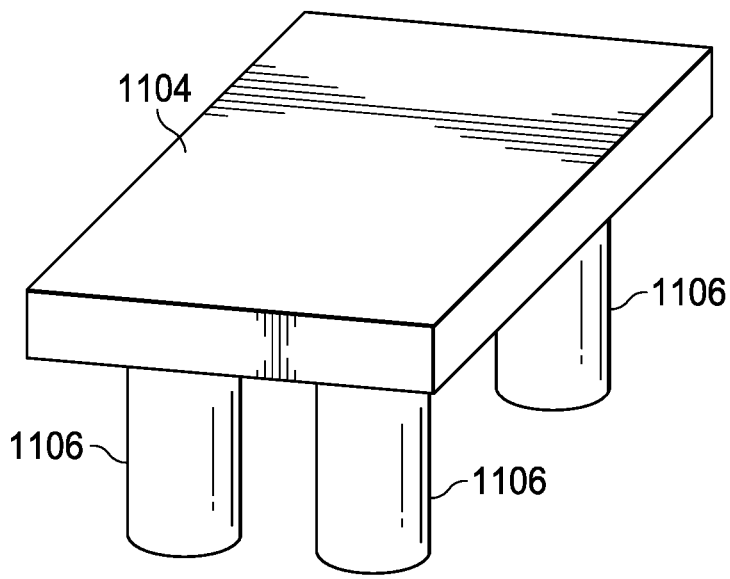
FIG. 11C is an isometric view of an optical window for an improved IPG device.
Figure 11D:
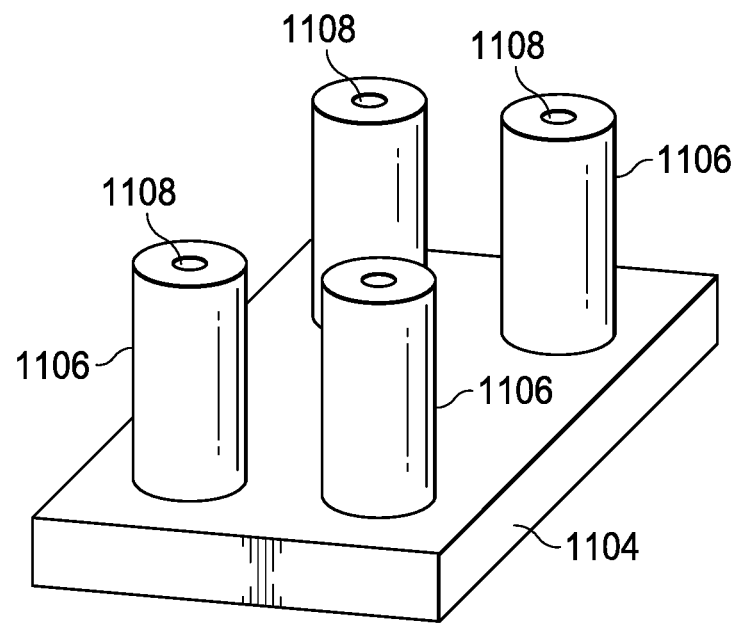
FIG. 11D is an isometric view of an optical window for an improved IPG device.

Referring then to FIGS. 10A and 10B, in another embodiment, optical window 1000 is overlaid on the outside of IPG case 1001, adjacent the header bay. In this embodiment, IPG case 1001 includes four (4) waveguides 1008. The waveguides are holes in the header bay wall that allow red or infrared light to be transmitted through the optical window, along the optical axis of each lead channel and into the interior of the IPG casing. Optical window 1000 is hermetically sealed to IPG case using brazing, soldering, epoxy or other suitable means along window junction 1006.

Referring then to FIGS. 11A, 11B, 11C and 11D, in another preferred embodiment, window plate 1104 comprises a flat sapphire rectangle about 1 mm thick. Four optical wave guides, 1106 are fused to the window plate using ceramic welding. In another embodiment, the window plate and optical waveguides are integrally formed from the same crystal structure. Each optical wave guide includes an internally reflective iris 1108. The iris is a cylindrical hole which is concentrically aligned with the optical axis of a lead channel. Window plate 1104 is laser welded to IPG casing 1101 along weld joint 1102.

When assembled, each of the optical wave guides passes through holes 1110 and into the interior of the IPG casing. In a preferred embodiment, each optical wave guide abuts an optoelectronic device on the daughterboard secured in the IPG casing, as previously described. In practice, the iris is important because it prevents light loss between the optical fiber in the lead and the optoelectronic devices.

Referring then to FIGS. 12A, 12B, and 12C, daughterboard 814 is preferably a 2-sided PC board supporting optoelectronic devices 1204, 1205, 1206, and 1207, connector 1210, and processor 1208. Processor 1208 draws power from the battery and is supplied with an onboard memory that contains instructions for its operation. The optoelectrical devices are positioned in quadrants adjacent the proximal surface of the optical window. Each quadrant is separated by an optical opaque light baffle 1212. In a preferred embodiment, the baffle is a "cross-shaped" PVC standoff, approximately 1-2 mm in height, coated with a reflective layer, such as $TiO_2$, on its exterior surface and bonded to the daughterboard with a suitable adhesive. Each of the optoelectronic devices is positioned to be perpendicular to and aligned with the optical axis of one lead channel in order to maximize either transmission or reception of light from an optical fiber, positioned in the lead channel. In a preferred embodiment, optoelectronic devices 1204, 1205, 1206, and 1207 and light baffle 1212 may be integrated into one or more application specific integrated circuits (ASIC s).

Connector 1210 links daughterboard 814 to the main circuit board of the IPG device. Processor 1208 is electrically connected to the optoelectronic devices through the daughterboard as required to communicate electrical signals to the processor.

In one embodiment, optoelectronic device 1204 is an optical emitter and optoelectronic devices 1205, 1206, and 1207 are optical detectors.

In another embodiment, optoelectronic devices 1204, and 1206 are optical emitters and optoelectronic devices 1205, and 1207 are optical detectors.

The wavelengths of the emitters may range from visible red to infrared, or approximately 620-1700 nanometers. The emitter(s) may be either single wavelength or multiple wavelengths. For instance, the emitter could be a high-speed, single wavelength infrared emitting diode of 850 nm wavelength, such as part no. VSMY1850 available from Vishay Intertechnology, Inc. of Malvern, Pennsylvania. Alternatively, the emitter could be a multi-chip emitter, such as product no. MTMD6788594SMT6 available from Marktech Optoelectronics, Inc., of Latham, New York, which is capable of emitting wavelengths 670 nm, 770 nm, 810 nm, 850 nm, and 950 nm. Alternatively, an emitter and detector may be integrated into a single ASIC such as with the ADPD144RI from Analog Devices, Inc. of Norwood, Massachusetts.

Figure 12D:
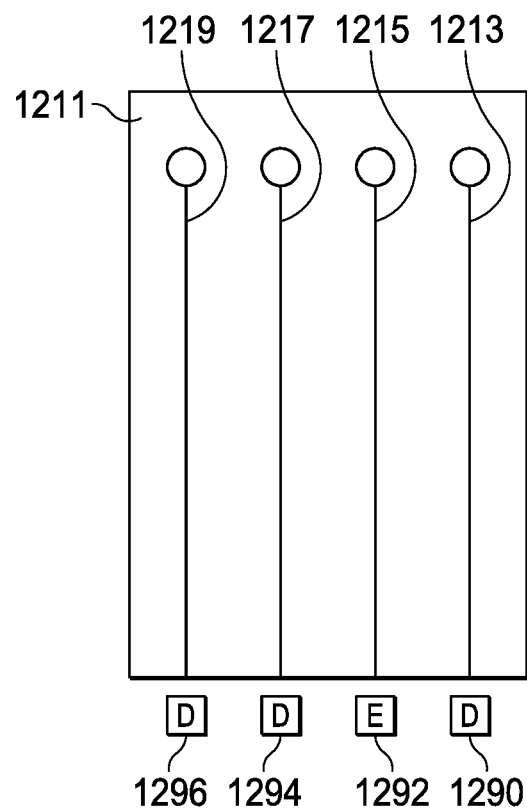
FIG. 12D is a schematic of an optical signal for an improved IPG device.

Referring to FIG. 12D, a preferred embodiment of a coupling arrangement between optical leads and optical emitters in a surgical lead will be described. Emitter 1292 is optically coupled to central fiber 1215 of surgical lead 1211. Detector 1290 is optically coupled to lead 1213 of surgical lead 1211. Detectors 1294 and 1296 are connected to leads 1217 and 1219, respectively.

Figure 12E:
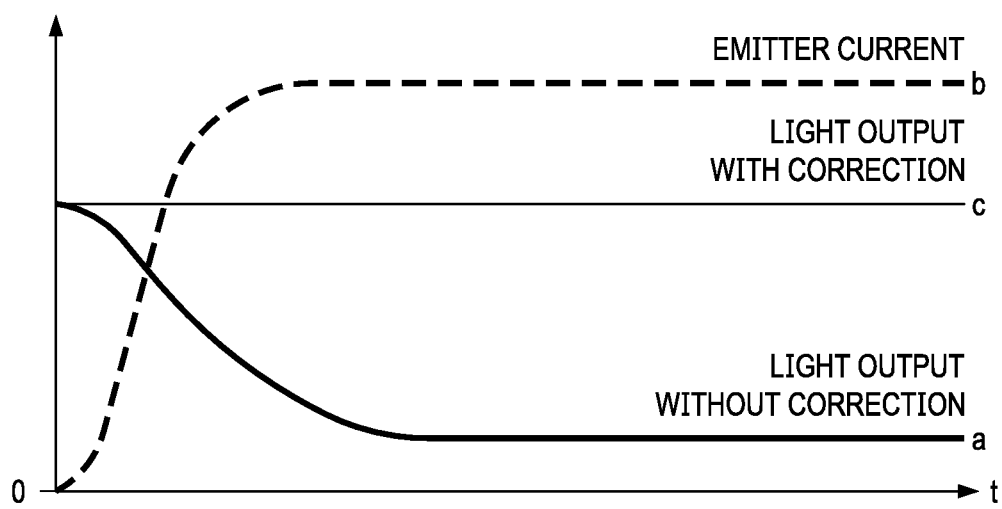
FIG. 12E is a graphical depiction of the advantages of a lead configuration.

Referring to FIG. 12E, a graph showing light output from a side firing fiber of a surgical lead and input current to a corresponding emitter over time, will be described.

Light output over time is shown by the curve labeled "a". It can be seen that the light output of fiber 1215 degrades over time due to microfractures in the fiber and other degradation of optical components in the surgical lead. The decrease in optical performance of fiber 1215 is monitored over time by processor 1208 by reading the voltage signal from detector 1296, which receives light from fiber 1215 reflected by the spinal cord. Processor 1208 is programmed to compensate for the degradation in light output by increasing the current to emitter 1204 according to curve "b". As can be seen, increasing the current to emitter 1204 maintains the light output of fiber 1215 at a consistent level shown by curve "c" as shown in the drawing.

Figure 12F:
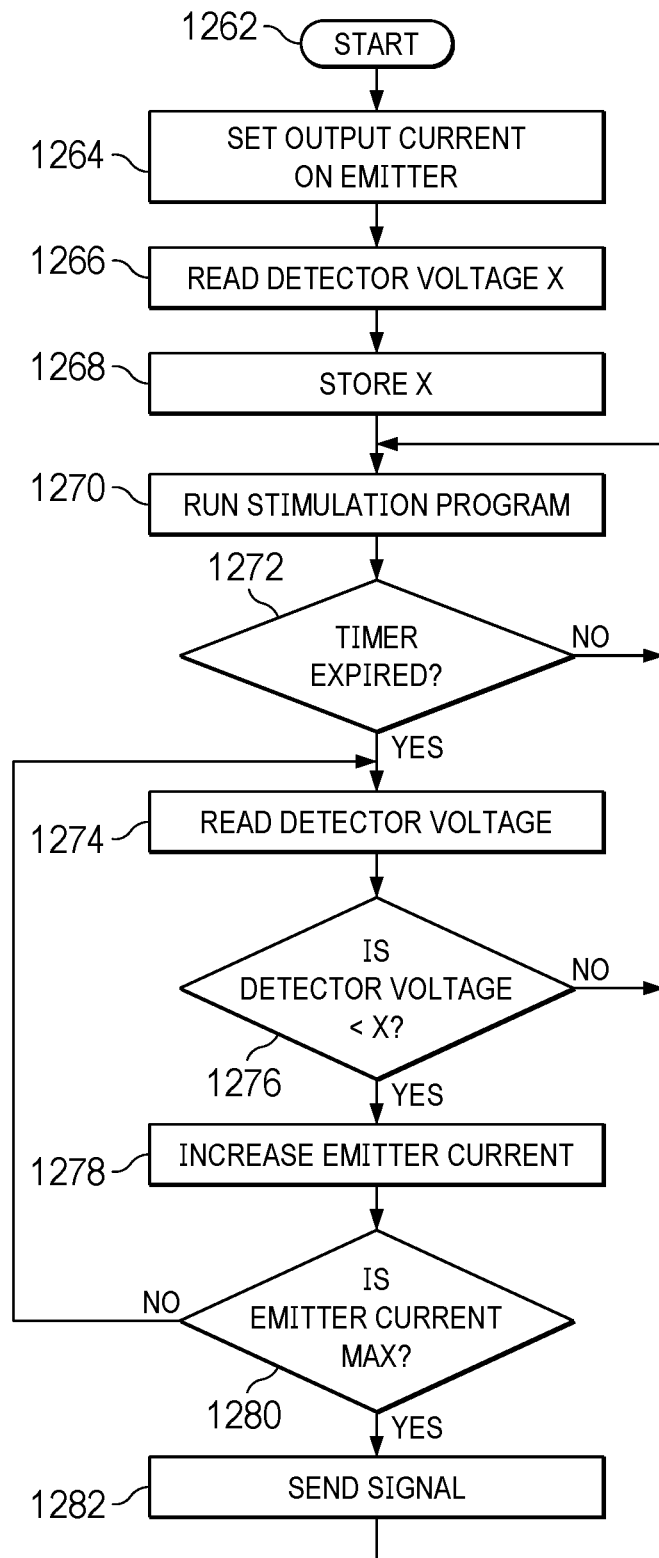
FIG. 12F is a method diagram for calculating stimulation.

Referring to FIG. 12F, a self-adjusting emitter current program for adjusting light output from an emitter fiber will be described. In a preferred embodiment, the program is a series of instructions that reside in the memory of processor 1208.

At step 1262, the program begins.

At step 1264, the processor sets the output current to emitter 1292. In a preferred embodiment, the emitter current is set to the minimum requirement to generate a readable signal at detectors 1290 and 1296.

At step 1266, the processor reads the voltage at detector 1294. At step 1268, the voltage level is stored in memory. At step 1270, processor 1208 sends a signal to main circuit board 818 to initiate a stimulation program. The main circuit board responds by sending appropriate stimulation signals to the leads.

At step 1272, processor 1208 determines whether or not a self-timer has expired. If so, the program proceeds to step 1274. If not, the program returns to step 1270.

At step 1274, processor 1208 reads the detector voltage at detector 1294.

At step 1276, the processor compares the present value detector voltage to the stored detector voltage in memory. If the present value detector voltage is less than the stored detector voltage, then the process moves to step 1278. If not, the program returns to step 1270.

At step 1278, processor 1208 increases the emitter current to emitter 1204. In a preferred embodiment, the emitter current is increased by $1/100$ of the maximum emitter current permitted.

At step 1280, the processor determines whether or not the emitter current is set to the maximum allowed. If so, the program moves to step 1282. If not, the program returns to step 1274.

At step 1282, the processor sends a signal to the main circuit board, which communicates it through the RF antenna to an external receiver, indicating that the maximum emitter current has been reached. The program then returns to step 1270.

Figure 12G:
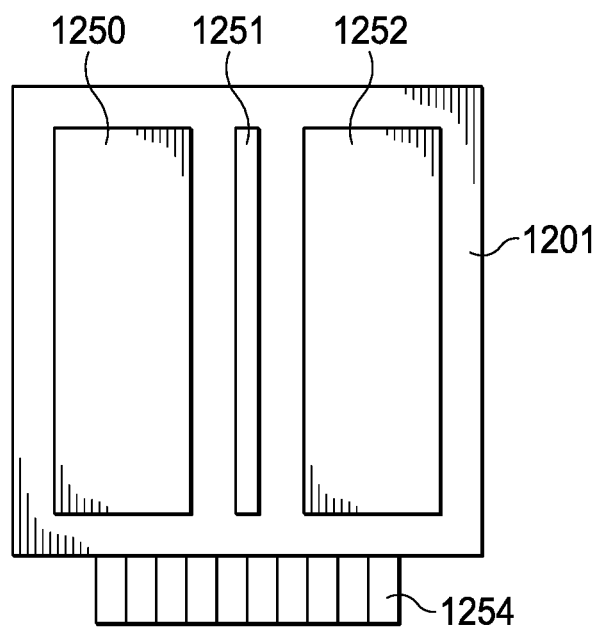
FIG. 12G is a front view of a daughterboard for an improved IPG device.
Figure 12H:
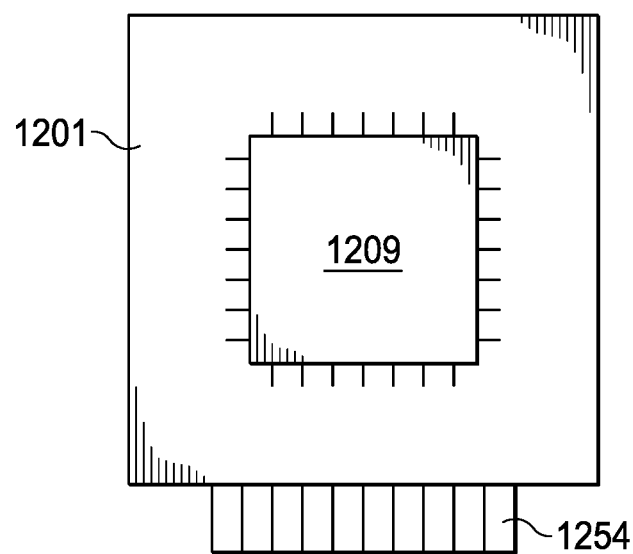
FIG. 12H is a rear view of a daughterboard for an improved IPG device.
Figure 12I:
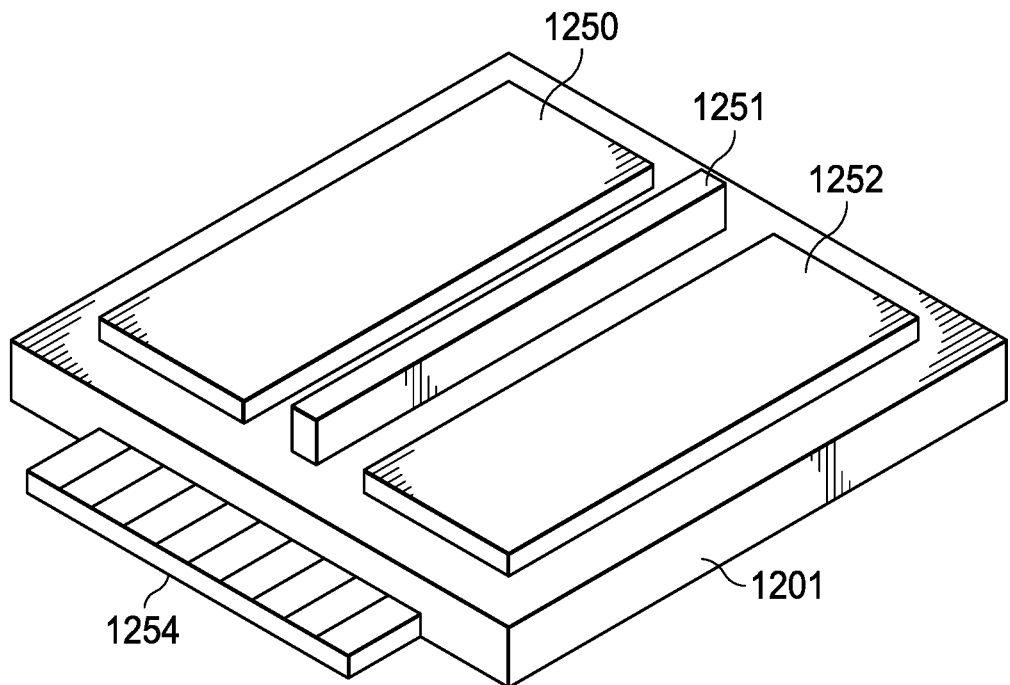
FIG. 12I is an isometric view of a daughterboard for an improved IPG device.

Referring then to FIGS. 12G, 12H, and 12I alternate embodiment of daughterboard 814 will be further described.

Daughterboard 1201 is a composite optoelectrical device comprised of optoelectronic devices 1250, and 1252, connector 1254, and signal processor 1209. The optoelectrical devices are positioned adjacent and parallel to the optical window. In a preferred embodiment, each optoelectronic device is separated by an optical opaque light baffle 1251. In a preferred embodiment, baffle 1251 is a reflective or opaque rectangular PVC standoff bonded to the daughterboard, as previously described.

Connector 1254 links daughterboard 1201 to the main circuit board of the IPG device. Processor 1209 is electrically connected to the optoelectronic devices through the daughterboard as required and communicates external signals to the signal processor. The daughterboard communicates to the main circuit board through connector 1254.

Figure 12J:
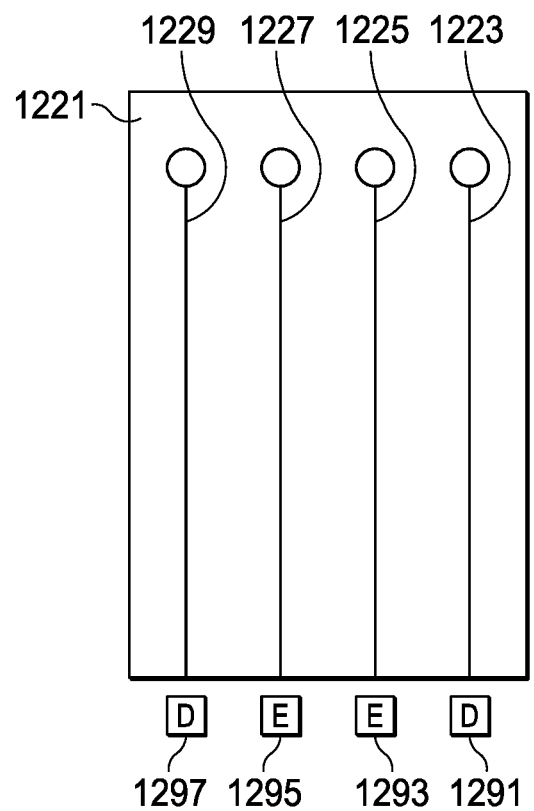
FIG. 12J is a schematic of an optical signal for an improved IPG device.

Referring then to FIG. 12J, a preferred embodiment of a coupling arrangement between optical leads and optical emitters in a surgical lead will be described. Emitter 1293 is optically coupled to central fiber 1225 of signal lead 1221. Detector 1291 is optically coupled to lead 1223 of signal lead 1221. Emitter 1295 is optically coupled to central fiber 1227 and detector 1297 is connected to lead 1229. In this configuration, dual optical reflectometry channels facilitate the stereoscopic detection of spinal cord position in the sagittal and coronal planes as previously described in U.S. Pat. Nos. 8,239,038; 8,543,213; 9,132,273; 9,656,097 to Wolf II, incorporated herein by reference.

Referring to FIGS. 13A-13G, a preferred embodiment of percutaneous lead 1400 is described.

Figure 13A:
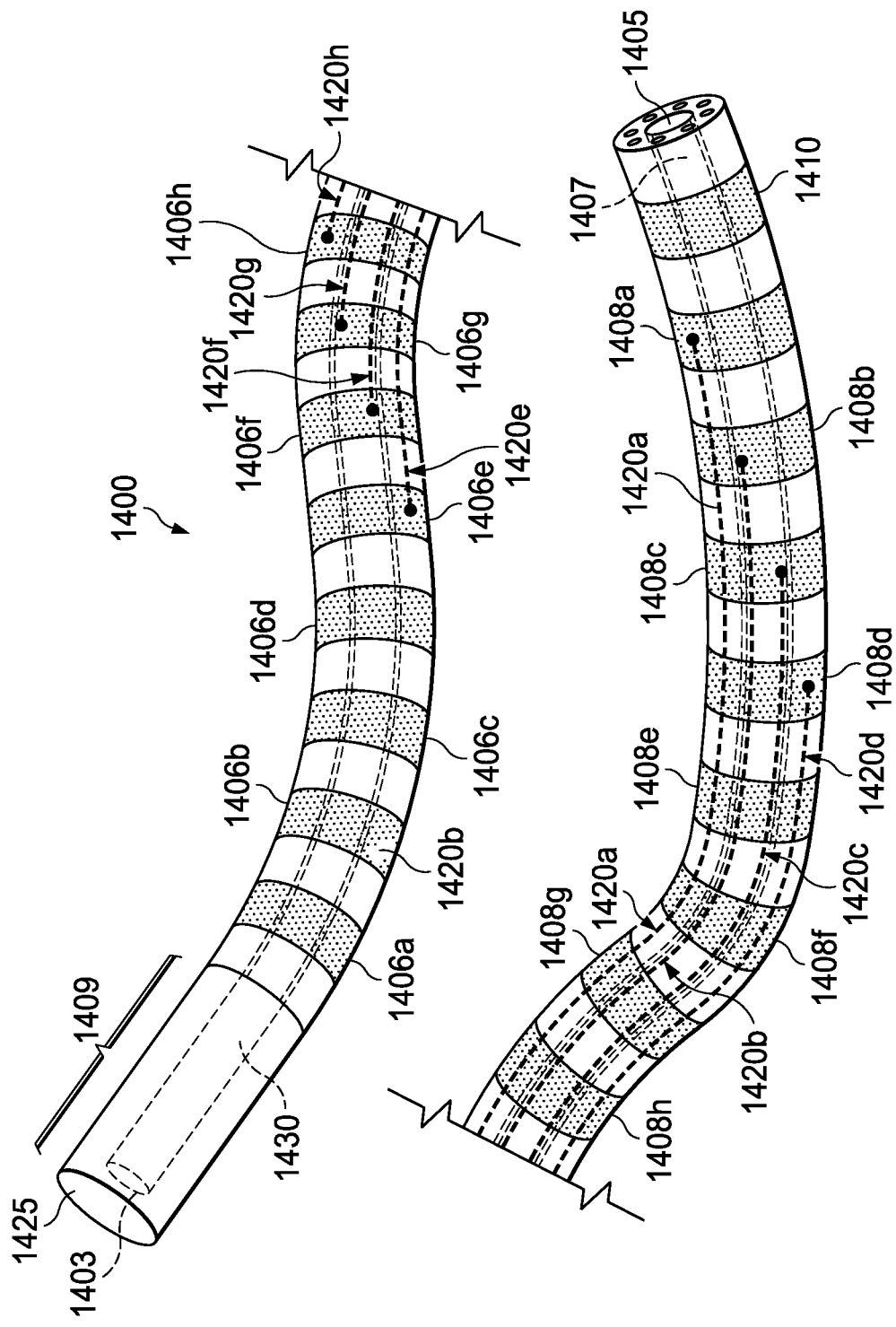
FIG. 13A is a side view of a preferred embodiment of subcutaneous leads.
Figure 13B:
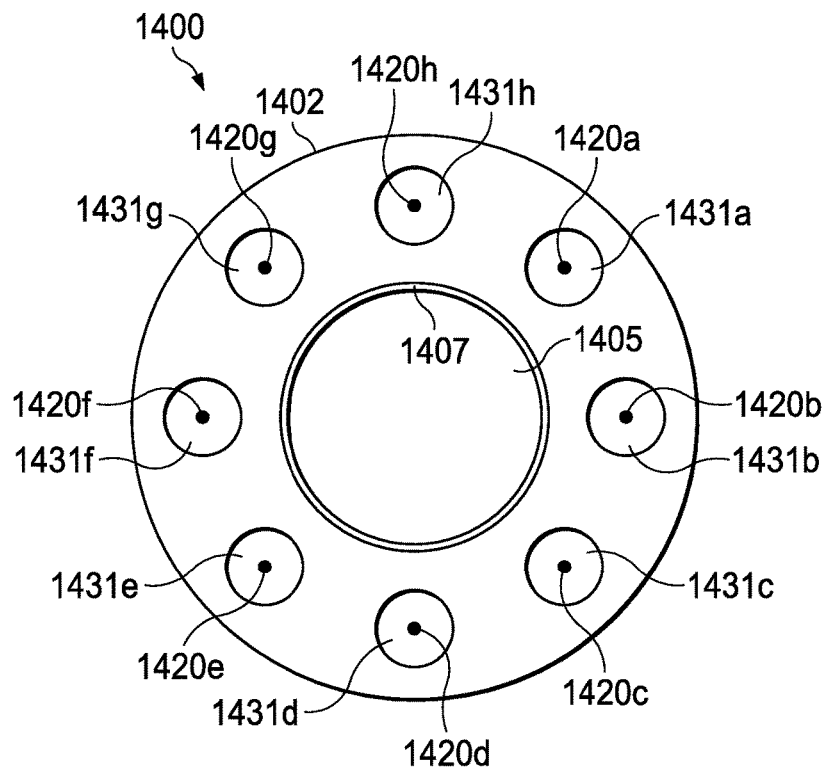
FIG. 13B is a cross-sectional view of a preferred embodiment of subcutaneous leads.

Referring then to FIGS. 13A and 13B, in a preferred embodiment of lead body 1402 is comprised of a generally hollow tube terminated by transmission window 1409. In a preferred embodiment, the lead body is comprised of a flexible polymer such as Pellethane 55-D, or similar biocompatible polymer. The lead body is preferably a multilumen extrusion available from Zeus Industrial Products, Inc. of Orangeburg, South Carolina.

Transmission window 1409 is a hollow cylinder fused to the terminus of the flexible lead body enclosing diffuser cavity 1430. In a preferred embodiment, the window is a suitable optically transparent material such as thermoplastic polyurethane. Transmission window 1409 is terminated by cap 1425. Cap 1425 includes internally reflective surface 1403 which faces into diffuser cavity 1430. In a preferred embodiment, the internally reflective surface is a titanium dioxide coating.

Stylet channel 1405 extends from the transmission window to the proximal end of the lead body. The stylet channel serves the dual purposes of housing a guide stylet for use during placement of the lead during surgery, and housing and optical fiber after surgery, as will be further described. In a preferred embodiment, stylet channel 1405 is lined with polytetrafluoroethylene (PTFE) lining 1407 which extends from the length of the lead body up to transmission window 1409. The extremely low surface friction afforded by the carbon-fluorine bonds of the PTFE facilitates manual insertion of the stylet and the optical fiber. The lining does not extend into the diffuser cavity, where the side-firing segment of the optical transmission fiber resides, to enhance optical transmission.

Metallic anchor ring 1410 is positioned at the proximal end of the lead body. The anchor ring is generally cylindrical and is permanently affixed to the exterior of the lead body proximal to the lead contacts. Eight cylindrical proximal metallic contacts 1408*a*, 1408*b*, 1408*c*, 1408*d*, 1408*e*, 1408*f*, 1408*g*, 1408*h* are fixed to the exterior of the lead body at even axial distances along the lead body and positioned to electrically contact the coil springs in the header.

In the same way, eight cylindrical distal metallic electrodes 1406*a*, 1406*b*, 1406*c*, 1406*d*, 1406*e*, 1406*f*, 1406*g*, 1406*h* are provided at the distal end of the lead body. The distal lead contacts are each and permanently fixed to the exterior surface of the lead. The distal lead contacts are evenly spaced along the lead body proximal to the optical window.

The lead body further comprises eight radially oriented lumens 1431*a*, 1431*b*, 1431*c*, 1431*d*, 1431*e*, 1431*f*, 1431*g* and 1431*h*. Conductors 1420*a*, 1420*b*, 1420*c*, 1420*d*, 1420*e*, 1420*f*, 1420*g*, 1420*h* are located in the lumens and extend from respective proximal contacts to distal electrodes. In a preferred embodiment the conductors are comprised of MP35N, or another conductive material similarly resistant to corrosion. Each of the conductors connects exactly one proximal contact to a single paired distal electrode.

Figure 13C:
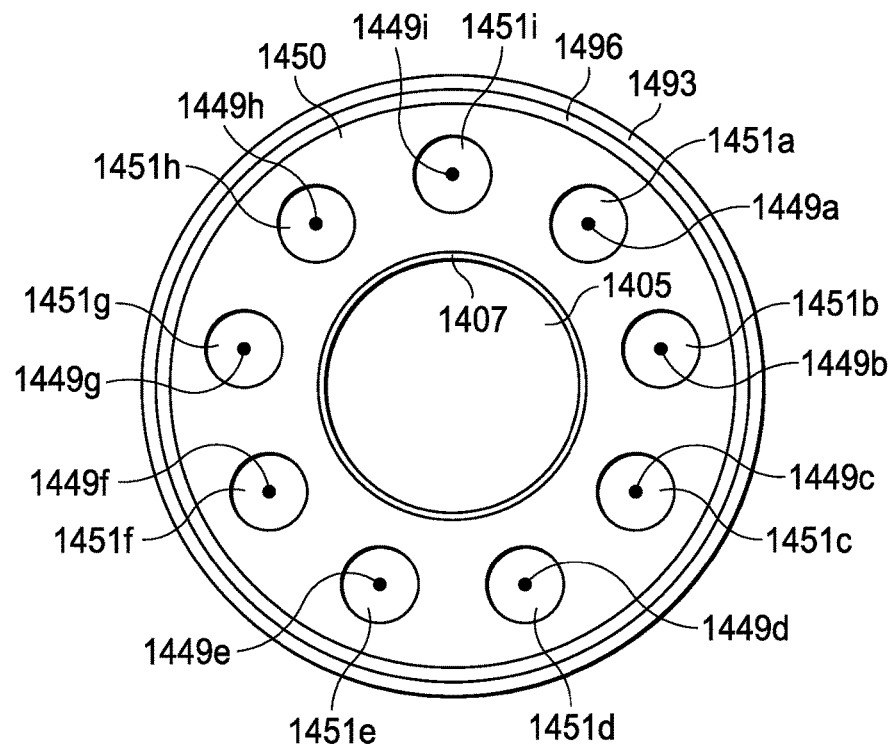
FIG. 13C is a cross-sectional view of an alternative embodiment of subcutaneous leads.

Referring then to FIG. 13C, a cross-sectional view of an alternate embodiment of lead body 1450, is described.

Lead body 1450 comprises nine radially oriented lumens, 1449*a*, 1449*b*, 1449*c*, 1449*d*, 1449*e*, 1449*f*, 1449*g*, 1449*h* and 1449*i*. Conductors 1451*a*, 1451*b*, 1451*c*, 1451*d*, 1451*e*, 1451*f*, 1451*g* and 1451*h* and ground line 1451*i* are located in the lumens. Ground line 1451*i* extends from the proximal end of the lead body to the transmission window. Ground line 1451*i* is electrically connected to anchor ring 1410. When the anchor screw engages anchor ring 1410, the ground lead is connected directly to the IPG ground either through the anchor block or through a ground connection through the header. The ground line may be used to supplement electrical shielding of the electrode array contacts for better MRI compatibility.

In another preferred embodiment, the lead body may incorporate non-metallic shielding layer 1496, connected to ground line 1451*i*, to further enhance MRI capability. In a preferred embodiment, the shielding layer is formed by carbon fibers infused into the surface of the lead body. In another preferred embodiment, low friction layer 1493, such as PTFE, is included on the exterior of the lead body to aid in placement of the lead during surgery.

Figure 13D:
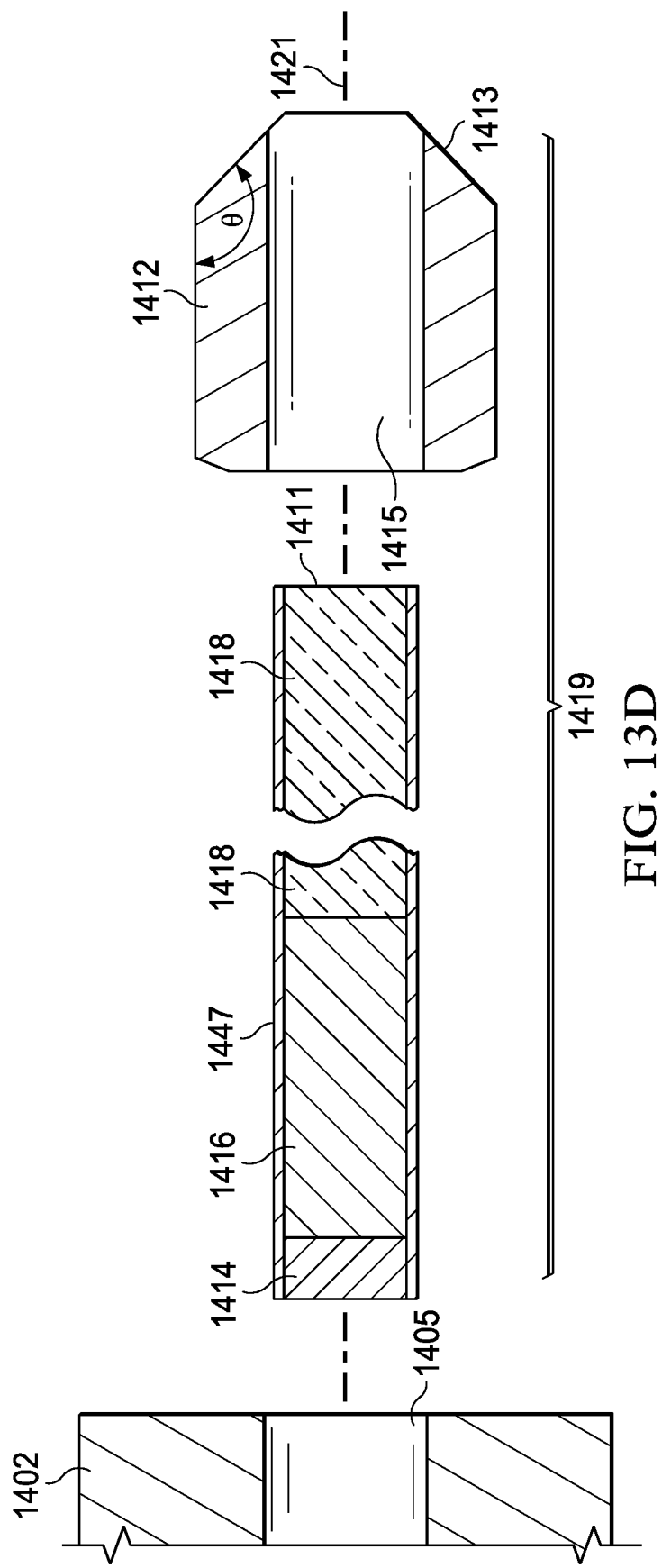
FIG. 13D is an exploded side view of an optical fiber and ferrule configuration.
Figure 13E:
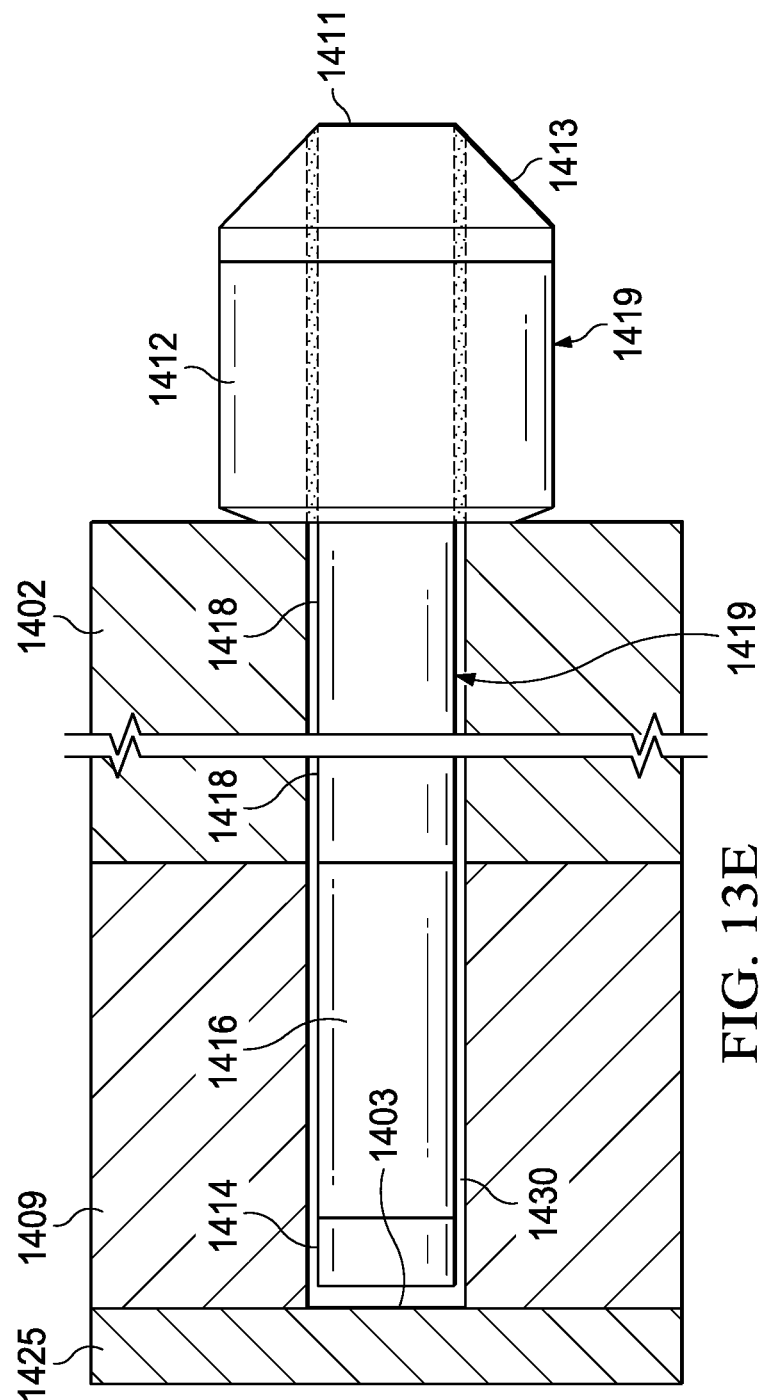
FIG. 13E is a side view of a preferred embodiment of an optical fiber and ferrule assembly.

Referring then to FIGS. 13D and 13E, optical fiber subassembly 1419 includes ferrule 1412 and optical fiber 1418.

Ferrule 1412 is generally a ceramic cylinder. Ferrule 1412 includes integrally formed alignment tip 1413. Alignment tip 1413 is a chamfer formed in the ferrule with a chamfer angle of θ, preferably is between about 135° and 150°. In a preferred embodiment, chamfer angle θ matches the chamfer angle 735 of centering surface 716, so that when the ferrule is mounted in the header there is an elastic compression of the ferrule by the polymer lead body. When mounted, the positive stop of the ferrule by ferrule centering surface 716 prevents pressure being applied to sealed optical window 718 by the fiber or the ferrule. Hole 1415 is centered in ferrule 1412 and extends through the length of the ferrule. In a preferred embodiment, the diameter of the hole closely matches the diameter of the optical fiber. In a preferred embodiment, ferrule 1412 is made of a polished ceramic, preferably zirconia, or other MRI compatible material.

Ferrule 1412 is positioned at the proximal end of optical fiber 1418. Optical fiber 1418 includes end reflector 1414 and side-firing fiber segment 1416 at its distal end and polished optical tip 1411 at its proximal end. Optical fiber 1418 is preferably comprised of a polymethylmethacrylate core with a fluorocarbon cladding of about 250-400 micrometers in diameter. In a preferred embodiment, the fiber also includes a low friction layer 1447, preferably comprised of PTFE. In use, the low friction layer aids in insertion of the fiber in the stylet lumen.

Optical fiber 1418 includes reflector 1414 at its distal end. The reflector prevents axial light emission from the fiber and improves radial dispersion of light. The reflector thereby improves optical signal strength and lowers power consumption. Ideally, the reflector is comprised of a titanium dioxide layer coated on the end of the fiber after it has been thermally polished.

Side-firing fiber segment 1416 is positioned in diffuser cavity 1430, adjacent cap 1425, and is typically about 5 mm in length. Side-firing fiber segment 1416 is formed by modification of the cladding of the optical fiber. The cladding may be modified by using femtosecond laser etching, mechanical abrasion, or an alternative method to achieve radial leakage of light.

Polished optical tip 1411 is positioned at the proximal end of the optical fiber. Polished optical tip 1411 is preferably a thermally polished surface perpendicular to the optical axis of the fiber. Optionally, a convex lens may be attached to the proximal end of the fiber to focus light into or out of the fiber, as will be further described.

Referring then to FIG. 13E, optical fiber subassembly 1419 is positioned in stylet channel 1405. The outer diameter of ferrule 1412 is less than the outer diameter of lead body 1402 but greater than the diameter of stylet channel 1405, such that the lead body acts as a stop for the ferrule.

In one embodiment, optical fiber subassembly 1419 is placed in the stylet channel after surgical placement of the lead body in vivo, as will be further described.

In another embodiment, the fiber subassembly is prefabricated into the lead body. In this embodiment, the proximal end of the optical fiber is secured to the fiber by a suitable adhesive. One such suitable medical grade adhesive is preferably an optically transparent biocompatible epoxy seal, such as EPO-TEK® MED-353ND by Epoxy Technology, Inc. of Billerica, Massachusetts. In this case, polished optical tip 1411 is polished flush with alignment tip 1413.

Figure 13F:
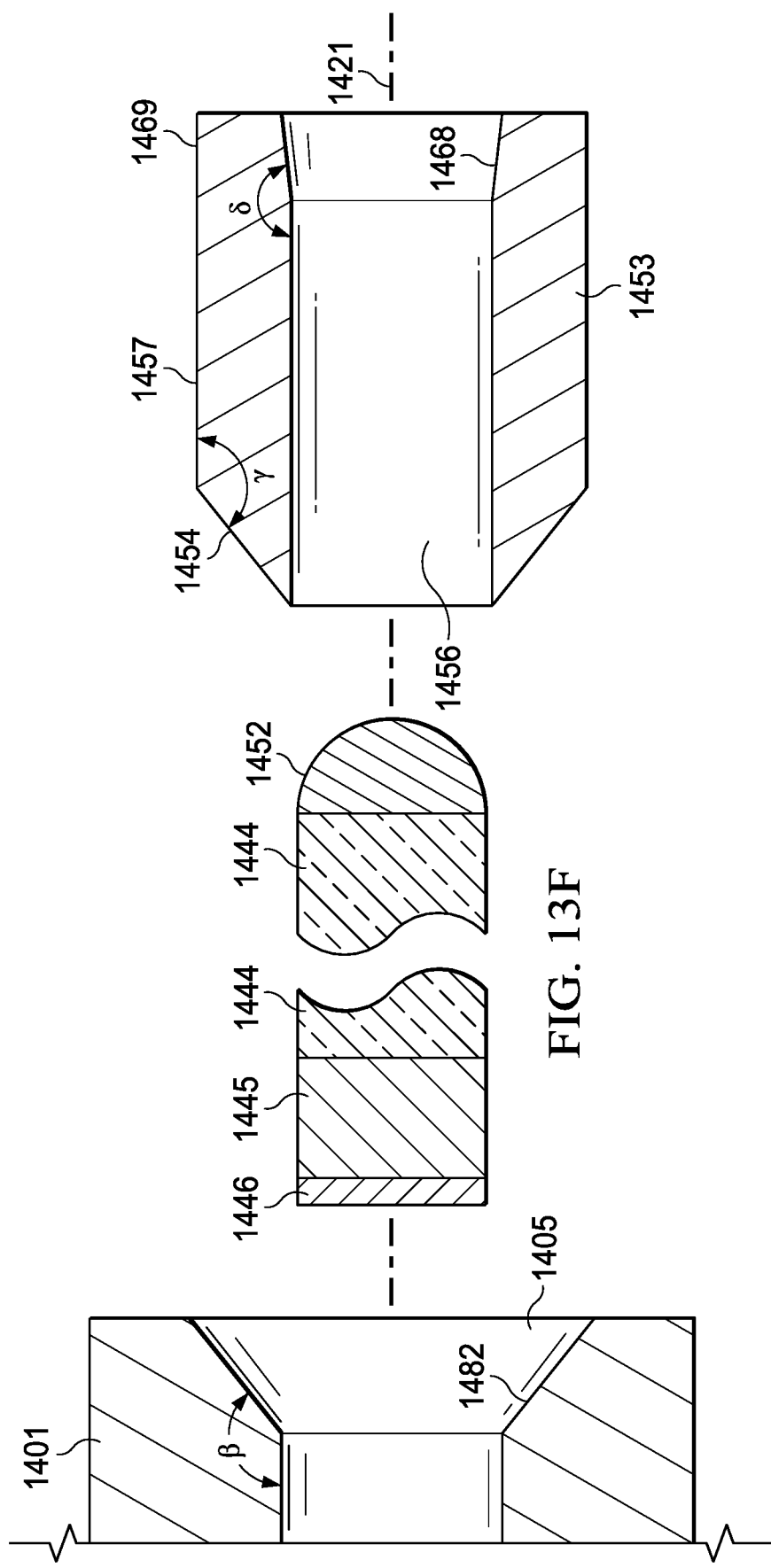
FIG. 13F is an exploded side view of an optical fiber and collet assembly.

Referring then to FIG. 13F, an alternate embodiment of optical fiber subassembly 1419 will be described.

Lead body 1401 includes stylet channel 1405 having an optical axis 1421. The lead body incorporates proximal contacts, distal electrodes and electrical conductors, as previously described. Stylet channel 1405 is terminated with frustoconical flare 1482. Frustoconical flare 1482 is coaxial with optical axis 1421. The frustoconical flare has inclination angle β, which can range from about 135° to about 150°.

In a preferred embodiment, the lead channel has a diameter of about 15-20% greater than the optical fiber to allow the fiber to move within the channel. Optical fiber 1444 is preferably a plastic fiber, as previously described. Optical fiber 1444 includes end reflector 1446 and side-firing fiber segment 1445, as previously described.

Optical fiber 1444 is proximally terminated by convex lens 1452. Convex lens 1452 consists of a polished ceramic material, such as sapphire, fixed to the optical fiber using a suitable optically transparent adhesive. In another embodiment, the lens is formed integrally with the transmission fiber. In another embodiment, the optical fiber is polished flat and no lens is incorporated.

Collet 1457 includes collet body 1453. Preferably, collet body 1453 is comprised of a ceramic material, such as Zirconia, or another MRI compatible material. Alignment tip 1454 is a chamfer integrally formed in the distal end of the collet body. Alignment tip 1454 forms angle of inclination γ of about 135°. In a preferred embodiment, angle γ matches angle β of frustoconical flare 1482.

Collet body 1453 further includes cylindrical collet chamber 1456. Collet chamber 1456 is coaxial with collet body 1453 and extends through alignment tip 1454. In a preferred embodiment, the collet is bonded to optical fiber 1444 at the collet chamber.

Lens shield 1469 is integrally formed with the proximal end of collet body 1453. It is designed to serve as a stop to prevent the optical fiber from impinging on the optical window of the IPG body. Lens shield 1469 further includes frustoconical lens opening 1468 ductedly connected with collet chamber 1456. The frustoconical lens opening is coaxial with the collet chamber and has an angle of inclination δ of about 175° with the collet chamber. Frustoconical lens opening 1468 serves to focus light toward the optical window.

Figure 13G:
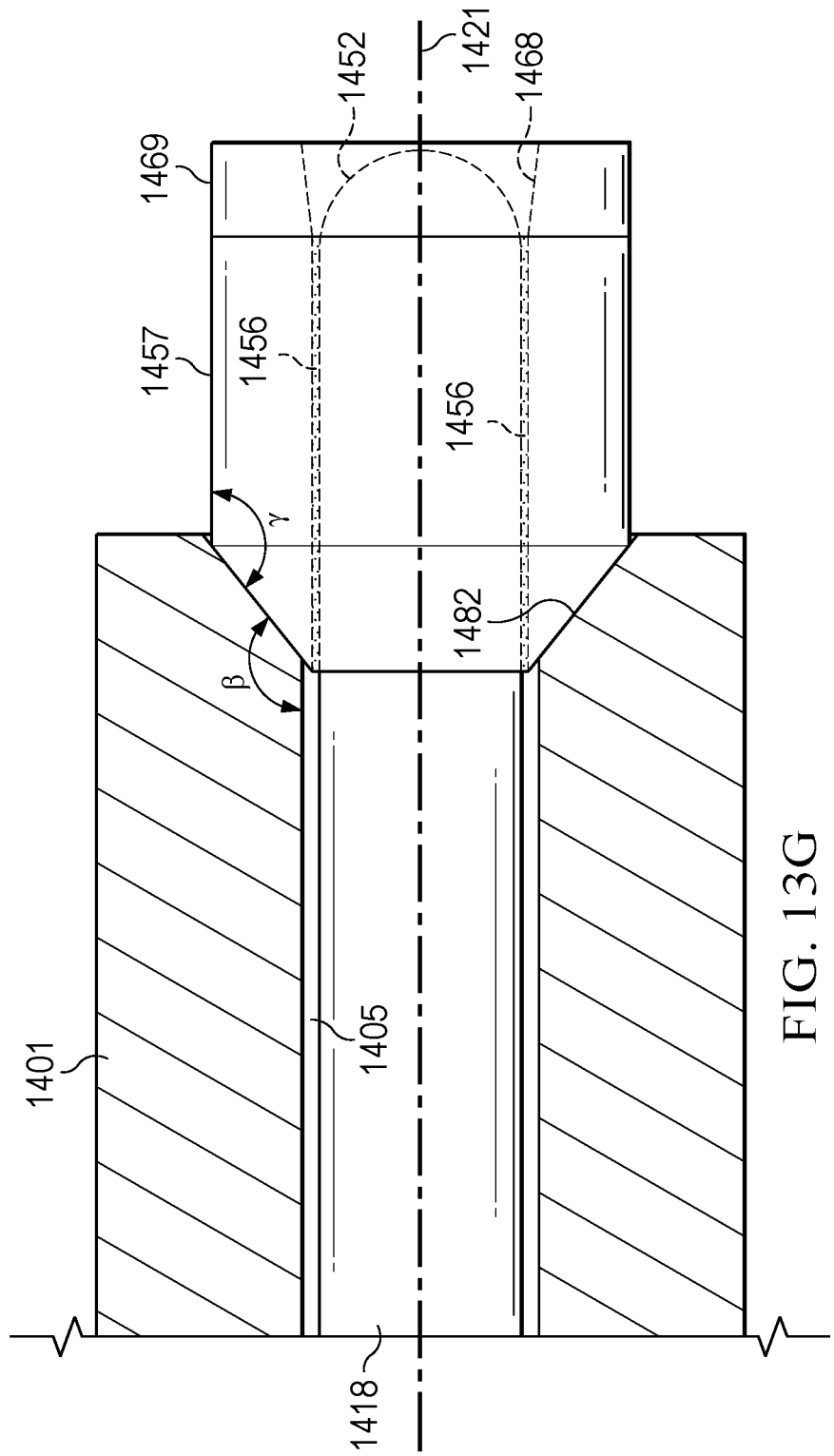
FIG. 13G is a side view of a preferred embodiment of an optical fiber and collet assembly.
Figure 13H:
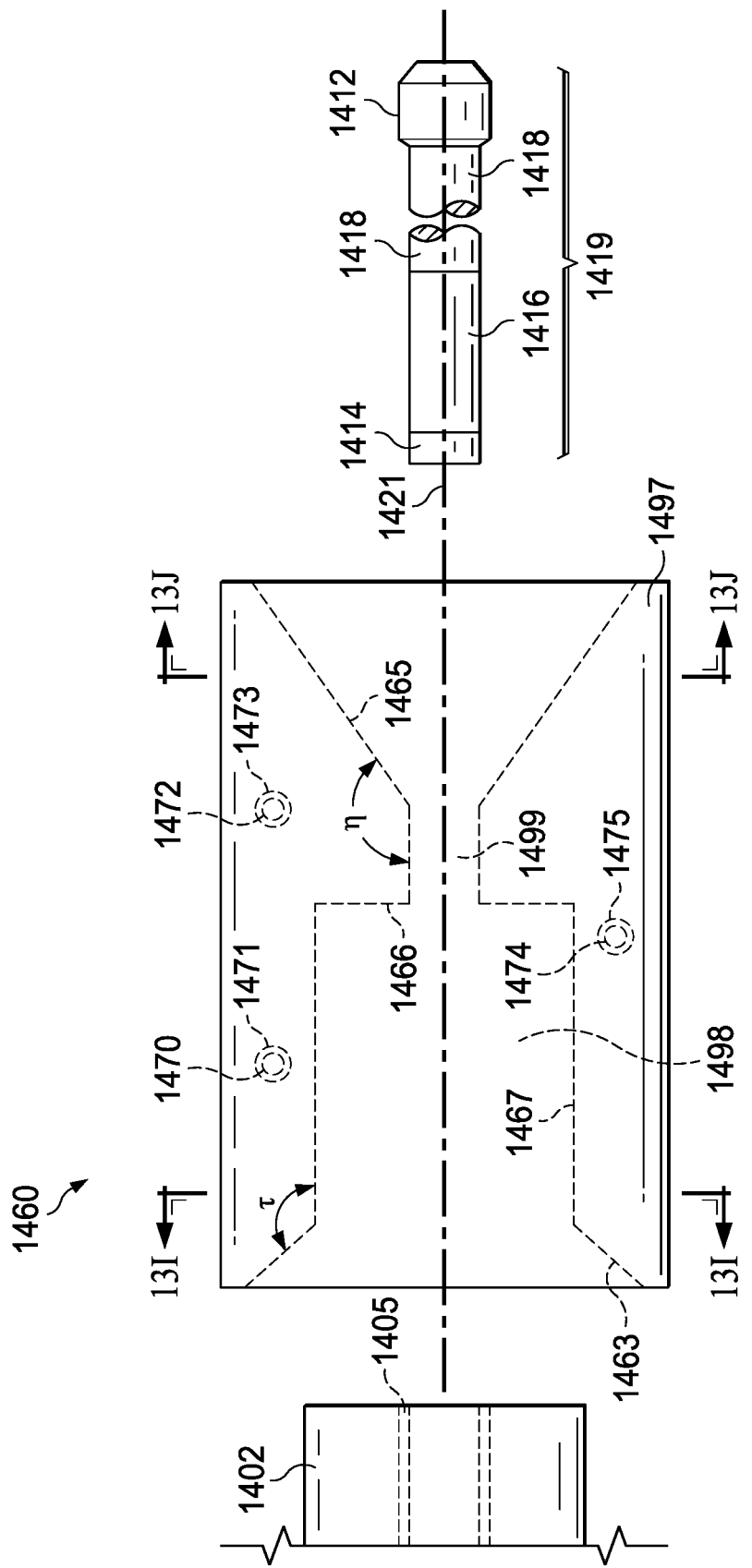
FIG. 13H is an exploded side view of a lead assembly.
Figure 13J:
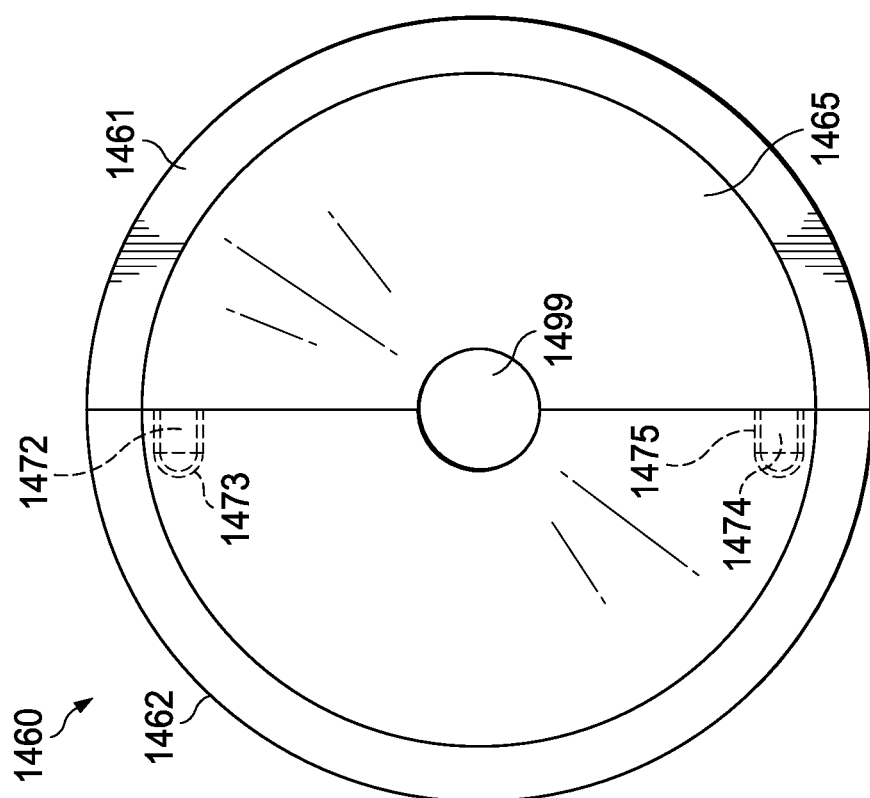
FIG. 13J is a plan view of an optical fiber threading assembly.
Figure 13I:
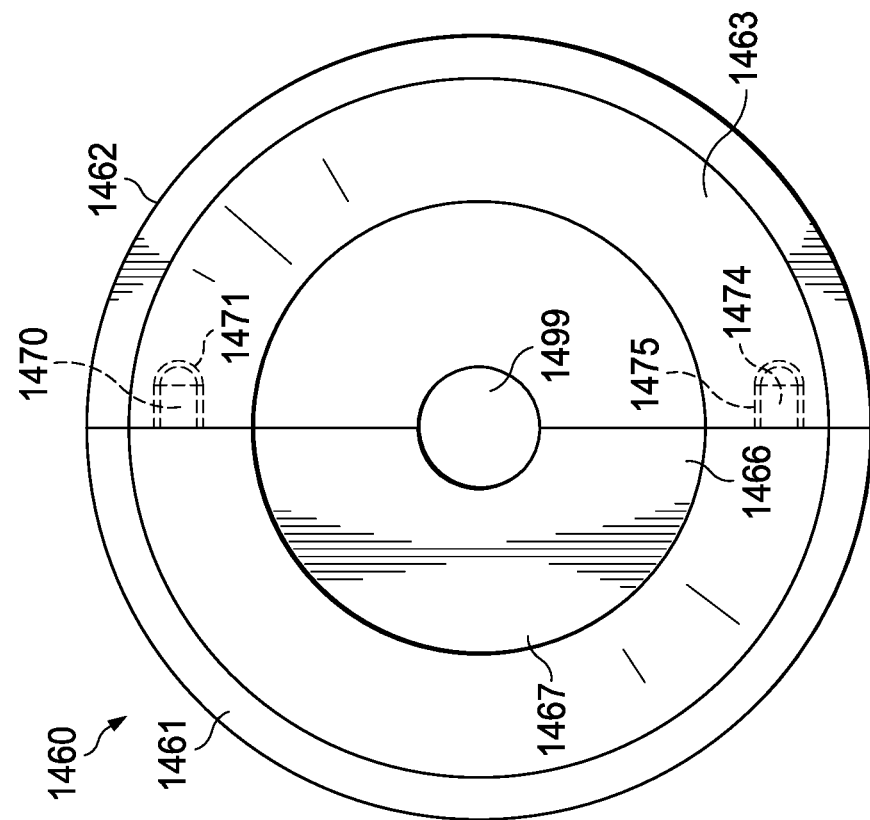
FIG. 13I is a plan view of an optical fiber threading assembly.
Figure 13K:
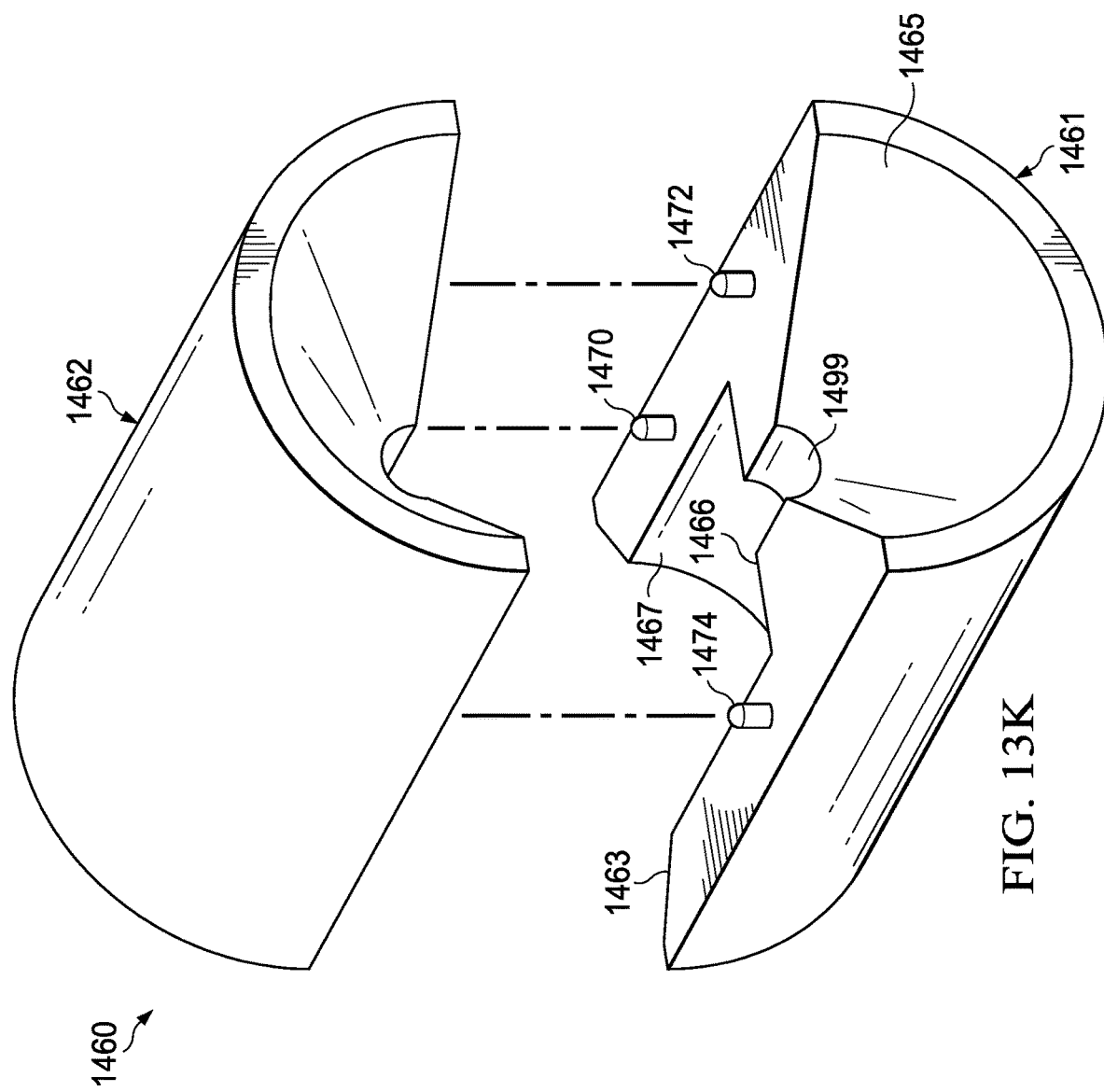
FIG. 13K is an exploded perspective view of an optical fiber threading assembly.

Referring then to FIG. 13G, the proximal end of the optical fiber is shown positioned in collet chamber 1456. Lens 1452 does not extend past lens shield 1469. The fiber is fixed in the collet chamber by a suitable epoxy.

Optical fiber 1418 is positioned in stylet channel 1405 of lead body 1401. Frustoconical flare 1482 serves to guide insertion of the optical fiber into the lead channel. The interface of frustoconical flare 1482 and alignment tip 1454 also serves to center optical fiber 1444 and lens 1452 on axis 1421. The outer diameter of collet 1457 is less than the outer diameter of lead body 1401 but greater than the diameter of stylet channel 1405, such that when the lead is inserted in the header, the lead body acts as a stop for the collet, such that the side firing fiber segment of the fiber is adjacent the optical window.

Referring then to FIG. 13H-13K, a preferred embodiment of optical threading assembly 1460 is described. Inserting the optical fiber into the stylet channel of the lead can be difficult due to the miniature size of the fiber and small diameter of the stylet channel. In the same way, during surgery, the replacement of the stylet in the stylet channel can be difficult. These difficulties are compounded by necessity for speed, manual dexterity and visual acuity. Improper insertion of the optical fiber can lead to damage to the fiber causing breakage or early degradation of the fiber. Likewise, improper stylet insertion can compromise the lead body. The optical fiber threading assembly solves these and other problems.

Optical threading assembly 1460 includes guide body 1497. The guide body is a roughly 1 cm diameter cylinder and is comprised of thermoplastic. The assembly is preferably formed either using injection molding, or additive manufacturing. Other methods of manufacture will suffice. Guide body 1497 is generally cylindrical and is comprised of two opposing semicylinders, 1461 and 1462.

Optical threading assembly 1460 includes frustoconical lead centering surface 1463 at its distal end. Frustoconical lead centering surface 1463 is coaxial with axis 1421. Frustoconical lead centering surface 1463 is adjacent cylindrical alignment surface 1467. Cylindrical alignment surface 1467 forms alignment cavity 1498. Frustoconical lead centering surface 1463 forms an angle of inclination τ of about 135° with cylindrical alignment surface 1467. The alignment cavity has a diameter generally equal to that of lead body 1402. The alignment cavity is terminated with stop surface 1466. Stop surface 1466 is a generally annular ring formed perpendicular to and coaxial with axis 1421.

Adjacent to and ductedly connected with alignment cavity 1498, is generally cylindrical fiber alignment duct 1499. Fiber alignment duct 1499 is coaxial with axis 1421. The diameter of the fiber alignment duct is generally the same as the diameter of stylet channel 1405 of lead body 1402.

Fiber alignment duct 1499 is adjacent to and ductedly connected with frustoconical optical fiber centering surface 1465. Frustoconical optical fiber centering surface 1465 forms an angle of inclination η of about 135° with fiber alignment duct 1499. Frustoconical optical fiber centering surface 1465 is coaxial with axis 1421.

Semicylinder 1461 includes alignment pegs 1474, 1470, and 1472. Semicylinder 1462 includes alignment recesses 1475, 1471, and 1473. Alignment peg 1474 is diametrically opposed to alignment recess 1475. Alignment peg 1470 is diametrically opposed to alignment recess 1471. Alignment peg 1472 is diametrically opposed to alignment recess 1473. The diameter of each of alignment recesses 1475, 1471, and 1473 is such that alignment pegs 1474, 1470, and 1472 can be secured by a press fit. Using the alignment pegs and recesses, the semicylinders may be easily assembled for use and then disassembled after use, as will be further described.

In use, optical threading assembly 1460 aligns lead body 1402 and optical fiber subassembly 1419 along axis 1421. Lead body 1402 is aligned using frustoconical lead centering surface 1463 and held in position in alignment cavity 1498 by alignment surface 1467 and stop surface 1466. Optical fiber subassembly 1419 is aligned using frustoconical centering surface 1465 and moved through fiber alignment duct 1499 and into the stylet channel of the lead body.

In the same way, a stylet may be positioned in the stylet channel in place of the optical fiber.

Referring then to FIGS. 14A-15B, alternate embodiments for surgical leads are described.

Surgical leads may be configured with two or more multi-duct leads containing integrated optical fibers, depending upon the number of electrodes in the array and the desired number of optical reflectometry channels. The multi-duct leads may be organized into pairs of emitter leads and detector leads. Generally, a surgical lead configured with two multi-duct leads incorporate one optical reflectometry channel, while a surgical lead with four multi-duct leads incorporates two optical reflectometry channels. A surgical lead with two multi-duct leads with integrated optical fibers is capable of determining sagittal spinal cord position. Whereas a surgical lead with four multi-duct leads with integrated optical fibers is capable of determining sagittal and coronal spinal cord position.

Figure 14A:
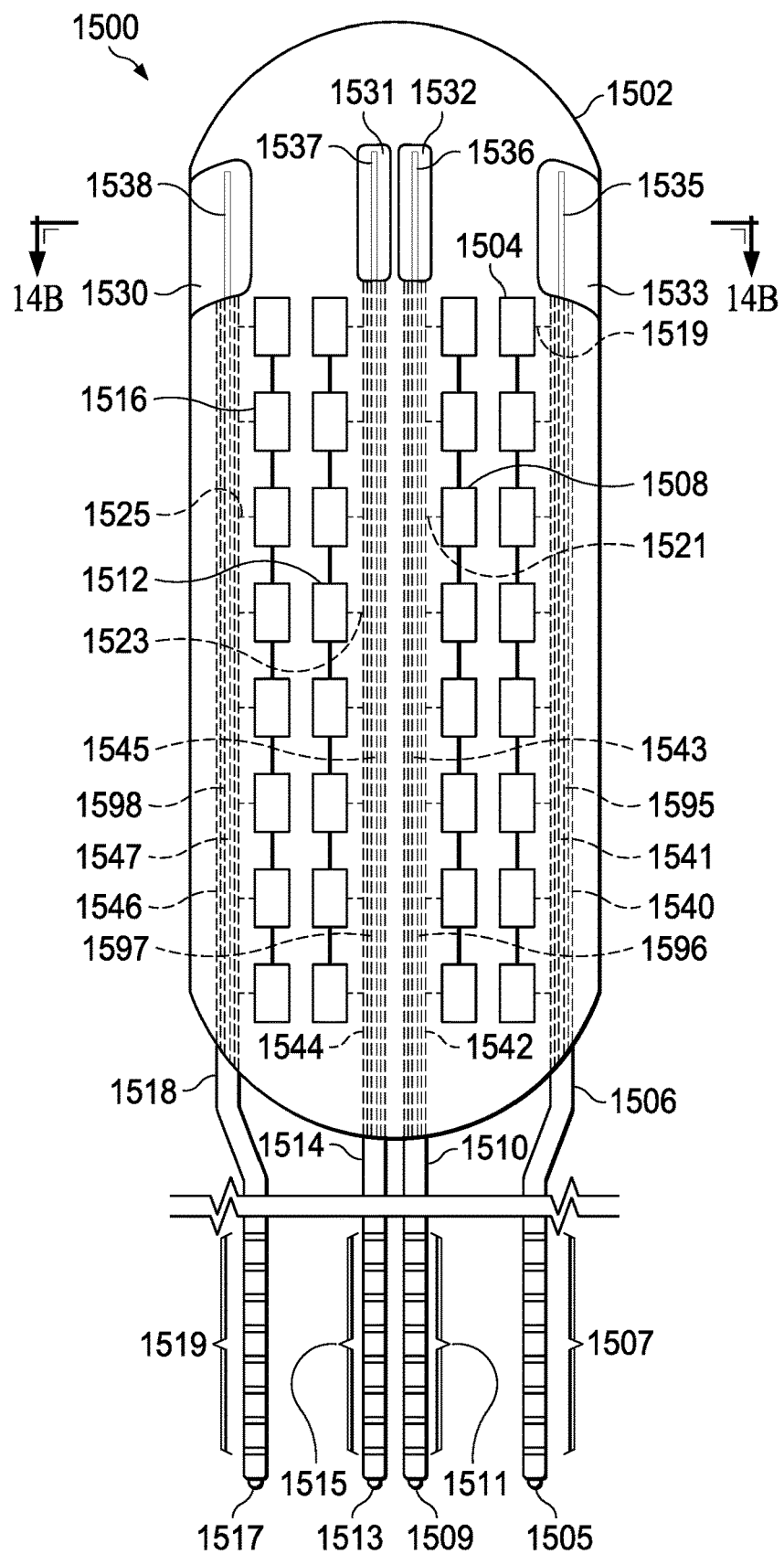
FIG. 14A is a plan view of a preferred surgical lead.

Referring then to FIG. 14A, a preferred embodiment of surgical lead 1500 is described.

Electrode array 1500 is comprised of integrated flexible panel 1502. Panel 1502 is preferably of a medical grade inert polymer material, such as Pellethane 55-D. Flexible panel 1502 houses multi-duct leads 1506, 1510, 1514, and 1518. In a preferred embodiment, the multi-duct leads are sealed within the body of the flexible panel. Each of multi-duct leads 1506, 1510, 1514, and 1518 includes a central lumen 1595, 1596, 1597 and 1598, respectively. Each central lumen includes an optical transmission fiber 1541, 1543 1545 and 1547, respectively. Each optical transmission fiber terminates at a distal end in a side firing optical fiber segment, 1535, 1536, 1537 and 1538, respectively. The side firing optical fiber segments are constructed, as previously described. Each side firing optical fiber segment is positioned adjacent distally positioned optical window 1533, 1532, 1531 and 1530, respectively. In a preferred embodiment, each of the optical windows is an optically transparent segment of the polymer comprising flexible panel 1502. By placing the optical windows and the side firing segment at the most distal portion of the panel, there are no metallic components such as electrodes or connections to interfere with radial dispersion of light, while keeping the optical sensing region proximate the electrode arrays. This improves optical signal strength and consequently lowers power consumption. In an alternate embodiment, the optical windows are placed parallel to and adjacent columns of the electrode arrays.

Panel 1502 further comprises electrode arrays 1504, 1508, 1512, and 1516 positioned adjacent multi-duct leads 1506, 1510, 1514 and 1518, respectively. In a preferred embodiment, each of electrode arrays 1504, 1508, 1512, and 1516 include eight electrodes embedded in the panel and having an exposed face external to the panel. Each of multi-duct leads 1506, 1510, 1514 and 1518 incorporate eight electrical conductors that extend the length of the panel and the multi-duct leads, as previously described. Each electrode is connected through the conductors in the lead body to exactly one lead contact. Electrode array 1504 is connected to lead contacts 1507. Electrode array 1508 is connected to lead contacts 1511. Electrode array 1512 is connected to lead contacts 1515. Electrode array 1516 is connected to lead contacts 1519. In a preferred embodiment, the electrodes are comprised of platinum-iridium alloy (nominally 90%/10% to 80%/20%).

Each of multi-duct leads 1506, 1510, 1514 and 1518 terminates at ferrules 1505, 1509, 1513 and 1517, respectively. In a preferred embodiment, the ferrules are bonded to the fibers, as previously described.

Figure 14B:
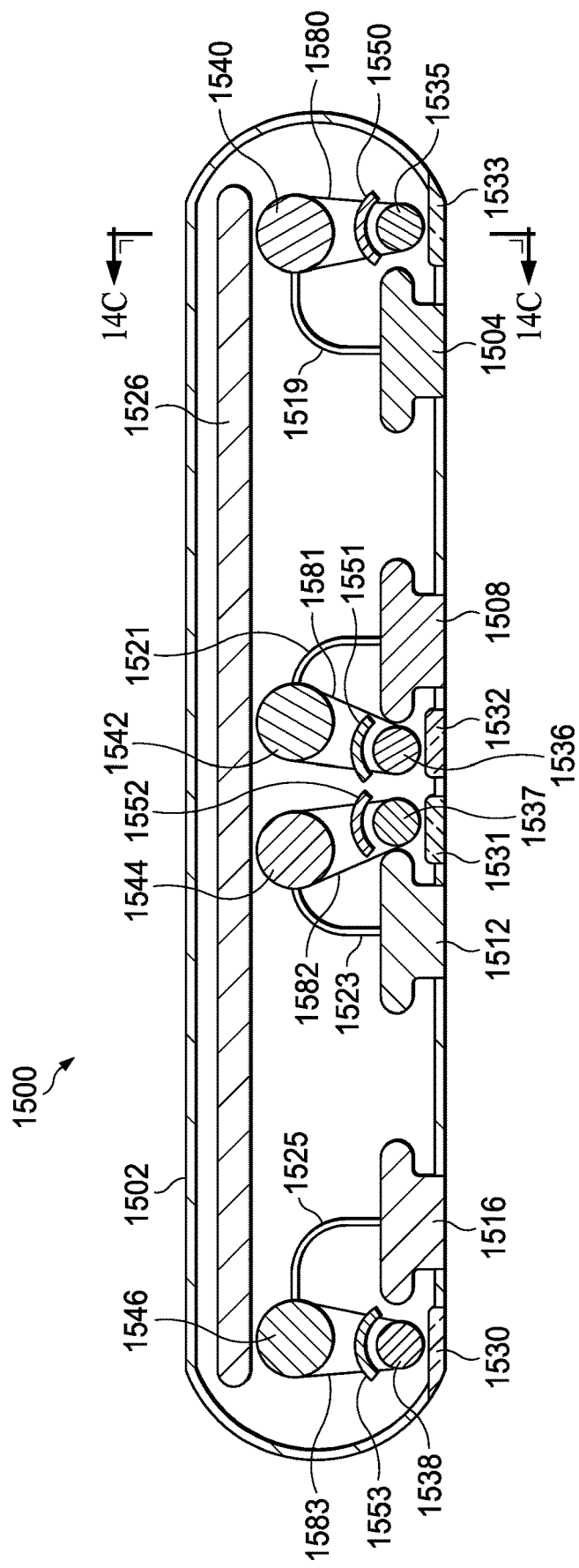
FIG. 14B is a cross-sectional view of a preferred surgical lead.
Figure 14C:
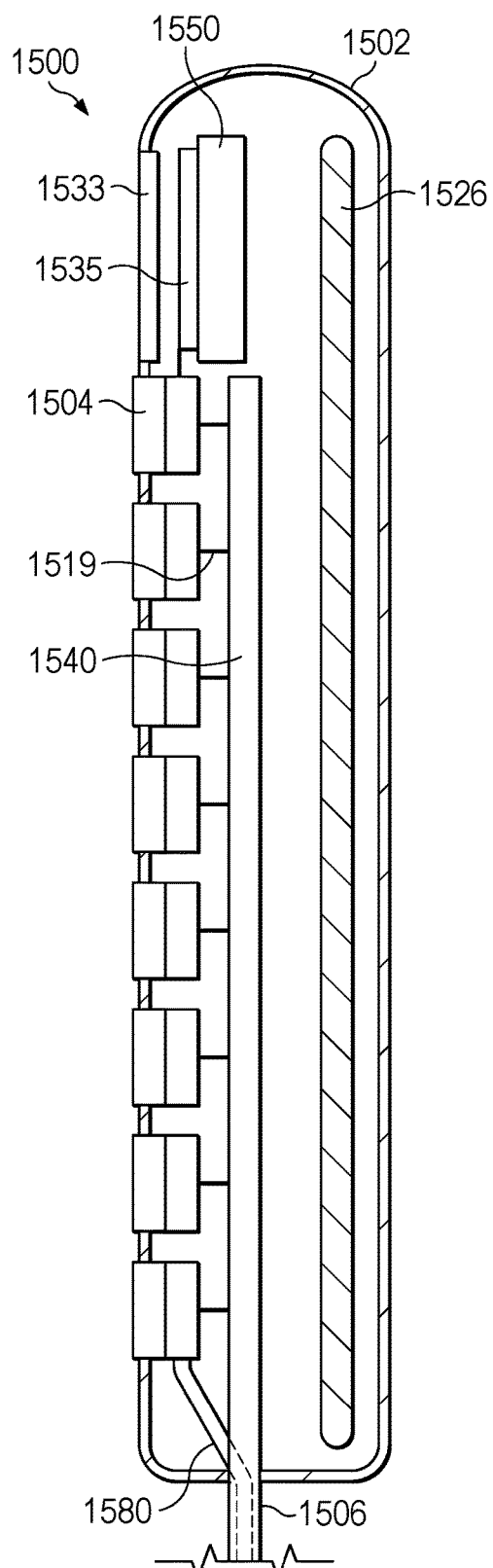
FIG. 14C is a cross-sectional view of a preferred surgical lead.

Referring then to FIGS. 14B and 14C, each of electrode arrays 1504, 1508, 1512 and 1516 is connected through electrical connections 1519, 1521, 1523 and 1525 to one of conductor bundles 1540, 1542, 1544 and 1546, respectively. The conductor bundles contain the individual conductors, radially separated, as previously described. The side firing fiber segments separate from the multi-duct leads and away from the conductor bundles in manifolds 1580, 1581, 1582 and 1583, respectively.

Panel 1502 includes light reflectors 1550, 1551, 1552 and 1553, adjacent side firing optical fiber segments 1535, 1536, 1537, and 1538, respectively. The light reflectors are preferably semicylindrical or parabolic, and flexible. In a preferred embodiment, light reflectors 1550, 1551, 1552 and 1553 are comprised of a non-conductive material polymer, such as Pellethane-55D, coated with a non-conductive reflective surface, such as titanium dioxide. This material operates at the desired wavelength from red to infrared and may be applied as a paint or film. The reflections improve optical efficiency by redirecting radially produced light from the emitter fiber segments toward the optical windows, or, alternatively, reflecting incoming light from the optical windows and into the detector fiber segments.

Panel 1502 is further comprised of lattice shield 1526. Lattice shield 1526 is comprised of a generally flat flexible film and interdigitates with the polymeric material of the lead body. In a preferred embodiment, lattice shield 1526 is coated with a reflective material, such as titanium dioxide ($TiO_2$) adjacent the optical fibers. Lattice shield is contained within the panel adjacent each of conductor bundles 1540, 1542, 1544 and 1546, and generally extends the length of the panel.

In one embodiment, the lattice shield may be comprised of an electrically conductive material, such as carbon nanofibers, and operates as a heat-sink to draw heat away from the electrode contact arrays and disperse it dorsally. In another embodiment, leads 1518, 1514, 1510, and 1506 each include a ground, as shown in FIG. 13C. Ground line 1451i connects lattice shield 1526 with the anchor ring located at the proximal end of the lead. The anchor ring is connected to the IPG ground. This configuration provides optimal electrical shielding for MRI compatibility.

Figure 15A:
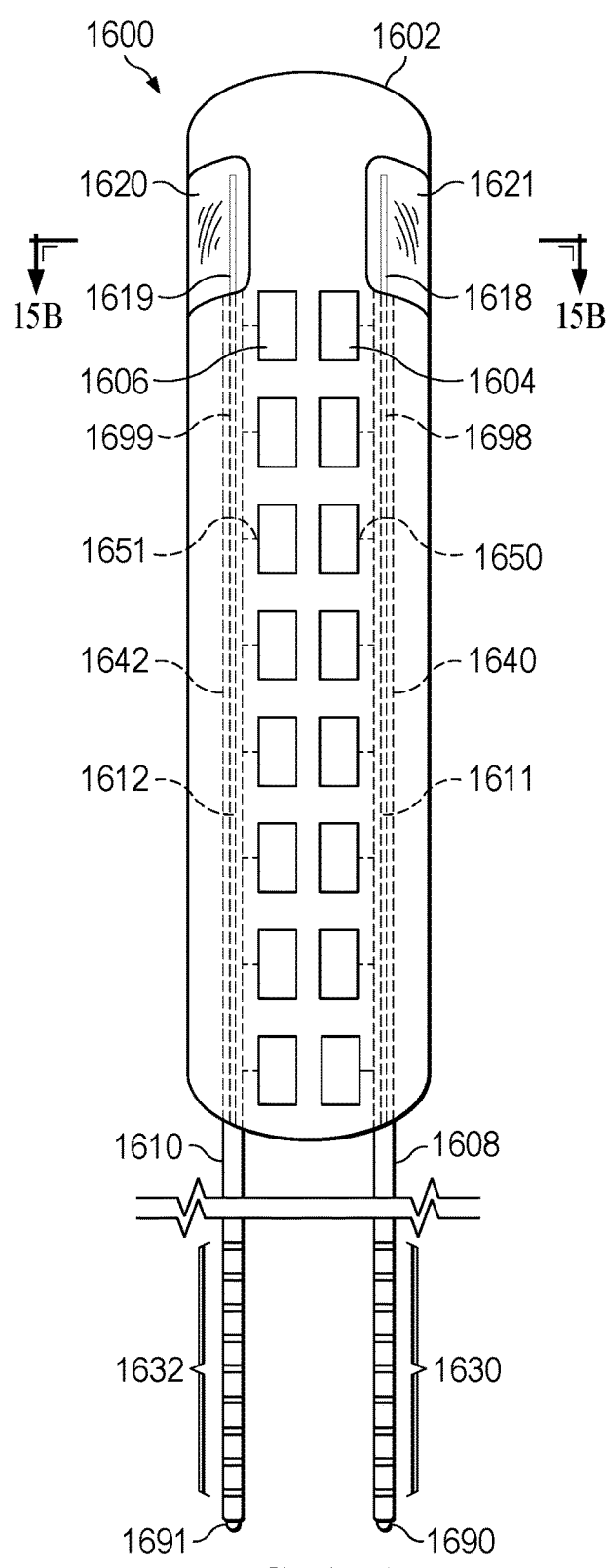
FIG. 15A is a plan view of a preferred surgical lead.

Referring then to FIG. 15A, a preferred embodiment of surgical lead 1600 is described.

Surgical lead 1600 is comprised of integrated flexible panel 1602. In a preferred embodiment, flexible panel 1602, is a medical grade inert flexible polymeric material, as previously described. Integrated within the flexible panel are multi-duct leads 1608 and 1610. Each of multi-duct leads 1608 and 1610 includes central lumen 1698 and 1699, respectively. The central lumens include optical fibers 1611 and 1612, respectively. Each optical fiber terminates in a side firing optical fiber segment 1618 and 1619, respectively. The side firing optical segments are constructed as previously described. Each side firing optical segment is positioned adjacent an optical window 1621 and 1620, respectively. In a preferred embodiment, each of the optical windows is an integrally formed optically transparent region of flexible panel 1602.

Panel 1602 further comprises electrode arrays 1604 and 1606. Each of electrode arrays 1604 and 1606 includes eight electrodes, embedded in the surface of panel 1602, having an exposed face exterior to the panel. In a preferred embodiment, the electrodes are a platinum-iridium alloy. Each of the electrodes is connected through the conductors in the multi-duct lead bodies to exactly one lead contact, as previously described. Electrode array 1604 is connected to lead contacts 1630. Electrode array 1606 is connected to lead contacts 1632.

Each of multi-duct leads 1608 and 1610, terminates at ferrules 1690 and 1691, respectively. The ferrules are attached and bonded to the optical fibers, as previously described.

Figure 15B:
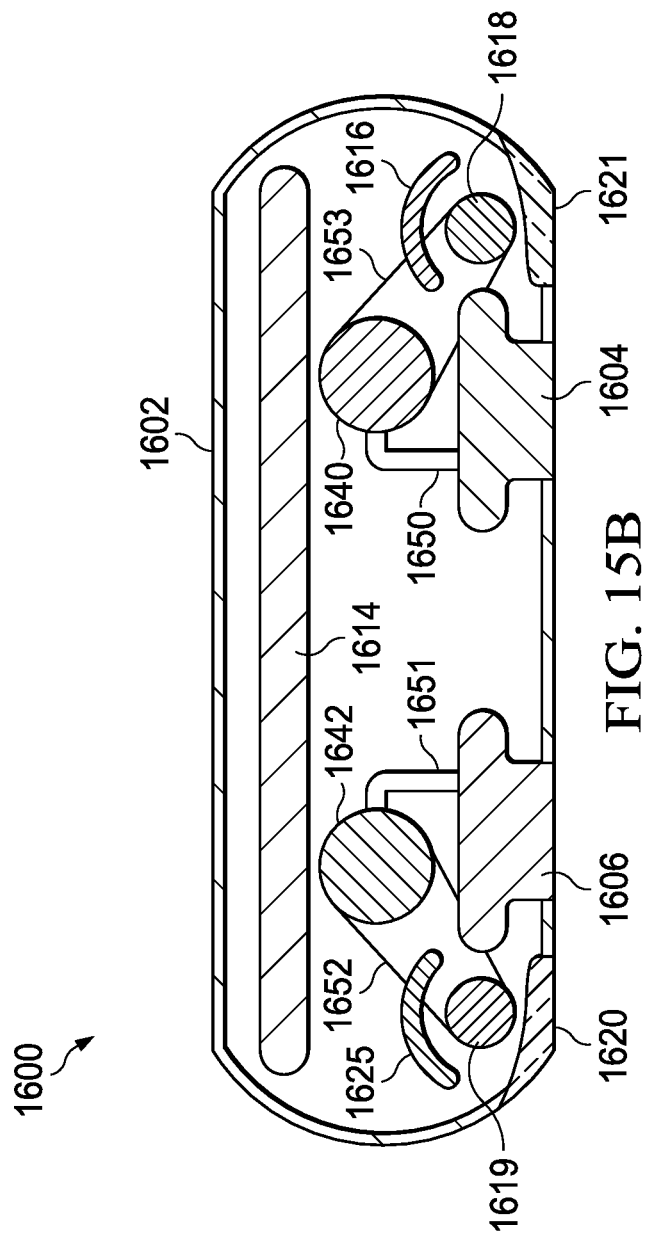
FIG. 15B is a cross-sectional view of a preferred surgical lead.

Referring then to FIG. 15B, the conductors in the multi-duct lead bodies separate from side firing optical fiber segment 1618 and 1619 in optical manifolds 1653 and 1652, respectively. Each of electrode arrays 1604 and 1606 is connected through electrical connections 1650 and 1651 to the conductors in one of conductor bundles 1640 and 1642, respectively.

Panel 1602 is further comprised of lattice shield 1614. Lattice shield 1614 is comprised of a generally flat flexible film that is integrally formed with both the flexible panel. As previously described, the lattice shield may be coated with reflective material adjacent the optical fibers. The lattice shield may be connected to a ground contact for further connection to the IPG ground, as previously described.

Panel 1602 further comprise reflectors 1616 and 1625, positioned adjacent side firing optical fiber segments 1618 and 1619, respectively. In preferred embodiments, the reflectors are generally semicylindrical or are parabolic. In another embodiment, the reflectors may be flat flexible panels. The reflectors serve to aid in the reflection of light emitted from a side firing fiber segment out through an optical window or to focus incoming light through optical windows and back into the fiber for transmission to a detector within the IPG.

Figure 16A:
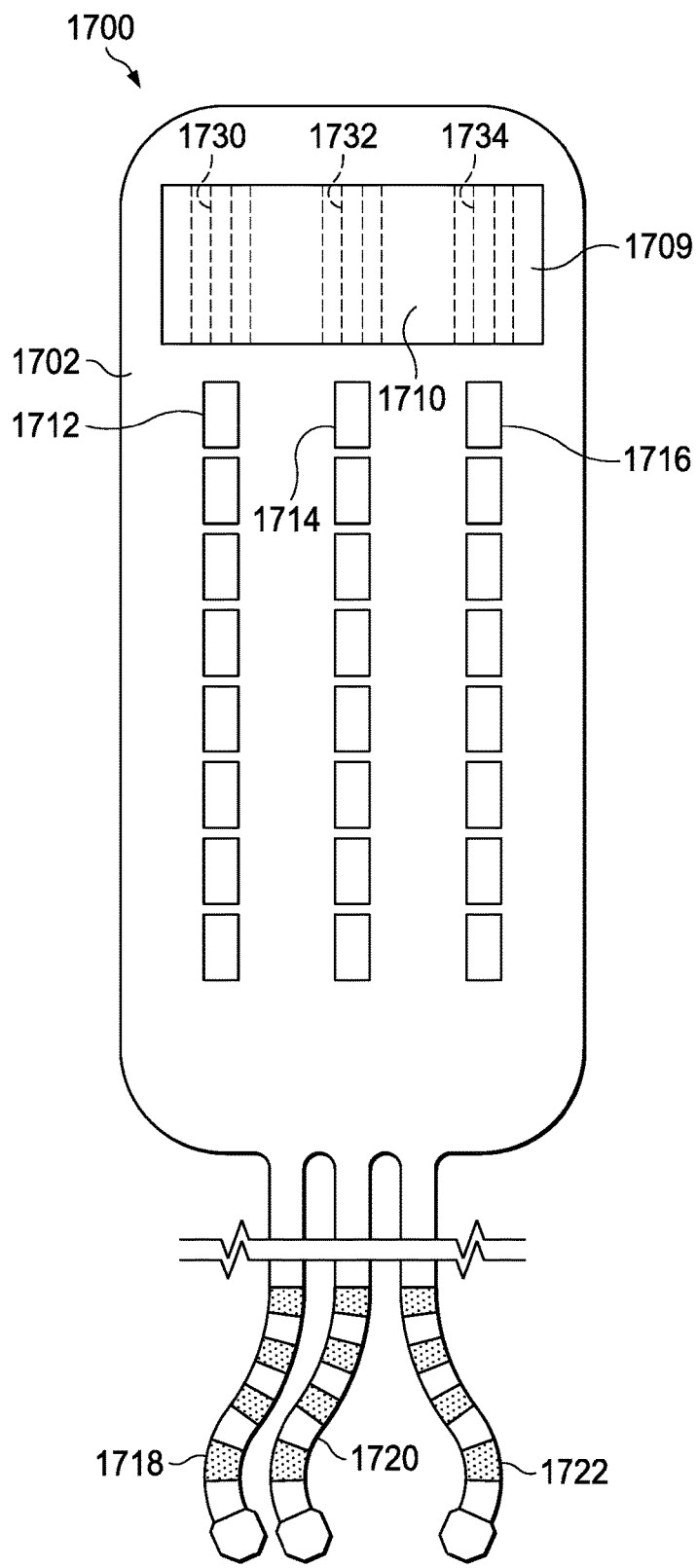
FIG. 16A is a plan view of a surgical lead.
Figure 16B:
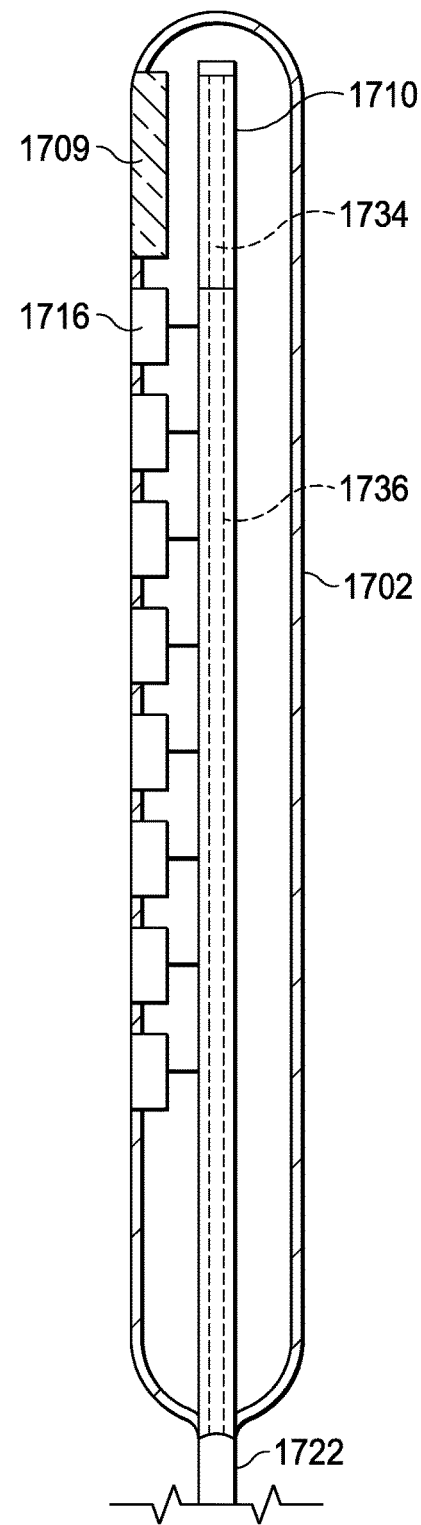
FIG. 16B is a cross-sectional view of a surgical lead.
Figure 16C:
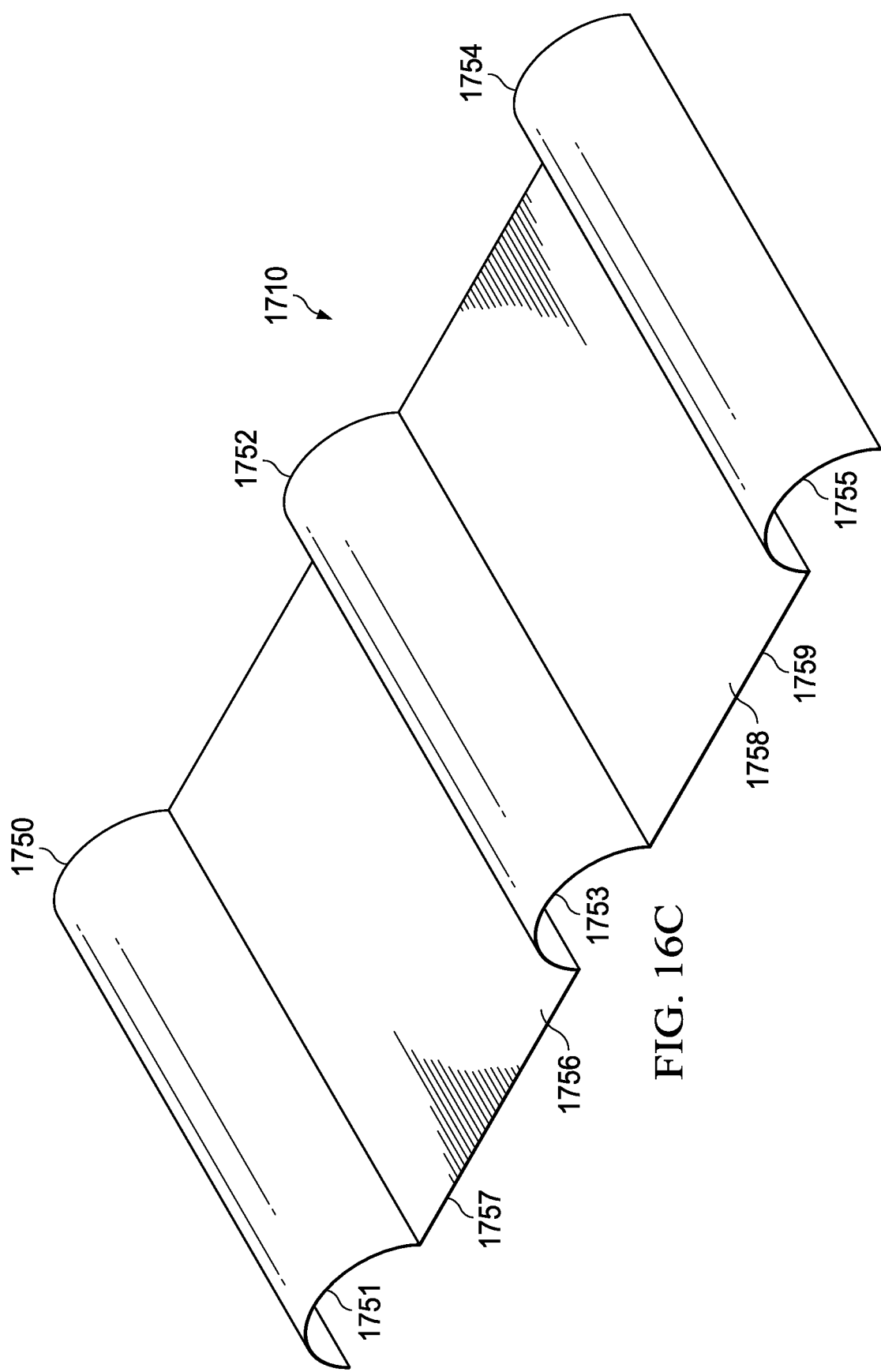
FIG. 16C is an isometric view of a parabolic reflector for a surgical lead.

Referring to the FIGS. 16A, 16B and 16C, an alternate embodiment of surgical lead 1700 will be described. Integrated panel 1702 is generally flat, polymeric and rectangular, as previously described. Integrated within integrated panel 1702 are multi-duct leads 1718, 1720 and 1722 with optical fiber 1736, as previously described. Each of the multi-duct leads have proximal electrical contacts which are individually connected to electrode arrays 1712, 1714 and 1716 through conductors, as previously described. Integrated panels 1702 further comprises optical window 1709 integrated into the panel adjacent side firing fiber segments 1730, 1732 and 1734, as previously described.

Composite reflector 1710 is comprised a plurality of alternating parabolic surfaces, such as parabolic surfaces 1750, 1752 and 1754, and flat interstitial surfaces such as surfaces 1756 and 1758. The parabolic surfaces and the flat surfaces are preferably comprised of a flexible inert plastic with sufficient rigidity to sustain moderate bending. In a preferred environment, polyvinyl chloride is used. Internal surfaces 1751, 1753 and 1755 of the parabolic surfaces and internal surfaces 1757 and 1759 of the flat surfaces all are coated with a reflective material such as titanium dioxide. Internal surfaces 1751, 1753 and 1755 are positioned adjacent side firing fiber segments 1730, 1732 and 1734 and serve to function as previously described.

In another preferred embodiment, composite reflector 1710 is grounded to the IPG case, through a conductor in one of the multi-duct leads, as previously described.

Referring then to FIGS. 17A and 17B an alternate embodiment of surgical lead 1800 will be further described.

Integrated panel 1802 generally comprises a flat, polymeric and rectangular, as previously described. Integrated panel 1802 include electrode arrays 1810 and 1812 connected to multi-duct leads 1814 and 1818, as previously described. Integrated panel 1802 further comprise multi-duct leads 1814, 1816 and 1818 integrally formed, as previously described. Each of multi-duct leads 1814, 1816 and 1818 includes optical fiber 1850 with side firing fiber segments 1820, 1822, and 1824. Each optical fiber 1850 is positioned to terminate in a right-angle prism, such as right-angle prism 1804, 1806, and 1808. The right-angle prisms are positioned to direct light to an optical fiber from optical windows 1811, 1813, and 1817, or from the optical fiber to an optical window, as the case may be.

Figure 18:
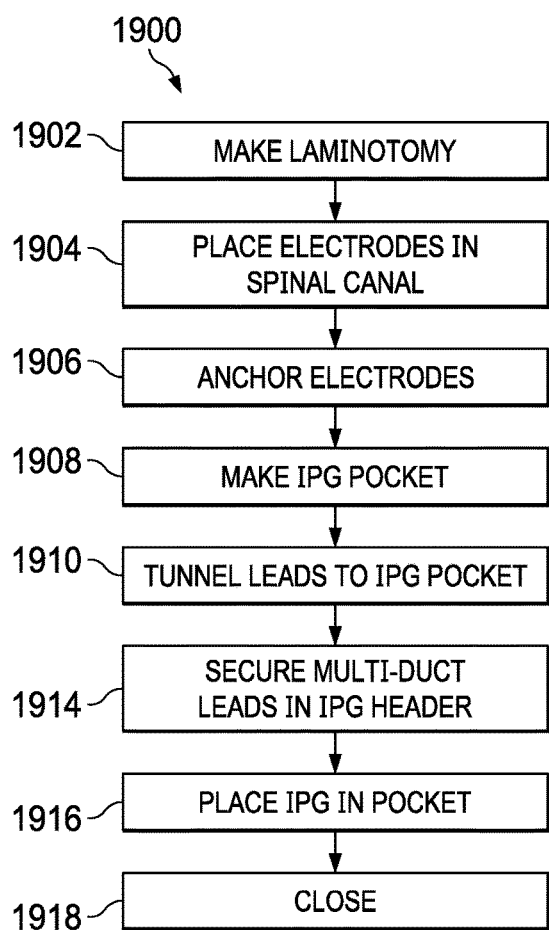
FIG. 18 is flowchart of the steps of a preferred method of placement of a surgical lead.

Referring then to FIG. 18, method 1900 for the placement of a surgical lead, will be described.

At step 1902, a laminotomy is conducted at the segmental level corresponding to the somatotopic distribution of the patient's pain.

At step 1904, electrodes are placed in the spinal canal. Typically, the electrodes are placed in the dorsal epidural space by manually inserting the electrode array in the laminotomy cavity.

At step 1906, the electrodes are anchored to the fascia, ligament or the adjacent bone.

At step 1908, an incision is made for the IPG.

At step 1910 the leads are tunneled subcutaneously from the electrode insertion site to the IPG pocket.

At step 1914, the multi-duct leads are secured in the IPG header. If the fibers are not secured in the multi-duct leads, then they may be inserted and secured at this step, as will be further described. In practice, the lead body, including the fiber subassembly, is threaded into the appropriate lead channel bringing the proximal lead contacts into electrical contact with the canted coil springs, of the lead channel. The multi-duct lead is advanced in the lead channel until the multi-duct lead body encounters frustoconical centering surface 724, which guides it along cylindrical alignment surface 726, until it engages stop surface 730 in anchor ring chamber 728. Simultaneously, the ferrule is advanced into alignment cylinder 712 until it encounters ferrule centering surface 716. Ferrule centering surface 716 aligns the optical fiber in buffer gap 734 and with the optical window in the IPG casing, adjacent the composite optoelectronic device 740. The multi-duct lead is secured in the lead channel by advancing anchor screw 708, using a torque limited ratchet, until it engages anchor ring 1410.

At step 1916 the IPG is placed in the pocket.

At step 1918, the procedure is ended.

Figure 19:
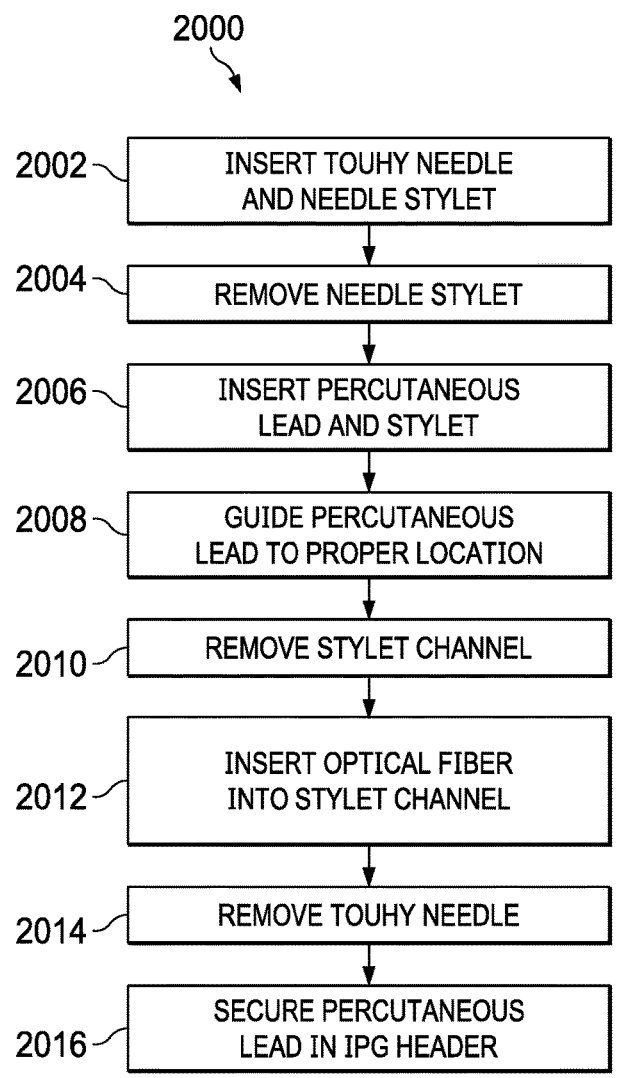
FIG. 19 is flowchart of the steps of a preferred method of placement of a percutaneous lead.

Referring to FIG. 19, preferred method 2000 of placement of a percutaneous lead will be described.

At step 2002, a Touhy needle and needle stylet are inserted into spinal canal at the appropriate segmental level.

At step 2004, the needle stylet is removed from the lumen of the Touhy needle.

At step 2006, the percutaneous lead with included stylet guide wire is inserted into the bore of the Touhy needle.

At step 2008, the percutaneous lead is guided to the proper location in the spinal canal using the stylet guide wire, under fluoroscopy.

At step 2010, the stylet guide wire is removed from the stylet channel.

At step 2012, the optical fiber is inserted into the stylet channel, as previously described.

At step 2014, the Touhy needle is removed, while holding the lead in place.

At step 2016, the proximal end of the percutaneous lead is secured in the IPG header, as previously described.

Figure 20:
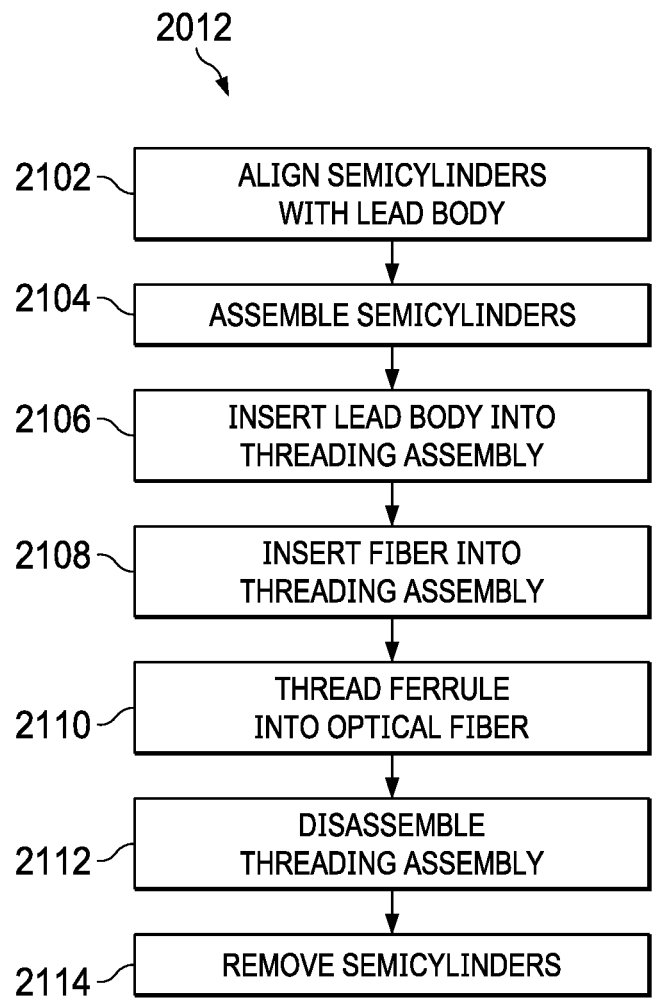
FIG. 20 is flowchart of a method of the steps of a preferred method of securing an optical fiber in a stylet channel of a lead.

Referring then to FIG. 20, step 2012 of securing the optical fiber in a stylet channel of a lead, will be further described.

At step 2102, semicylinders 1461 and 1462, are aligned with the percutaneous lead body. At step 2104, semicylinders 1461 and 1462 are assembled by press fit. At step 2106, the proximal end of the percutaneous lead body is inserted into the alignment cavity of the threading assembly, guided by frustoconical lead centering surface 1463. Alignment surface 1467 aligns the multi-duct lead body with alignment cavity 1498.

At step 2108, optical fiber 1418 is inserted into fiber alignment duct 1499, guided by frustoconical optical fiber centering surface 1465. The optical fiber is then inserted into stylet channel 1405 of multi-duct lead body 1402, of the threading assembly.

At step 2110, ferrule 1412 is threaded onto optical fiber 1418.

In an alternate embodiment, a stylet may be placed in the fiber alignment duct and the stylet channel at this step. If so, the method concludes here.

At step 2112, the threading assembly is disassembled.

At step 2114, the semicylinders are removed from the assembled lead body and optical fiber.

The invention claimed is:

1. An implantable pulse generator casing for connection to a set of leads comprising:
   a shell;
   a header, operatively attached to the shell, having a set of parallel lead channels;
   an optical window, positioned in the shell, adjacent the set of parallel lead channels;
   a set of light emitting devices, adjacent the optical window, perpendicular to the set of parallel lead channels;
   a set of light detecting devices, adjacent the optical window, perpendicular to the set of parallel lead channels;
   an optical signal processor, having a memory, operatively connected to the set of light emitting devices and the set of light detecting devices; and,
   the memory incorporating a set of instructions that when executed cause the optical signal processor to:
      set a first emitter current on a light emitting device of the set of light emitting devices;
      read an initial detector voltage of a light detecting device of the set of light detecting devices;
      read a steady state detector voltage of the light detecting device of the set of light detecting devices;
      compare the initial detector voltage to the steady state detector voltage; and,
      if the steady state detector voltage is less than the initial detector voltage, then increase the first emitter current to a second emitter current.

2. The implantable pulse generator casing of claim 1 wherein the at least one light emitting device further comprises a set of near infrared light emitting device.

3. The implantable pulse generator casing of claim 1 wherein the at least one light emitting device further comprises a set of visible light emitting device.

4. The implantable pulse generator casing of claim 1 wherein the shell further comprises two shell halves hermetically sealed together.

5. The implantable pulse generator casing of claim 1 wherein the optical window is an alumina material.

6. The implantable pulse generator casing of claim 1 wherein the optical window is joined to the shell by ceramic brazing.

7. The implantable pulse generator casing of claim 1 wherein the shell is a glass material.

8. The implantable pulse generator casing of claim 1 wherein the shell is a ceramic material.

9. The implantable pulse generator casing of claim 1 further comprising:
   an optoelectronic iris, in the shell, adjacent the optical window, and directed toward the at least one light emitting device and the at least one light detecting device.

10. The implantable pulse generator casing of claim 1 wherein:
    the optical window further comprises an optical waveguide, positioned adjacent the at least one light emitting device and the at least one light detecting device; and,
    wherein the optical waveguide is configured to be axially aligned with a lead of the set of leads.

11. The implantable pulse generator casing of claim 10 wherein the optical waveguide has an internally reflective cylindrical surface.

12. The implantable pulse generator casing of claim 1 wherein the at least one light emitting device is separated from the at least one light detecting device by an opaque light baffle.

13. The implantable pulse generator casing of claim 1 wherein:
    the at least one light emitting device further comprises a pair of light emitters; and,
    the at least one light detecting device further comprises a pair of light detectors.

14. The implantable pulse generator casing of claim 1 wherein:
    the at least one light emitting device further comprises a single light emitter; and,
    the at least one light detecting device further comprises a single light detector.

15. The implantable pulse generator casing of claim 1 wherein:
the set of instructions includes further instructions that when executed cause the optical signal processor to:
compare the second emitter current to a maximum emitter current; and,
if the second emitter current is equal to or greater than the maximum emitter current, then send a warning signal.

16. The implantable pulse generator casing of claim 1 wherein the shell is defined by a set of ellipse equations.

17. The implantable pulse generator casing of claim 16 wherein the set of ellipse equations further comprises:
a first Lame equation; and,
a second Lame equation.

18. The implantable pulse generator casing of claim 16 wherein the set of ellipse equations is defined in a set of principle axes x, y and z, and further comprises:
a first equation:

$$\left|\frac{a}{2}\right|^2 + \left|\frac{b}{2}\right|^2 = r^2$$

where:
a=a shell width;
b=a shell height;
r=a shell radius;
a second equation:

$$\left|\frac{z}{c}\right|^n + \left|\frac{y}{b}\right|^n = 1$$

where:
n=2, 3 or 4;
b=the shell height;
c=a shell depth; and,
a third equation:

$$\left|\frac{x}{a}\right|^n + \left|\frac{z}{c}\right|^n = 1$$

where:
n=2, 3 or 4;
a=the shell width;
c=the shell depth.

19. The implantable pulse generator casing of claim 1 wherein a lead channel of the set of parallel lead channels further comprises:
a lead stop surface coaxial with the lead channel;
a chamfered ferrule alignment surface coaxial with the lead channel;
a buffer gap between the chamfered ferrule alignment surface and the optical window; and,
wherein the lead stop surface and the chamfered ferrule alignment surface secure a lead on an optical axis of the lead channel.

20. The implantable pulse generator casing of claim 19 wherein the header further comprises:
an anchor section adjacent the chamfered ferrule alignment surface;
a threaded hole radially positioned in the anchor section;
a screw, resident in the threaded hole; and,
wherein advancing the screw secures the lead in the lead channel.

21. The implantable pulse generator casing of claim 19 wherein the lead channel of the set of parallel lead channels further comprises:
a connector bay;
a set of flexible connectors positioned in the connector bay; and,
a connector panel, adjacent the connector bay, electrically connecting at least one flexible connector of the set of flexible connectors to an interior of the shell.

22. The implantable pulse generator casing of claim 1 further comprising:
a battery;
a stimulation signal processor connected to the battery and to the optical signal processor;
an inductive charging coil, connected to the stimulation signal processor; and,
wherein the battery is charged by a signal received by the inductive charging coil.

23. The implantable pulse generator casing of claim 22 further comprising:
an RF antenna, connected to the stimulation signal processor, adapted to send a warning signal from the optical signal processor.

24. The implantable pulse generator casing of claim 1 further comprising:
an inset header bay, in the shell, supporting the optical window; and,
the header hermetically sealed in the inset header bay adjacent the optical window.

* * * * *